United States Patent
Ehlis et al.

(10) Patent No.: US 11,793,742 B2
(45) Date of Patent: Oct. 24, 2023

(54) MIXTURES OF COSMETIC UV ABSORBERS

(71) Applicant: BASF SE, Ludwigshafen (DE)

(72) Inventors: Thomas Ehlis, Freiburg (DE); Julie Grumelard, Village-Neuf (FR)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/302,796

(22) PCT Filed: Apr. 7, 2015

(86) PCT No.: PCT/EP2015/057455
§ 371 (c)(1),
(2) Date: Oct. 7, 2016

(87) PCT Pub. No.: WO2015/155158
PCT Pub. Date: Oct. 15, 2015

(65) Prior Publication Data
US 2017/0027835 A1 Feb. 2, 2017

(30) Foreign Application Priority Data
Apr. 11, 2014 (EP) .................... 14164508

(51) Int. Cl.
A61K 8/49 (2006.01)
A61K 8/35 (2006.01)
(Continued)

(52) U.S. Cl.
CPC .............. A61K 8/4966 (2013.01); A61K 8/35 (2013.01); A61K 8/415 (2013.01); A61K 8/494 (2013.01);
(Continued)

(58) Field of Classification Search
None
See application file for complete search history.

(56) References Cited

U.S. PATENT DOCUMENTS 5,338,539 A  8/1994  Raspanti
5,518,713 A  5/1996  Raspanti
(Continued)

FOREIGN PATENT DOCUMENTS

CH   401469 A    10/1965
CN   102791248 A  11/2012
(Continued)

OTHER PUBLICATIONS

English translation of Dromigny et al. FR 2986154 (Year: 2013).*
(Continued)

Primary Examiner — Nicole P Babson
(74) Attorney, Agent, or Firm — Faegre Drinker Biddle & Reath LLP

(57) ABSTRACT

Disclosed are cosmetic or pharmaceutical composition comprising a UV filter combination of
(a) an aqueous dispersion of 5,6,5',6'-tetraphenyl-3,3'-(1,4-Phenylene)bis(1,2,4-Triazine) corresponding to the formula

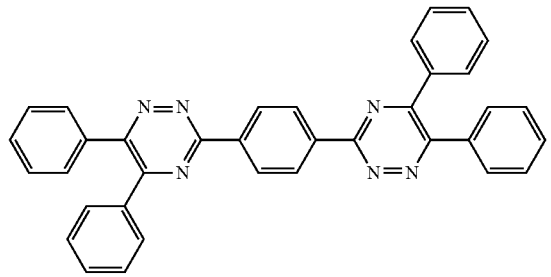

(1)

in particulate form; and
(b) the UV filters selected from
($b_1$) Bis-Ethylhexyloxyphenol Methoxyphenyl Triazine;
($b_2$) Butyl Methoxydibenzoylmethane;
($b_3$) Diethylhexyl Butamido Triazone;
($b_4$) Ethylhexyl Triazone;
($b_5$) Diethylamino Hydroxy Benzoyl Hexyl Benzoate;
($b_6$) Ethylhexyl Methoxycinnamate;
($b_7$) Ethylhexyl Salicylate;
($b_8$) Homosalate;
($b_9$) Octocrylene;
($b_{10}$) Methylene Bis-Benzotriazolyl Tetramethylbutylphenol;
($b_{11}$) Phenylbenzimidazole Sulfonic Acid;
($b_{12}$) Titanium Dioxide;
($b_{13}$) Tris-Biphenyl Triazine; and
($b_{14}$) (2-{4-[2-(4-Diethylamino-2-hydroxy-benzoyl)-benzoyl]-piperazine-1-carbonyl}-phenyl)-(4-diethylamino-2-hydroxy-phenyl)-methanone;
($b_{15}$) BBDAPT; Benzoic acid, 4,4'-[[6-[[3-[1,3,3,3-tetramethyl-1-[(trimethylsilyl)oxy]-1 disiloxanyl]propyl]amino]-1,3,5-triazine-2,4-diyl]diimino]bis-, dibutyl ester;
($b_{16}$) benzylidene malonates; and
($b_{17}$) merocyanine derivatives;
($b_{18}$) Bis(butylbenzoate) diaminotriazine aminopropylsiloxane;
($b_{19}$) Bis-Ethylhexyloxyphenol Methoxyphenyl Triazine) encapsulated in a polymer matrix;
($b_{20}$) 2-(2H-Benzotriazol-2-yl)-6-[(2-ethylhexyloxy)methyl]-4-methylphenol; and
($b_{21}$) 2-Propenoic acid, 3-(4-methoxyphenyl)-, 2-methylphenyl ester.

23 Claims, No Drawings

(51) Int. Cl.
*A61K 8/41* (2006.01)
*A61Q 17/04* (2006.01)
*A61K 8/58* (2006.01)

(52) U.S. Cl.
CPC .............. *A61K 8/496* (2013.01); *A61K 8/585* (2013.01); *A61Q 17/04* (2013.01); *A61K 2800/5922* (2013.01)

(56) References Cited

U.S. PATENT DOCUMENTS

| | | | |
|---|---|---|---|
| 5,601,811 | A | 2/1997 | Gallagher et al. |
| 5,955,060 | A | 9/1999 | Hüglin et al. |
| 6,193,959 | B1 | 2/2001 | Bernasconi et al. |
| 6,365,637 | B1 | 4/2002 | Zirnstein et al. |
| 6,409,998 | B1 | 6/2002 | Candau et al. |
| 6,440,401 | B1 | 8/2002 | Heywang et al. |
| 6,521,217 | B1* | 2/2003 | Luther ............... A61K 8/42 424/400 |
| 7,074,922 | B2 | 7/2006 | Gumbel et al. |
| 7,816,520 | B2 | 10/2010 | Picoul et al. |
| 9,283,160 | B2 | 3/2016 | Herzog et al. |
| 2004/0247536 | A1 | 12/2004 | Chaudhuri |
| 2008/0267892 | A1 | 10/2008 | Picoul et al. |
| 2010/0111884 | A1* | 5/2010 | Acker ............... A61Q 17/04 424/59 |
| 2010/0209463 | A1 | 8/2010 | Pfluecker et al. |
| 2013/0324616 | A1* | 12/2013 | Beck ............... A61K 8/29 514/733 |
| 2015/0050223 | A1 | 2/2015 | Perier et al. |

FOREIGN PATENT DOCUMENTS

| | | |
|---|---|---|
| DE | 1165574 B | 3/1964 |
| DE | 2024051 A1 | 12/1971 |
| DE | 19851777 A1 | 5/2000 |
| DE | 10138496 A1 | 2/2003 |
| DE | 10229995 A1 | 1/2004 |
| DE | 102007035567 A1 | 1/2009 |
| EP | 582189 A2 | 2/1994 |
| EP | 613893 A1 | 9/1994 |
| EP | 0709080 A1 | 5/1996 |
| EP | 775698 A1 | 5/1997 |
| EP | 0893119 A1 | 1/1999 |
| EP | 1093796 A1 | 4/2001 |
| EP | 1093797 A1 | 4/2001 |
| EP | 1167358 A1 | 1/2002 |
| EP | 1371356 A2 | 12/2003 |
| EP | 1371357 A2 | 12/2003 |
| EP | 1371358 A2 | 12/2003 |
| EP | 1483250 A1 | 12/2004 |
| EP | 2196189 A1 | 6/2010 |
| FR | 2252840 A1 | 6/1975 |
| FR | 2477873 A1 | 9/1981 |
| FR | 2986154 A1 | 8/2013 |
| GB | 962919 A | 7/1964 |
| GB | 1333475 A | 10/1973 |
| GB | 1494915 A | 12/1977 |
| GB | 2303549 A | 2/1997 |
| GB | 2319523 A | 5/1998 |
| JP | 2007-536354 A | 12/2007 |
| JP | 2011-504899 A | 2/2011 |
| JP | 2015-505548 A | 2/2015 |
| WO | 95/22959 A2 | 8/1995 |
| WO | WO-9700851 A1 | 1/1997 |
| WO | 98/22447 A1 | 5/1998 |
| WO | WO-9966896 A1 | 12/1999 |
| WO | WO-0025731 A1 | 5/2000 |
| WO | WO-0185124 A1 | 11/2001 |
| WO | WO-0239974 A1 | 5/2002 |
| WO | WO-0341675 A2 | 5/2003 |
| WO | WO-03074499 A1 | 9/2003 |
| WO | 2004/085412 A2 | 10/2004 |
| WO | WO-2005121128 A1 | 12/2005 |
| WO | WO-2009012871 A2 | 1/2009 |
| WO | WO-2011038776 A1 | 4/2011 |
| WO | 2013/113745 A2 | 8/2013 |

OTHER PUBLICATIONS

National Center for Biotechnology Information. PubChem Compound Database; CID=159201, https://pubchem.ncbi.nlm.nih.gov/compound/159201 (accessed Feb. 15, 2018). (Year: 2018).*
U.S. Appl. No. 15/302,750, filed Oct. 7, 2016, BASF SE.
"New solubilizers for organic UV filters in Personal Care—an IP.com Prior Art Database Technical Disclosure", retrieved from ip.com/pdf/ipcompad/IPCOM000158883D.pdf, dated Oct. 4, 2007.
International Search Report for PCT/EP2015/057213 dated Jun. 9, 2015.
International Search Report for PCT/EP2015/057455 dated Sep. 17, 2015.
"A basic guide to particle characterization," White Paper, Spectris Malvern Instruments Limited, 2014, pp. 1-23.
"Ciba(Registered) Tinosorb M-Microfine UV-A Absorber with Triple Action", Ciba Specialty Chemicals, 2002, 20 pages.
"Data Profile—Eumulgin(Registered) L", Revision May 8, 2007, CareChemicals—Cognis Hybrids, 2007, 4 pages.
"Monographs", International Cosmetic Ingredient Dictionary and Handbook, ed. Gottschalck, et al., 11th Edition, vol. 1, 2006, p. 842.
"Particle Size Analysis", Wikipedia, last edited on Feb. 8, 2019, 2 pages. URL: https://en.wikipedia.org/w/index.php?title=Particle_size_analysis&oldid=882331366.
Barber, et al., "A Logical Stepwise Approach to Laser Diffraction Particle Size Distribution Analysis Methods Development and Validation", Pharmaceutical Development and Technology, vol. 3, Issue 2, 1998, pp. 153-161.
Beaubien, et al., "Particle-size analysis of pharmaceutical powders", Journal of Pharmaceutical Sciences, vol. 69, Issue 6, Jun. 1980, pp. 651-655.
Gugliotta, et al., "Latex Particle Size Distribution by Dynamic Light Scattering: Computer Evaluation of Two Alternative Calculation Paths", Journal of Colloid and Interface Science, vol. 228, Issue 1, Aug. 1, 2000, pp. 14-17.
Herzog, B., et al., "New Sunscreen Actives," Sunscreens—Regulation and Commercial Development, Edition: 3rdChapter, Taylor & Francis, Boca Raton, Editors Nadim Shaath, Mar. 2005, pp. 291-320.
Julie Grumeland, "Test results filed by BASF SE during the examination proceedings of the US patent application corresponding to the opposed patent", Mar. 6, 2019, 7 pages.
Osterwalder, U., et al., "UV-A Protection with new Class of UV Absorber," Oct. 2000, pp. 153-164.
Shirinian, et al., "Merocyanines: Synthesis and Application", Heterocyclic Polymethine Dyes, Topics in Heterocyclic Chemistry, ed. L. Strekowski, vol. 14, May 22, 2008, pp. 75-105.p.
Walter Mächtle, "High-Resolution, Submicron Particle Size Distribution Analysis Using Gravitational-Sweep Sedimentation", Biophysical Journal, vol. 76, Issue 2, Feb. 1999, pp. 1080-1091.
"Test results filed by BASF SE during the examination proceedings of the opposed patent", 1 page, Jun. 17, 2019.

* cited by examiner

MIXTURES OF COSMETIC UV ABSORBERS

CROSS-REFERENCE TO RELATED APPLICATIONS

This application is a national stage application (under 35 U.S.C. § 371) of PCT/EP2015/057455, filed Apr. 7, 2015, which claims benefit of European Application No. 14164508.5, filed Apr. 11, 2014, both of which are incorporated herein by reference in their entirety.

The present invention relates to the use of specific UV filter combinations comprising Phenylene Bis-Diphenyltriazine for cosmetic preparations.

It is well known that ultraviolet radiation (light) is harmful to human skin. Depending on the wavelength UV radiation causes different types of skin damage. UV-B radiation (about 290 to 10 about 320 nm) is responsible for sunburn and can cause skin cancer. UV-A radiation (about 320 to about 400 nm) while producing tanning of the skin, contributes also to sunburn and the induction of skin cancers. Moreover, the harmful effects of the UV-B radiation may be aggravated by UV-A radiation.

Therefore, an effective sunscreen formulation preferably comprises both at least one UV-A and UV-B filter and a broad band UV filter covering the full range from about 290 nm to about 400 nm to prevent the human skin from the damage of sunlight.

Surprisingly it has been found that 5,6,5',6'-tetraphenyl-3,3'-(1,4-Phenylene)bis(1,2,4-Triazine) (INCI name: Phenylene Bis-Diphenyltriazine) in micronized form has very good properties in sunscreen compositions in combination with other inorganic and/or organic UV filters.

Therefore the present invention relates to cosmetic or pharmaceutical composition comprising a UV filter combination of (a) an aqueous dispersion of 5,6,5',6'-tetraphenyl-3,3'-(1,4-Phenylene)bis(1,2,4-Triazine) corresponding to the formula

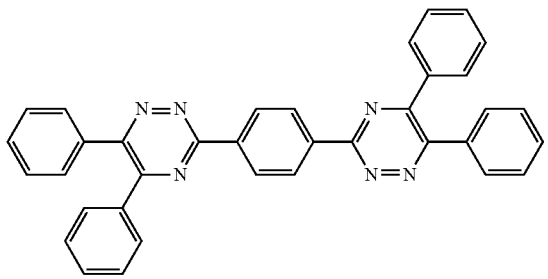

(1)

in particulate form; and
(b) the UV filters selected from
($b_1$) Bis-Ethylhexyloxyphenol Methoxyphenyl Triazine;
($b_2$) Butyl Methoxydibenzoylmethane;
($b_3$) Diethyhexyl Butamido Triazone;
($b_4$) Ethylhexyl Triazone;
($b_5$) Diethylamino Hydroxy Benzoyl Hexyl Benzoate;
($b_6$) Ethylhexyl Methoxycinnamate;
($b_7$) Ethylhexyl Salicylate;
($b_8$) Homosalate;
($b_9$) Octocrylene;
($b_{10}$) Methylene Bis-Benzotriazolyl Tetramethylbutylphenol;
($b_{11}$) Phenylbenzimidazole Sulfonic Acid;
($b_{12}$) Titanium Dioxide;
($b_{13}$) Tris-Biphenyl Triazine; and
($b_{14}$) (2-{4-[2-(4-Dethylamino-2-hydroxy-benzoyl)-benzoyl]-piperazne-1-carbonyl}-phenyl)-(4-diethyl-amino-2-hydroxy-phenyl)-methanone;
($b_{15}$) BBDAPT; Benzoic acid, 4,4'-[[6-[[3-[1,3,3,3-tetramethyl-1-[(trimethylsily)oxy]-1 disiloxanyl]propyl]amino]-1,3,5-triazine-2,4-diyl]diimino]bis-, dibutyl ester;
($b_{16}$) benzylidene malonates; and
($b_{17}$) merocyanine derivatives;
($b_{18}$) Bis(butylbenzoate) diaminotriazine aminopropylsiloxane;
($b_{19}$), Bis-Ethylhexyloxyphenol Methoxyphenyl Triazine) encapsulated in a polymer matrix;
($b_{20}$) 2-(2H-Benzoriazol-2-yl)-6-[(2-ethylhexyloxy) methyl]-4-ethylphenol; and
($b_{21}$) 2-Propenoic acid, 3-(4-methoxyphenyl)-, 2-methylphenyl ester, wherein said composition contains at least two of the UV filters ($b_1$)-($b_{17}$); and
wherein said composition also contains a pharmaceutically or cosmetically acceptable excipient.

The UV filter according to component (a) represents a nanoscalar, particulate organic pigment filter. The compound of formula (1) is characterized by a poor oil-solubility and a high melting point.

The particulate insoluble organic UV filter of formula (1) is preferably present as an aqueous dispersion, comprising the micronized insoluble organic UV absorber of formula (1).

The method for the preparation of the aqueous dispersion is characterized by grinding the insoluble organic UV absorber, in coarse particle form, in a grinding apparatus in the presence of 1 to 50% by weight of a grinding aid.

Any known processes can be used for the preparation of microparticles of the compound of formula (1), for example:

wet-milling (low-viscosity micronization process for pumpable dispersions), with a hard grinding medium, for example zirconium silicate balls in a ball mill, and a protective surfactant or a protective polymer in water or in a suitable organic solvent;

wet-kneading (high-viscosity micronization process for non-pumpable pastes) using a continuous or discontinuous (batch) kneader. For a wet-kneading process, a solvent (water or cosmetically acceptable oils), a grinding aid (surfactant, emulsifier) and a polymeric grinding aid may be used;

spray-drying from a suitable solvent, for example aqueous suspensions or suspensions containing organic solvents, or true solutions in water, ethanol, dichloroethane, toluene or N-methylpyrrolidone etc.;

expansion according to the RESS process (Rapid Expansion of Supercritical Solutions) of supercritical fluids (e.g. $CO_2$) in which the UV filter or filters is/are dissolved, or the expansion of liquid carbon dioxide together with a solution of one or more UV filters in a suitable organic solvent;

reprecipitation from suitable solvents, including supercritical fluids (GASR process=Gas Anti-Solvent Recrystallisation/PCA process=Precipitation with Compressed Anti-solvents).

Wet-kneading and even more wet-milling and are the preferred micronization processes according to the present invention.

Suitable milling equipments for the preparation of the micronized organic UV absorber of formula (1) are for example jet mills, ball mills, vibratory mills or hammer mills, preferably high-speed mixing mills. Even more preferable mills are modem ball mills; manufacturers of these types of mill are, for example, Netzsch (LMZ mill), Drais (DCP-Viscoflow or Cosmo), Bühler AG (centrifugal mills) or Bachhofer. The grinding is preferably carried out with a grinding aid.

Examples of kneading equipments for the preparation of the micronized organic UV absorber of formula (1) are typical sigma-blade batch kneaders but also serial batch kneaders (IKA-Werke) or continuous kneaders (Continua from Werner und Pfleiderer).

Useful low molecular weight grinding aids for all the above micronizing processes are for example anionic, nonionic or amphoteric surfactants and emulsifiers and polymeric grinding aids.

Such surfactant systems may comprise for example: carboxylic acids and their salts: alkaline soap of sodium, potassium and ammonium, metallic soap of calcium or magnesium, organic basis soap such as lauric, myristic, palmitic, stearic and oleic acid etc.; alkyl phosphates or phosphoric acid esters, acid phosphate, diethanolamine phosphate, potassium cetyl phosphate; ethoxylated carboxylic acids or polyethyleneglycol esters, PEG-n acylates; fatty alcohol polyglycolether such as laureth-n, myreth-n, ceteareth-n, steareth-n, oleth-n; fatty acid polyglycolether such as PEG-n stearate, PEG-n oleate, PEG-n cocoate; monoglycerides and polyol esters; C12-C22 fatty acid mono- and di-esters of addition products of from 1 to 100 mol of ethylene oxide with polyols; fatty acid and polyglycerol ester such as monostearate glycerol, diisostearoyl polyglyceryl-3-diisostearates, polyglyceryl-3-diisostearates, triglyceryl dilsostearates, polyglyceryl-2-sesqulisostearates or polyglyceryl dimerates; fatty acid polyglycolesters such as monostearate diethylene glycol, fatty acid and polyethylene glycol esters, fatty acid and saccharose esters such as sucro esters, glycerol and saccharose esters such as sucro glycerides; sorbitol and sorbitan, sorbitan mono- and di-esters of saturated and unsaturated fatty acids having from 6 to 22 carbon atoms and ethylene oxide addition products; polysorbate-n series, sorbitan esters such as sesquiisostearate, sorbitan, PEG-(6)-isostearate sorbitan, PEG-(10)-sorbitan laurate, PEG-17-dioleate sorbitan; glucose derivatives, C8-C22 alkyl-mono and oligo-glycosides and ethoxylated analogues with glucose being preferred as the sugar component; O/W emulsifiers such as methyl gluceth-20 sesquistearate, sorbitan stearate/sucrose cocoate, methyl glucose sesquistearate, cetearyl alcohol/cetearyl glucoside; W/O emulsifiers such as methyl glucose dioleate/methyl glucose isostearate; sulfates and sulfonated derivatives, dialkylsulfosuccinates, dioctyl succinate, alkyl lauryl sulfonate, linear sulfonated parafins, sulfonated tetraproplyne sulfonate, sodium lauryl sulfates, ammonium and ethanolamine lauryl sulfates, lauyl ether sulfates, sodium laureth sulfates [Texapon N70] or sodium myreth sulfates [Texapon K14S], sulfosuccinates, acetyl isothionates, alkanolamide sulfates, taurines, methyl taurines, imidazole sulfates. Zwitterionic or amphoteric surfactants that carry at least one quaternary ammonium group and at least one carboxylate and/or sulfonate group in the molecule.

Examples for zwitterionic surfactants are especially suitable are betaines, such as N-alkyl-N,N-dimethylammonium glycinates, cocoalkyldimethylammonium glycinate, N-acylamino-propyl-N,N-dimethylammonium glycinates, cocoacylaminopropyldimethylammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxymethyl-glycinate, N-alkylbetaine, N-alkylaminobetaines.

Examples of suitable mild surfactants are dispersing agents, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Examples of nonionic surfactants are PEG-6 beeswax (and) PEG-6 stearate (and) polyglyceryl-2-isostearate [Apifac], glyceryl stearate (and) PEG-100 stearate. [Arlacel 165], PEG-5 glyceryl stearate [arlatone 983 S], sorbitan oleate (and) polyglyceryl-3 ricinoleate. [Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20[Polawax GP 200, Polawax NF], cetearyl alcohol and cetearyl polyglucoside [Emulgade PL 1618], cetearyl alcohol and ceteareth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and szeareth-7 and steareth-10 [Emulsifying wax U.S.N.F], glyceryl stearate and PEG-75 stearate [Gelot 64], propylene glycol ceteth-3 acetate. [Hetester PCS], propylene glycol isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X].

Examples for anionic emulsifiers are PEG-2 stearate SE, glyceryl stearate SE [Monelgine, Cutina KD], propylene glycol stearate [Tegin P], cetearyl Alcohol and Sodium cetearyl sulfate [Lanette N, Cutina LE, Crodacol GP], cetearyl alcohol and sodium lauryl sulfate [Lanette W], trilaneth-4 phopshate and glycol stearate and PEG-2 stearate [Sedefos 75], glyceryl stearate and sodium lauryl Sulfate [Teginacid Special]. Cationic acid bases such as cetearyl alcohol and cetrimonium bromide.

Examples for fatty alcohols are Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of C12-C15 alcohols, acetylated lanolin alcohol, etc.

Useful polymeric grinding aids for water dispersion are cosmetically acceptable water-soluble polymers with Mn>500 g/mol, for example: acrylates (Salcare types), modified or non-modified polysaccharides, polyglucosides or xanthan gum. Furthermore an alkylated vinylpyrrolidone polymer, a vinylpyrrolidone/vinyl acetate copolymer, an acyl glutamate, an alkyl polyglucoside, Ceteareth-25 or a phospholipid may be used. Oil dispersions may comprise cosmetically acceptable waxy polymers or natural waxes as polymeric grinding aid to adjust the viscosity during and after processing.

Preferred useful grinding aids according to the present invention are anionic surfactants with a HLB (Hydrophile-Lipophile Balance) value higher than 8, more preferably higher than 10.

Most preferred grinding aid is PPG-1-PEG-9 Lauryl Glycol Ether (Eumulgin L from BASF).

The micronized UV absorber of formula (1) so obtained usually has an average particle size from 0.02 to 2 µm, preferably from 0.05 to 1.5 µm, and more especially from 0.1 to 1.0 µm.

The UV absorber of formula (1) can also be used dry in powder form. For that purpose the UV absorber is subjected to known grinding methods, such as vacuum atomization, countercurrent spray-drying etc. Such powders have a particle size from 0.1 µm to 2 µm.

The UV absorber of formula (1) can also be used as a concentrated aqueous polymer dispersion with an average particle size of less than 1000 nm comprising a polymer carrier prepared by heterophase radical polymerization of at least one ethylenically unsaturated monomer, for example methyl methacrylate (MMA), stearyl methacrylate (SMA) or butandioldiacrylate (BDDA) or mixtures thereof in the presence of the UV absorber of formula (1), wherein the weight ratio of the UV absorber of formula (1) to polymer carrier is greater than 50 parts UV absorber per 100 parts of carrier.

In this case the aqueous dispersion preferably contains the micronized particulate insoluble organic UV absorber of formula (1) in a concentration range from 40-50% b.w.

Alternatively, the particulate insoluble UV absorber of formula (1) may be encapsulated in a polymer carrier. In this case the aqueous dispersion preferably contains the encapsulated particulate insoluble organic UV filter of formula (1) in a concentration range from 20-50% b.w.

Bis(butylbenzoate) diaminotriazine aminopropylsiloxane ($b_{18}$) corresponds to formula (B18)

Tinosorb S, Bis-Ethylhexyloxyphenol Methoxyphenyl Triazine encapsulated in a polymer matrix ($b_{19}$) is described in IP.com Journal (2009), 9(1B), 17 (Tinosorb S aqua, BASF).

2-(2H-Benzotriazol-2-yl)-6-[(2-ethylhexyloxy)methyl]-4-methylphenol ($b_{20}$) corresponds to formula

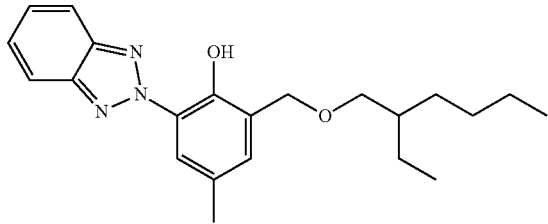

(B20)

2-Propenoic acid, 3-(4-methoxyphenyl)-, 2-methylphenyl ester ($b_{21}$) corresponds to formula

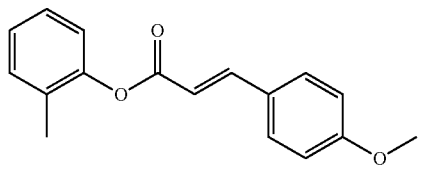

(B21)

Preferably, the cosmetic or pharmaceutical composition according to the present invention contains a mixture of at least 3 UV filters, comprising
(UV1) Phenylene Bis-Diphenyltriazine (a) of formula (1);
(UV2) Bis-Ethylhexyloxyphenol Methoxyphenyl Triazine ($b_1$); and
(UV3) filters selected from
  ($UV3_1$) Diethylamino Hydroxy Benzoyl Hexyl Benzoate ($b_5$);
  ($UV3_2$) Butyl Methoxydibenzoylmethane ($b_2$); and
  ($UV3_3$) Benzoic acid, 4,4'-[[6-[[3-[1,3,3,3-tetramethyl-1-[(trimethylsilyl)oxy]-1 disiloxanyl]-propyl]amino]-1,3,5-triazine-2,4-diyl]diimino]bis-, dibutyl ester ($b_{15}$); or
(UV1) Phenylene Bis-Diphenyltriazine (a) of formula (1);
(UV2) Methylene Bis-Benzotriazolyl Tetramethylbutylphenol ($b_{10}$); and
(UV3) filters selected from
  ($UV3_1$) Bis-Ethylhexyloxyphenol Methoxyphenyl Triazine ($b_1$);
  ($UV3_2$) Diethylamino Hydroxy Benzoyl Hexyl Benzoate ($b_5$);
  ($UV3_3$) Butyl Methoxydibenzoylmethane ($b_2$); and
  ($UV3_4$) Benzoic acid, 4,4'-[[6-[[3-[1,3,3,3-tetramethyl-1-[(trimethylsilyl)oxy]-1 disiloxanyl]-propyl]amino]-1,3,5-triazine-2,4-diyl]diimino]bis-, dibutyl ester; or
(UV1) Phenylene Bis-Diphenyltriazine (a) of formula (1);
(UV2) Diethylamino Hydroxy Benzoyl Hexyl Benzoate ($b_5$); and
(UV3) Butyl Methoxydibenzoylmethane ($b_2$); or
(UV1) Phenylene Bis-Diphenyltriazine (a) of formula (1);
(UV2) Ethylhexyl Triazone ($b_4$);
and UV filters (UV3) selected from
  ($UV3_1$) Methylene Bis-Benzotriazolyl Tetramethylbutylphenol ($b_{10}$);
  ($UV3_2$) Bis-Ethylhexyloxyphenol Methoxyphenyl Triazine ($b_1$);
  ($UV3_3$) Diethylamino Hydroxy Benzoyl Hexyl Benzoate ($b_5$);
  ($UV3_4$) Butyl Methoxydibenzoylmethane ($b_2$); and
  ($UV3_5$) Benzoic acid, 4,4'-[[6-[[3-[1,3,3,3-tetramethyl-1-[(trimethylsilyl)oxy]-1 disiloxanyl]-propyl]amino]-1,3,5-triazine-2,4-diyl]diimino]bis-, dibutyl ester ($b_{15}$); or
(UV1) Phenylene Bis-Diphenyltriazine (a) of formula (1);
(UV2) Benzoic acid, 4,4'-[[6-[[3-(1,3,3,3-tetramethyl-1-[(trimethylsilyl)oxy]-1 disiloxanyl]-propyl]amino-1,3,5-triazine-2,4-diyl]diimino]bis-, dibutyl ester ($b_{15}$);
and UV filters (UV3) selected from
  ($UV3_1$) Methylene Bis-Benzotriazolyl Tetramethylbutylphenol ($b_{10}$);
  ($UV3_2$) Bis-Ethylhexyloxyphenol Methoxyphenyl Triazine ($b_1$);
  ($UV3_3$) Diethylamino Hydroxy Benzoyl Hexyl Benzoate ($b_5$); and
  ($UV3_4$) Butyl Methoxydibenzoylmethane ($b_2$).

Preferably, the cosmetic or pharmaceutical compositions according to the present invention contain a mixture of at least 4 UV filters, comprising
(UV1) Phenylene Bis-Diphenyltriazine (a) of formula (1);
(UV2) Methylene Bis-Benzotriazolyl Tetramethylbutylphenol ($b_{10}$);
(UV3) Ethylhexyl Triazone ($b_4$);
and UV filters (UV4) selected from
  ($UV4_1$) Bis-Ethylhexyloxyphenol Methoxyphenyl Triazine ($b_1$);

(UV4₂) Diethylamino Hydroxy Benzoyl Hexyl Benzoate (b₅);
(UV4₃) Butyl Methoxydibenzoylmethane (b₂); and
(UV4₄) Benzoic acid, 4,4'-[[6-[[3-[1,3,3,3-tetramethyl-1-[(trimethylsilyl)oxy]-1 disiloxanyl]]-propyl] amino]-1,3,5-triazine-2,4-diyl]diimino]bis-, dibutyl ester (b₁₅); or (UV1) Phenylene Bis-Diphenyltriazine (a) of formula (1);
(UV2) Bis-Ethylhexyloxyphenol Methoxyphenyl Triazine (b₁);
(UV3) Ethylhexyl Triazone (b₄);
and the UV filters (UV4) selected from
    (UV4₁) Diethylamino Hydroxy Benzoyl Hexyl Benzoate (b₅);
    (UV4₂) Butyl Methoxydibenzoylmethane (b₂); and
    (UV4₃) Benzoic acid, 4,4'-[[6-[[3-[1,3,3,3-tetramethyl-1-[(trimethylsilyl)oxy]-1 disiloxanyl]-propyl] amino]-1,3,5-triazine-2,4-diyl]diimino]bis-, dibutyl ester (b₁₅); or (UV1) Phenylene Bis-Diphenyltriazine (a) of formula (1);
(UV2) Diethylamino Hydroxy Benzoyl Hexyl Benzoate (b₅);
(UV3) Butyl Methoxydibenzoylmethane (b₂); and
(UV4) Ethylhexyl Triazone (b₄).

Preferably, the cosmetic or pharmaceutical compositions according to the present invention contain a mixture of at least 5 UV filters, comprising
(UV1) Phenylene Bis-Diphenyltriazine (a) of formula (1);
(UV2) Bis-Ethylhexyloxyphenol Methoxyphenyl Triazine (b₁);
(UV3) Ethylhexyl Triazone (b₄);
the UV filters (UV4) selected from
    (UV4₁) Methylene Bis-Benzotriazolyl Tatramethylbutylphenyl (b₁₀
    (UV4₂) Diethylamino Hydroxy Benzoyl Hexyl Benzoate (b₅); and
    (UV4₃) Butyl Methoxydibenzoylmethane (b₂); and
the UV filters (UV5) selected from
    (UV5₁) Ethylhexyl Salicylate (b₇);
    (UV5₂) Tris-Biphenyl Triazine (b₁₃);
    (UV5₃) Octocrylene (b₉);
    (UV5₄) Diethylhexyl Butamido Triazone (b₃);
    (UV5₅) Phenylbenzimidazole Sulfonic Acid (b₁₁);
    (UV5₆) Titanium Dioxide (b₁₂)
    (UV5₇) Homosalate (b₉);
    (UV5₈) (2-{4-[2-(4-Diethylamino-2-hydroxy-benzoyl)-benzoyl]-piperazine-1-carbonyl}-phenyl)-(4-diethylamino-2-hydroxy-phenyl)-methanone (b₁₄); and
    (UV5₉) Benzoic acid, 4,4'-[[6-[[3-[1,3,3,3-tetramethyl-1-[(trimethylsilyl)oxy]-1 disiloxanyl]-propyl] amino]-1,3,5-triazine-2,4-diyl]diimino]bis-, dibutyl ester (b₁₅); or (UV1) Phenylene Bis-Diphenyltriazine (a) of formula (1);
(UV2) Methylene Bis-Benzotriazolyl Tetramethylbutylphenol (b₁₀);
(UV3) Ethyhexyl Triazone (b₄);
the UV filters (UV4) selected from
    (UV4₁) Diethylamino Hydroxy Benzoyl Hexyl Benzoate (b₅)
    (UV4₂) Butyl Methoxydibenzoylmethane (b₂);
and the UV filters (UV5) selected from
    (UV5₁) Ethyhexyl Salicylate (b₇)
    (UV5₂) Tris-Biphenyl Triazine (b₁₃)
    (UV5₃) Octocrylene (b₉)
    (UV5₄) Diethylhexyl Butamido Triazone (b₃)
    (UV5₅) Phenylbenzimidazole Sulfonic Acid (b₁₁)
    (UV5₆) Titanium Dioxide (b₁₂)
    (UV5₇) Homosalate (b₈)
    (UV5%) (2-{4-[2-(4-Diethylamino-2-hydroxy-benzoyl)-benzoyl]-piperazine-1-carbonyl}-phenyl)-(4-diethylamino-2-hydroxy-phenyl)-methanone (b₁₄); and
    (UV5₉) Benzoic acid, 4,4'-[[6-[3-[1,3,3,3-tetramethyl-1-[(trimethylsilyl)oxy]-1 disiloxanyl]-propyl] amino)-1,3,5-triazine-2,4-diyl]diimino]bis-, dibutyl ester (b₁₅).

Preferably the UV filters (b₁₀) Methylene Bis-Benzotriazolyl Tetramethylbutylphenol, (b₁₃) Tris-Biphenyl Triazine and (b₁₄) (2-{4-[2-(4-Diethylamino-2-hydroxy-benzoyl)-benzoyl]-piperazine-1-carbonyl}-phenyl)-(4-diethylamino-2-hydroxy-phenyl)-methanone are present in the cosmetic or pharmaceutical composition in their micronized state.

The Benzylidene malonates (b₁₆) preferably correspond to formula (2)

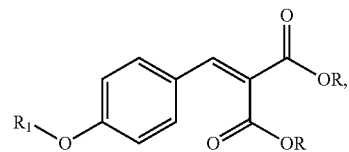

wherein
R₁ is methyl; ethyl; propyl; or n-butyl;
if R₁ is methyl, then
R is tert. butyl;

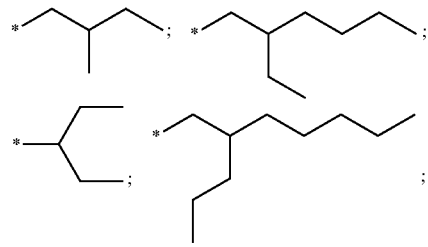

a radical of formula (2a)

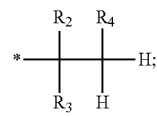

or a radical of formula (2b)

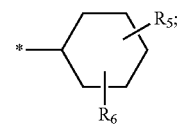

wherein
R₂ and R₃, independently from each other are hydrogen; or methyl;
R₄ is methyl; ethyl; or n-propyl;
R₅ and R₆ independently from each other are hydrogen; or $C_1$-$C_3$alkyl;

if $R_1$ is ethyl; propyl; or n-butyl, then
R is isopropyl.
Preferably UV filter ($b_{16}$) corresponds to formula (2), wherein
$R_1$ is methyl; ethyl; propyl; or n-butyl;
if $R_1$ is methyl, then
R is tert. butyl

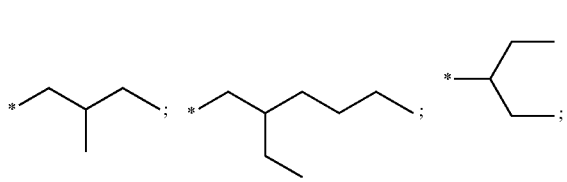

a radical of formula (2a)

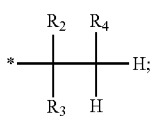

or a radical of formula (2b)

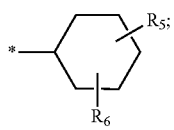

wherein
$R_2$ and $R_3$, independently from each other are hydrogen; or methyl;
$R_4$ is methyl; ethyl; or n-propyl;
$R_5$ and $R_6$ independently from each other are hydrogen; or $C_1$-$C_3$alkyl;
if $R_1$ is ethyl; propyl; or n-butyl, then
R is isopropyl.

Preferably, in formula (2)
R is a radical of formula

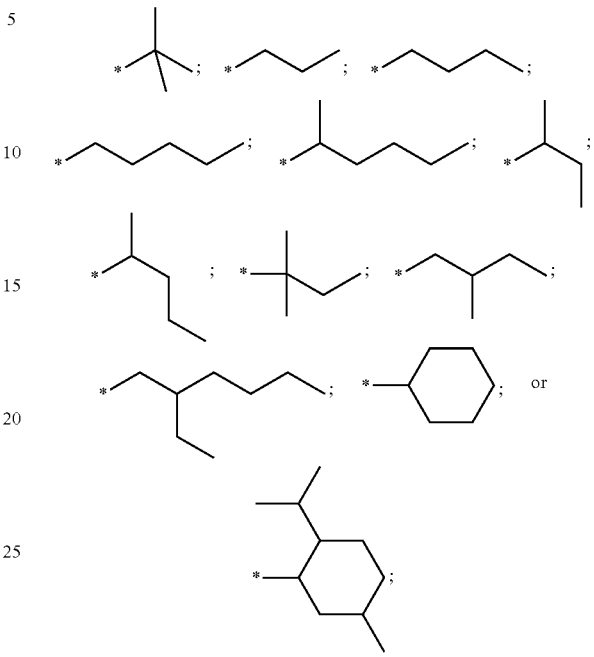

and
$R_1$ is methyl.
Most preferred are compounds of formula (2), wherein in formula (2a) at least one of $R_2$ or $R_3$ is methyl.
Most preferred are also compounds of formula (2), wherein in formula (2a) $R_2$ and $R_3$ are methyl.
Preferred are also compounds of formula (2), wherein
$R_1$ is ethyl; propyl; or n-butyl; and
R is isopropyl.
Examples of compounds of formula (2) are listed in the Table 1 below:

TABLE 2

Examples of preferred benzylidene malonates (MBM) ($b_{16}$) according to the present invention

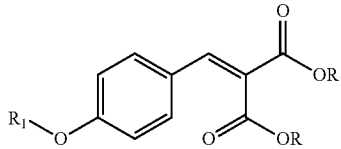

| Compound of formula | $R_1$ | R |
|---|---|---|
| MBM-01 | methyl |  |
| MBM-02 | methyl |  |
| MBM-03 | methyl |  |
| MBM-04 | methyl |  |

TABLE 2-continued

Examples of preferred benzylidene malonates (MBM) (b$_{16}$) according to the present invention

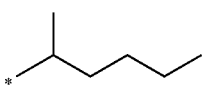

| Compound of formula | R$_1$ | R |
|---|---|---|
| MBM-05 | methyl | 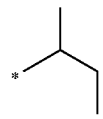 |
| MBM-06 | methyl | 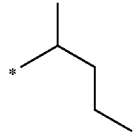 |
| MBM-07 | methyl | 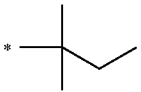 |
| MBM-08 | methyl | 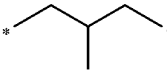 |
| MBM-09 | methyl | 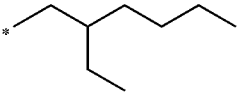 |
| MBM-10 | methyl |  |
| MBM-11 | ethyl |  |
| MBM-12 | propyl |  |
| MBM-13 | n-butyl | 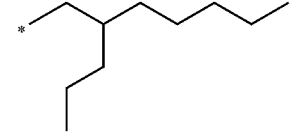 |
| MBM-14 | methyl |  |
| MBM-15 | propyl | Me$_3$Si—* |
| MBM-16 | 2-ethyl-hexyl | Me$_3$Si—CH$_2$—* |
| MBM-17 | iso-octyl | Me$_3$Si—(CH$_2$)$_2$—* |
| MBM-18 | 2-ethyl-hexyl | Me$_3$Si—(CH$_2$)$_3$—* |
| MBM-19 | 2-ethyl-hexyl | MeSi(OSiMe$_3$)$_2$CH$_2$CH$_2$CH$_2$—* |

TABLE 2-continued
Examples of preferred benzylidene malonates (MBM) (b$_{16}$) according to the present invention
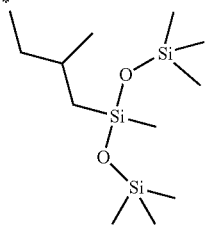
| Compound of formula | R$_1$ | R |
|---|---|---|
| MBM-20 | methyl |  |
| MBM-21 | Me$_3$Si—* | 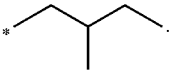 |
| MBM-22 | Me$_3$Si—CH$_2$—* |  |
| MBM-23 | Me$_3$Si—(CH$_2$)$_2$—* | 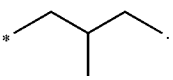 |
| MBM-24 | Me$_3$Si—(CH$_2$)$_3$—* |  |
| MBM-25 | MeSi(OSiMe$_3$)$_2$CH$_2$CH$_2$CH$_2$—* | 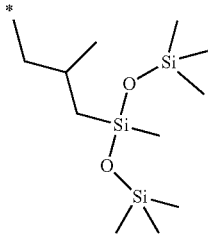 |
| MBM-26 |  | 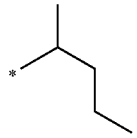 |
| MBM-27 | Me$_3$Si—(CH$_2$)$_2$—* | 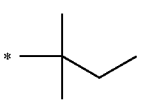 |
| MBM-28 | Me$_3$Si—(CH$_2$)$_3$—* | 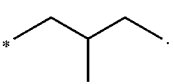 |
| MBM-29 | MeSi(OSiMe$_3$)$_2$CH$_2$CH$_2$CH$_2$—* |  |

TABLE 2-continued
Examples of preferred benzylidene malonates (MBM) ($b_{16}$) according to the present invention
| Compound of formula | $R_1$ | R |
|---|---|---|
| MBM-30 | (2-methylbutyl-siloxane group) | isopropyl |
| MBM-31 | tert-butyl | isobutyl |
| MBM-32 | isobutyl | isopropyl |
| MBM-33 | menthyl | ethyl |
| MBM-34 | methyl | menthyl |
Most preferred benzylidene malonate ($b_{16}$) are the compound of formula
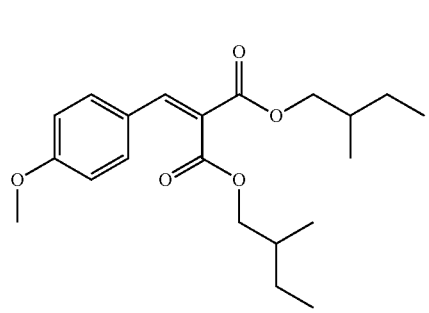
MBM-9
and
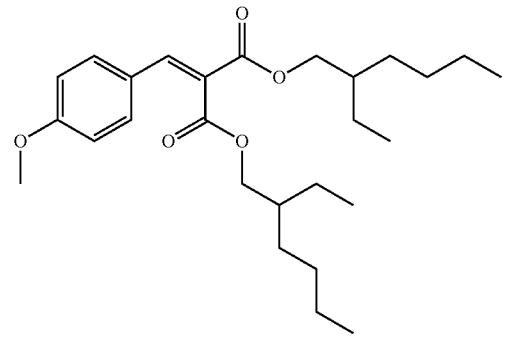
MBM-10

The cosmetic or pharmaceutical composition according to the present invention is especially useful for the protection of organic materials that are sensitive to ultraviolet light, especially human and animal skin and hair, against the action of UV radiation. Such UV filter combinations are therefore suitable as light-protective agents in cosmetic, pharmaceutical and veterinary medicine preparations.

The cosmetic or pharmaceutical composition according to the present invention contains from 0.1 to 15% by weight, preferably from 0.5 to 10% by weight, based on the total weight of the composition, the UV absorber mixture (a) and (b) and a cosmetically tolerable adjuvant.

The cosmetic or pharmaceutical composition according to the present invention can be prepared by physically mixing the UV absorbers with the adjuvant using customary methods, for example by simply stirring together the individual components, especially by making use of the dissolution properties of already known cosmetic UV absorbers, for example Ethylhexyl Methoxycinnamate. The UV absorbers can be used, for example, without further treatment.

Alternatively the UV filter can be used in their micronized state, preferably the UV filters ($b_{10}$) Methylene Bis-Benzotriazolyl Tetramethylbutylphenol, ($b_{13}$) Tris-Biphenyl Triazine and ($b_{14}$) (2-{4-[2-(4-Diethylamino-2-hydroxy-benzoyl)-benzoyl]-piperazine-1-carbonyl}-phenyl)-(4-diethylamino-2-hydroxy-phenyl)-methanone, or in the form of a powder.

In addition to other properties, the cosmetic or pharmaceutical composition according to the present invention can be used as radical scavengers by to reducing significantly the number of UV-induced free radicals in skin when applied in a suitable cosmetic carrier.

The cosmetic composition may comprise, in addition to the UV absorber combination according to the invention, one or more further UV protective agents of the following substance classes: p-aminobenzoic acid derivatives, salicylic acid derivatives, benzophenone derivatives, 3-imidazol-4-yl acrylic acid and esters; benzofuran derivatives, polymeric UV absorbers, camphor derivatives, encapsulated UV absorbers, and 4,4-diphenyl-1,3-butadiene derivatives.

Special preference is given to the light-protective agents indicated in the following Table 3:

TABLE 3

Suitable UV filter substances and adjuvants which can be additionally used with the UV absorber Phenylene Bis-Diphenyltriazine according to the present invention

| Chemical Name | CAS No. |
| --- | --- |
| (+/−)-1,7,7-trimethyl-3-[(4-methylphenyl)methylene]bicyclo[2.2.1]heptan-2-one; p-methyl benzylidene camphor | 36861-47-9 |
| 1,7,7-trimethyl-3-(phenylmethylene)bicyclo[2.2.1]heptan-2-one; benzylidene camphor | 15087-24-8 |
| (2-Hydroxy-4-methoxyphenyl)(4-methylphenyl)methanone | 1641-17-4 |
| 2,4-dihydroxybenzophenone | 131-56-6 |
| 2,2',4,4'-tetrahydroxybenzophenone | 131-55-5 |
| 2-Hydroxy-4-methoxy benzophenone; | 131-57-7 |
| 2,2'-dihydroxy-4,4'-dimethoxybenzophenone | 131-54-4 |
| 2,2'-Dihydroxy-4-methoxybenzophenone | 131-53-3 |
| Alpha-(2-oxoborn-3-ylidene)toluene-4-sulphonic acid and its salts (Mexoryl SL) | 56039-58-8 |
| Methyl N,N,N-trimethyl-4-[(4,7,7-trimethyl-3-oxobicyclo[2,2,1]hept-2-ylidene)methyl]anilinium sulphate (Mexoryl SO) | 52793-97-2 |
| Isopentyl p-methoxycinnamate; isoamyl methoxy cinnamate | 71617-10-2 |
| Menthyl-o-aminobenzoate | 134-09-8 |
| Menthyl salicylate | 89-46-3 |
| 4-aminobenzoic acid | 150-13-0 |
| Benzoic acid, 4-amino-, ethyl ester, polymer with oxirane | 113010-52-9 |
| 2-Propenamide, N-[[4-[(4,7,7-trimethyl-3-oxobicyclo[2.2.1]hept-2-ylidene)methyl]phenyl]methyl]-, homopolymer | 147897-12-9 |
| Triethanolamine salicylate | 2174-16-5 |
| 3,3'-(1,4-phenylenedimethylene)bis[7,7-dimethyl-2-oxo-bicyclo[2.2.1]heptane-1 methanesulfonic acid] (Cibafast H) | 90457-82-2 |
| Zinc oxide (primary particle size 20-100 nm) For example Zinc oxide NDM, Zinc oxide Z-Cote HP1, Nanox Zinc oxide | 1314-13-2 |
| Benzoic acid, 4,4'-[[6-[[4-[[(1,1-dimethylethyl)amino]carbonyl]-phenyl]amino]1,3,5-triazine-2,4-diyl]diimino]bis-, bis(2-ethylhexyl)ester; diethylhexyl butamido triazone (Uvasorb HEB) | 154702-15-5 |
| Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane (Mexoryl XL) | 155633-54-8 |
| Dimethicodiethylbenzalmalonate; Polysilicone 15 (Parsol SLX) | 207574-74-1 |
| Benzenesulfonic acid, 3-(2H-benzotriazol-2-yl)-4-hydroxy-5-(1-methylpropyl)-, monosodium salt (Tinogard HS) | 92484-48-5 |
| 1-Dodecanaminium, N-[3-[[4-(dimethylamino)benzoyl]amino]propyl]N,N-dimethyl-, salt with 4-methylbenzenesulfonic acid (1:1) (Escalol HP610) | 156679-41-3 |
| 1-Propanaminium, N,N,N-trimethyl-3-[(1-oxo-3-phenyl-2-propenyl)-amino]-, chloride | 177190-98-6 |
| 1H-Benzimidazole-4,6-disulfonic acid, 2,2'-(1,4-phenylene)bis- | 170864-82-1 |
| 1,3,5-Triazine,2,4,6-tris(4-methoxyphenyl)- | 7753-12-0 |
| 1,3,5-Triazine,2,4,6-tris[4-[(2-ethylhexyl)oxy]phenyl]- | 208114-14-1 |
| 1-Propanaminium, 3-[[3-[3-(2H-benzotriazol-2-yl)-5-(1,1-dimethylethyl)-4-hydroxyphenyl]-1-oxopropyl]amino]-N,N-diethyl-N-methyl-, methyl sulfate (salt) | 340964-15-0 |
| 2-Propenoic acid, 3-(1H-imidazol-4-yl)- | 104-98-3 |
| Benzoic acid, 2-hydroxy-, [4-(1-methylethyl)phenyl]methyl ester | 94134-93-7 |
| 1,2,3-Propanetriol, 1-(4-aminobenzoate) (Glyceryl PABA) | 136-44-7 |

TABLE 3-continued

Suitable UV filter substances and adjuvants which can be additionally used with the UV absorber Phenylene Bis-Diphenyltriazine according to the present invention

| Chemical Name | CAS No. |
| --- | --- |
| Benzeneacetic acid, 3,4-dimethoxy-a-oxo- | 4732-70-1 |
| 2-Propenoic acid, 2-cyano-3,3-diphenyl-, ethyl ester | 5232-99-5 |
| Anthralinic acid, p-menth-3-yl ester | 134-09-8 |
| 2,2'-bis(1,4-phenylene)-1H-benzimidazole-4,6-disulphonic acid mono sodium salt or Disodium phenyl dibenzimidazole tetrasulfonate (Neo Heliopan AP) | 349580-12-7 |
| sterols (cholesterol, lanosterol, phytosterols), as described in WO0341675 | |
| mycosporines and/or mycosporine-like amino acids as described in WO2002039974, e.g. Helioguard 365 from Milbelle AG, isolated mycosporine like amino acids from the red alga *porphyra umbilicalis* (INCI: *Porphyra Umbilicalis*) that are encapsulated into liposomes) | |
| alpha-lipoic-acid as described in DE 10229995 | |
| synthetic organic polymers as described in EP 1 371 358, [0033]-[0041] | |
| phyllosilicates as described in EP 1371357 [0034]-[0037] | |
| silica compounds as described in EP1371356, [0033]-[0041] | |
| inorganic particles as described in DE10138496 [0043]-[0055] | |
| latex particles as described in DE10138496 [0027]-[0040] | |
| 1H-Benzimidazole-4,6-disulfonic acid, 2,2'-(1,4-phenylene)bis-, disodium salt; Bisimidazylate (Neo Heliopan APC) | 180898-37-7 |
| Di-2-ethylhexyl-3,5-dimethoxy-4-hydroxy-benzalmalonate (Oxynex ST, EMD Chemicals, as described in US 20040247536) | |
| Z-COTE ® MAX: Zinc Oxide (and) Diphenyl Capryl Methicone | |
| Z-COTE HP1: Zinc Oxide (and) Triethoxycaprylylsilane | |
| 1,3,5-Triazine-2,4,6-triamine, N2,N4-bis[4-[5-(1,1-dimethylpropyl)-2-benzoxazolyl]phenyl]-N6-(2-ethylhexyl)- (Uvasorb K2A) | 288254-16-0 |
| 1,1-[(2,2'-Dimethylpropoxy)carbonyl]-4,4-diphenyl-1,3-butadiene | 363602-15-7 |
| UV filter capsules containing an organic sunscreen as described in DE102007035567 or WO 2009012871 | |

If the compositions according to the present invention represent water- and oil-containing emulsions (e.g. W/O, O/W, O/W/O and W/O/W emulsions or microemulsions) they contain, for example, from 0.1 to 30% by weight, preferably from 0.1 to 15% by weight and especially from 0.5 to 10% by weight, based on the total weight of the composition, of the mixture of component (a) and (b), from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically tolerable adjuvants.

Suitable oil components of oil-containing compositions (e.g. oils, W/O, O/W, O/W/O and W/O/W emulsions or microemulsions) are for example Guerbet alcohols based on fatty alcohols having from 6 to 18, preferably from 8 to 10, carbon atoms, esters of linear $C_3$-$C_{24}$ fatty acids with linear $C_3$-$C_{24}$ alcohols, esters of branched $C_6$-$C_{13}$ carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or trimer triol) and/or Guerbet alcohols, triglycerides based on $C_6$-$C_{10}$ fatty acids, liquid mono-/di-/tri-glyceride mixtures based on $C_6$-$C_{18}$ fatty acids, esters of $C_6$-$C_{24}$ fatty alcohols and/or Guerbet alcohols with aromatic carboxylic acids, especially benzoic acid, esters of $C_2$-$C_{12}$ dicarboxylic acids with linear or branched alcohols having from 1 to 22 carbon atoms or polyols having from 2 to 10 carbon atoms and from 2 to 6 hydroxy groups, vegetable oils (such as sunflower oil, olive oil, soybean oil, rapeseed oil, almond oil, jojoba oil, orange oil, wheat germ oil, peach kernel oil and the liquid components of coconut oil), branched primary alcohols, substituted cyclohexanes, linear and branched $C_6$-$C_{22}$ fatty alcohol carbonates, Guerbet carbonates, esters of benzoic acid with linear and/or branched $C_6$-$C_{24}$ alcohols (e.g. Finsolv® TN), linear or branched, symmetric or asymmetric dialkyl ethers having a total of from 12 to 36 carbon atoms, especially from 12 to 24 carbon atoms, for example di-n-octyl ether, di-n-decyl ether, di-n-nonyl ether, di-n-undecyl ether, di-n-dodecyl ether, n-hexyl n-octyl ether, n-octyl n-decyl ether, n-decyl n-undecyl ether, n-undecyl n-dodecyl ether, n-hexyl n-undecyl ether, di-tert-butyl ether, diisopentyl ether, di-3-ethyldecyl ether, tert-butyl n-octyl ether, isopentyl n-octyl ether and 2-methyl pentyl-n-octyl ether; ring-opening products of epoxidised fatty acid esters with polyols, silicone oils and/or aliphatic or naphthenic hydrocarbons. Also of importance are monoesters of fatty acids with alcohols having from 3 to 24 carbon atoms. That group of substances comprises the esterification products of fatty acids having from 8 to 24 carbon atoms, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols). Of special importance are isopropyl myristate, isononanoic acid $C_{16}$-$C_{18}$alkyl esters, stearic acid 2-ethylhexyl ester, cetyl oleate, glycerol tricaprylate, coconut fatty alcohol caprinate/caprylate and n-butyl stearate. Further oil components that can be used are dicarboxylic acid esters, such as di-n-butyl adipate, di(2-ethylhexyl) adipate, di(2-ethylhexyl) succinate and diisotridecyl acetate, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Preferred mono- or poly-ols are ethanol, isopropanol, propylene glycol, hexylene glycol, glycerol and sorbitol. It is also possible to use di- and/or trivalent metal salts (alkaline earth metal, $Al^{3+}$ inter alia) of one or more alkyl carboxylic acids.

The oil components can be used in an amount of, for example, from 1 to 60% by weight, especially from 5 to 50% by weight and preferably from 10 to 35% by weight, based on the total weight of the composition.

Any conventionally usable emulsifier can be used for the cosmetic compositions according to the present invention.

Suitable emulsifiers are for example, non-ionic surfactants from the following groups:

addition products of from 2 to 30 mol of ethylene oxide and/or from 0 to 5 mol of propylene oxide with linear fatty alcohols having from 8 to 22 carbon atoms, with fatty acids having from 12 to 22 carbon atoms and with alkylphenols having from 8 to 15 carbon atoms in the alkyl group, for example ceteareth-20 or ceteareth-12;

$C_{12}$-$C_{22}$ fatty acid mono- and di-esters of addition products of from 1 to 30 mol of ethylene oxide with polyols having from 3 to 6 carbon atoms, especially with glycerol;

glycerol mono- and di-esters and sorbitan mono- and di-esters of saturated and unsaturated fatty acids having from 6 to 22 carbon atoms and ethylene oxide addition products thereof, for example glyceryl stearates, glyceryl isostearates, glyceryl oleates, sorbitan oleates or sorbitan sesquioleates;

$C_8$-$C_{22}$alkyl-mono- and -oligo-glycosides and ethoxylated analogues thereof, degrees of oligomerisation of from 1.1 to 5, especially from 1.2 to 1.4, being preferred, and glucose being preferred as the sugar component;

addition products of from 2 to 60 mol, especially from 15 to 60 mol, of ethylene oxide with castor oil and/or hydrogenated castor oil;

polyol esters and especially polyglycerol esters, for example diisostearoyl polyglyceryl-3-diisostearates, polyglyceryl-3-diisostearates, triglyceryl dilsostearates, polyglyceryl-2-sesquiisostearates or polyglyceryl dimerates. Mixtures of compounds from a plurality of those substance classes are also suitable;

partial esters based on linear, branched, unsaturated or saturated $C_6$-$C_{22}$ fatty acids, ricinoleic acid and also 12-hydroxystearic acid and on glycerol, polyglycerol, pentaerythritol, dipentaerythritol, sugar alcohols (e.g. sorbitol), alkyl glucosides (e.g. methyl glucoside, butyl glucoside, lauryl glucoside) and also polyglucosides (e.g. cellulose), for example polyglyceryl-2-dihydroxystearates or polyglyceryl-2-diricinoleates;

mono-, di- and tri-alkylphosphates and also mono-, di- and/or tri-PEG-alkylphosphates and salts thereof;

wool wax alcohols;

one or more ethoxylated esters of natural derivatives, for example polyethoxylated esters of hydrogenated castor oil;

silicone oil emulsifiers, for example silicone polyol;

polysiloxane/polyalkyl/polyether copolymers and corresponding derivatives, for example cetyl dimethicone copolyol;

mixed esters of pentaerythritol, fatty acids, citric acid and fatty alcohol (see DE-A-1 165 574) and/or mixed esters of fatty acids having from 6 to 22 carbon atoms, methylglucose and polyols, preferably glycerol or polyglycerol, for example polyglyceryl-3-glucose distearates, polyglyceryl-3-glucose dioleates, methyl glucose dioleates or dicocoyl pentaerythryl distearyl citrates; and also polyalkylene glycols.

The addition products of ethylene oxide and/or of propylene oxide with fatty alcohols, fatty acids, alkylphenols, glycerol mono- and di-esters and also sorbitan mono- and di-esters of fatty acids, or with castor oil, are known, commercially available products. They are usually homologue mixtures, the average degree of alkoxylation of which corresponds to the ratio of the amounts of ethylene oxide and/or propylene oxide and substrate with which the addition reaction is carried out. $C_{12}$-$C_{18}$ fatty acid mono- and di-esters of addition products of ethylene oxide with glycerol are known, for example, from DE-A-2 024 051 as fat-restoring substances for cosmetic preparations.

$C_8$-$C_{18}$Alkyl-mono- and -oligo-glycosides, their preparation and their use are known from the prior art. They are prepared especially by reacting glucose or oligosaccharides with primary alcohols having from 8 to 18 carbon atoms. Suitable glycoside radicals include monoglycosides in which a cyclic sugar radical is glycosidically bonded to the fatty alcohol and also oligomeric glycosides having a degree of oligomerisation of up to preferably about 8. The degree of oligomerisation is a statistical average value based on a homologue distribution customary for such technical-grade products.

It is also possible to use zwitterionic surfactants as emulsifiers. The term "zwitterionic surfactants" denotes especially surface-active compounds that carry at least one quaternary ammonium group and at least one carboxylate and/or sulfonate group in the molecule. Zwitterionic surfactants that are especially suitable are the so-called betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines each having from 8 to 18 carbon atoms in the alkyl or acyl group and also cocoacylaminoethylhydroxyethycarboxymethylglycinate. Special preference is given to the fatty acid amide derivative known by the CTFA name cocamidopropyl betaine. Likewise suitable as emulsifiers are ampholytic surfactants. Ampholytic surfactants are to be understood as meaning especially those which, in addition to containing a $C_8$-$C_{18}$-alkyl or -acyl group, contain at least one free amino group and at least one —COOH or —$SO_3H$ group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group.

Ampholytic surfactants to which special preference is given are N-cocoalkylamino-propionate, cocoacylaminoethylaminopropionate and $C_{12}$-$C_{18}$acylsarcosine. In addition to the ampholytic emulsifiers there also come into consideration quaternary emulsifiers, special preference is given to those of the esterquat type, preferably methyl-quaternised di-fatty acid triethanolamine ester salts.

Non-ionic emulsifiers are preferred, preferably ethoxylated fatty alcohols having from 8 to 22 carbon atoms and from 4 to 30 EO units.

The emulsifiers may be used in an amount of, for example, from 1 to 30% by weight, especially from 4 to 20% by weight and preferably from 5 to 10% by weight, based on the total weight of the composition. It is, however, also possible in principle to dispense with the use of emulsifiers.

The compositions according to the invention, for example creams, gels, lotions, alcoholic and aqueous/alcoholic solutions, emulsions, wax/fat compositions, stick preparations, powders or ointments, may in addition contain, as further adjuvants and additives, mild surfactants, super-fatting agents, pearlescent waxes, consistency regulators, thickeners, polymers, silicone compounds, fats, waxes, stabilisers, biogenic active ingredients, deodorising active ingredients, anti-dandruff agents, film formers, swelling agents, antioxidants, hydrotropic agents, preservatives, insect repellents, self-tanning agents, solubilizers, perfume oils, colorants, bacteria-inhibiting agents and the like.

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilsers.

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ether carboxylic acids, alkyl oligoglucosides, fatty acid glucamides, alkylamidobetaines and/or protein fatty acid condensation products, the latter preferably being based on wheat proteins.

Suitable pearlescent are for example: alkylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Suitable consistency regulators are especially fatty alcohols or hydroxy fatty alcohols having from 12 to 22 carbon atoms and preferably from 16 to 18 carbon atoms, and in addition partial glycerides, fatty acids and hydroxy fatty acids. Preference is given to a combination of such substances with alkyl-oligoglucosides and/or fatty acid N-methylglucamides of identical chain length and/or polyglycerol poly-12-hydroxystearates. Suitable thickeners include, for example, Aerosil types (hydrophilic silicic acids), polysaccharides, especially xanthan gum, guar-guar, agar-agar, alginates and Tyloses, carboxymethyl cellulose and hydroxymethyl cellulose, also relatively high molecular weight polyethylene glycol mono- and di-esters of fatty acids, polyacrylates (e.g. Carbopol® from Goodrich or Synthalen® from Sigma), polyacrylamides, polyvinyl alcohol and polyvinylpyrrolidone, surfactants, for example ethoxylated fatty acid glycerides, esters of fatty acids with polyols, for example pentaerythritol or trimethylolpropane, fatty alcohol ethoxylates with restricted homologue distribution and alkyl-oligoglucosides as well as electrolytes, such as sodium chloride or ammonium chloride.

Suitable cationic polymers are, for example, cationic cellulose derivatives, for example a quaternised hydroxymethyl cellulose obtainable under the name Polymer JR 400® from Amerchol, cationic starch, copolymers of diallylammonium salts and acrylamides, quaternised vinylpyrrolidone/vinyl imidazole polymers, for example Luviquat® (BASF), condensation products of polyglycols and amines, quaternised collagen polypeptides, for example lauryldimonium hydroxypropyl hydrolyzed collagen (Lamequat® L/Grünau), quaternised wheat polypeptides, polyethyleneimine, cationic silicone polymers, for example amidomethicones, copolymers of adipic acid and dimethylaminohydroxypropyldiethylenetriamine (Cartaretin®/Sandoz), copolymers of acrylic acid with dimethyldiallylammonium chloride (Merquat® 550/Chemviron), polyaminopolyamides, as described, for example, in FR-A-2 252 840, and the crosslinked water-soluble polymers thereof, cationic chitin derivatives, for example quaternised chitosan, optionally distributed as microcrystals; condensation products of dihaloalkyls, for example dibromobutane, with bisdialkylamines, for example bisdimethylamino-1,3-propane, cationic guar gum, for example Jaguar® C-17, Jaguar® C-16 from Celanese, quaternised ammonium salt polymers, for example Mirapol® A-15, Mirapol® AD-1, Mirapol® AZ-1 from Miranol.

Suitable anionic, zwitterionic, amphoteric and non-ionic polymers are for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyltrimethylammonium chloride/acrylate copolymers, octyl acrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones.

Suitable silicone compounds are, for example, dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Typical examples of fats are glycerides, and as waxes there come into consideration, inter alia, beeswax, carnauba wax, candelilla wax, montan wax, paraffin wax, hydrogenated castor oils and fatty acid esters or microwaxes solid at room temperature optionally in combination with hydrophilic waxes, e.g. cetylstearyl alcohol or partial glycerides. Metal salts of fatty acids, for example magnesium, aluminium and/or zinc stearate or ricinoleate, may be used as stabilizers.

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Suitable deodorizing active ingredients are for example, antiperspirants like aluminium chlorohydrates (see J. Soc. Cosm. Chem. 24, 281 (1973)). Aluminium chlorohydrate corresponding to formula $Al_2(OH)_5Cl\times 2.5H_2O$, known and commercially available under the trade mark Locron® of Hoechst AG, Frankfurt (FRG), is especially preferred (see J. Pharm. Pharmacol. 26, 531 (1975)). Beside the chlorohydrates, it is also possible to use aluminium hydroxy-acetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen® CAT, Henkel KGaA, Düsseldorf/FRG), which inhibit enzyme activity and hence reduce odour formation. Further suitable esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the microbial flora and kill, or inhibit the growth of, sweat-decomposing bacteria can likewise be present in the preparations (especially in stick preparations). Examples include chitosan, phenoxyethanol and chlorhexidine gluconate. 5-Chloro-2-(2,4-dichlorophenoxy)-phenol (Irgasan®, BASF has also proved especially effective.

Suitable anti-dandruff agents are for example, climbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds. Suitable swelling agents for aqueous phases are montmorillonites, clay mineral substances, Pemulen and also alkyl-modified types of Carbopol (Goodrich). Further suitable polymers and swelling agents can be found in the review by R. Lochhead in Cosm. Toil. 108, 95 (1993).

In addition to the primary light-protective substances it is also possible to use secondary light-protective substances of the antioxidant type which interrupt the photochemical reaction chain triggered when UV radiation penetrates the skin or hair. Typical examples of such antioxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, γ-linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sufoximines, homocysteine sulfoximine, buthionine sulfones, penta-, hexa-, hepta-thionine sulfoximine) in very small tolerable amounts (e.g. from pmol to µmol/kg), also (metal) chelating agents (e.g. α-hydroxy fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, α-glycosylrutin, ferulic acid, furfurylidene glucitol, carnosine, butyl hydroxytoluene, butyl hydroxyanisole, resinous nordihydroguaiaretic acid, nordihydroguaiaretic acid, trihydroxybutyrophenone, uric acid and derivatives thereof, mannose and derivatives thereof, superoxide dismutase, N-[3-(3,5-di-tert-butyl-4-hydroxyphenyl)propionyl]sulfanilic acid (and salts thereof, for example the sodium salts), zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned. The amount of antioxidants present is usually from 0.001 to 30% by weight, preferably from 0.01 to 3% by weight, based on the weight of the cosmetic composition according to the present invention.

For improvement of the flow behavior it is also possible to employ hydrotropic agents, for example ethanol, isopropyl alcohol or polyols. Suitable polyols for that purpose comprise preferably from 2 to 15 carbon atoms and at least two hydroxy groups.

The polyols may also contain further functional groups, especially amino groups, and/or may be modified with nitrogen. Typical examples are as follows:

glycerol;

alkylene glycols, for example ethylene glycol, diethylene glycol, propylene glycol, butylene glycol, hexylene glycol and also polyethylene glycols having an average molecular weight of from 100 to 1000 dalton;

technical oligoglycerol mixtures having an intrinsic degree of condensation of from 1.5 to 10, for example technical diglycerol mixtures having a diglycerol content of from 40 to 50% by weight;

methylol compounds, such as, especially, trimethylolethane, trimethylolpropane, trimethylolbutane, pentaerythrtol and dipentaerythritol;

lower alkyl-glucosides, especially those having from 1 to 8 carbon atoms in the alkyl radical, for example methyl and butyl glucoside;

sugar alcohols having from 5 to 12 carbon atoms, for example sorbitol or mannitol; sugars having from 5 to 12 carbon atoms, for example glucose or saccharose; amino sugars, for example glucamine;

dialcohol amines, such as diethanolamine or 2-amino-1, 3-propanediol.

Suitable preservatives include, for example, phenoxyethanol, formaldehyde solution, Parabens, pentanediol or sorbic acid and the further substance classes listed in Schedule 6, Parts A and B of the Cosmetics Regulations.

Suitable perfume oils are mixtures of natural and/or synthetic aromatic substances. Representatives of natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, oibanum, opoponax). Animal raw materials also come into consideration, for example civet and castoreum. Typical synthetic aromatic substances are, for example, products of the ester, ether, aldehyde, ketone, alcohol or hydrocarbon type.

Aromatic substance compounds of the ester type are, for example, benzyl acetate, phenoxy-ethyl isobutyrate, p-tert-butylcyclohexyl acetate, linalyl acetate, dimethyl-benzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, α-isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, di hydromyrcenol, lilial, lyral, citronellol, phenyl ethyl alcohol, α-hexyl cinnamaldehyde, geraniol, benzyl acetone, cyclamen aldehyde, linalool, bosambrene forte, ambroxan, indole, hedione, sandelice, lemon oil, tangerine oil, orange oil, allyl amyl glycolate, cyclovertal, lavandin oil, muscatel sage oil, β-damascone, bourbon geranium oil, cyclohexyl salicylate, vertofix coeur, iso-E-Super, Fixolide NP, evernyl, iraldein gamma, phenylacetic acid, geranyl acetate, benzyl acetate, rose oxide, romiliat, irotyl and floramat alone or in admixture with one another.

As colourants the substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106 may be used. The colourants are usually used in concentrations of from 0.001 to 0.1% by weight, based on the total mixture.

Typical examples of bacteria-inhibiting agents are preservatives that have a specific action against gram-positive bacteria, such as 2,4,4'-trichloro-2-hydroxydiphenyl ether, chlorhexidine (1,6-di(4-chlorophenyl-biguanido)hexane) or TCC (3,4,4'-trichlorocarbanilide).

A large number of aromatic substances and ethereal oils also have antimicrobial properties. Typical examples are the active ingredients eugenol, menthol and thymol in clove oil, mint oil and thyme oil. A natural deodorizing agent of interest is the terpene alcohol farnesol (3,7,11-trimethyl-2, 6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the cosmetic composition according to the present invention.

The cosmetic compositions according to the present invention may furthermore contain as adjuvants anti-foams, such as silicones, structurants, such as maleic acid, solubilizers, such as ethylene glycol, propylene glycol, glycerol or diethylene glycol, opacifiers, such as latex, styrene/PVP or styrene/acrylamide copolymers, complexing agents, such as EDTA, NTA, β-alaninediacetic acid or phosphonic acids, propellants, such as propane/butane mixtures, $N_2O$, dimethyl ether, $CO_2$, $N_2$ or air, so-called coupler and developer components as oxidation dye precursors, thioglycolic acid and derivatives thereof, thiolactic acid, cysteamine, thiomalic acid or α-mercaptoethanesulfonic acid as reducing agents or hydrogen peroxide, potassium bromate or sodium bromate as oxidizing agents.

Insect repellents are for example, N,N-diethyl-m-toluamide, 1,2-pentanediol or insect repellent 3535.

Suitable self-tanning agents are dihydroxyacetone, erythrulose or mixtures of dihydroxyacetone and erythrulose.

Cosmetic formulations according to the invention are contained in a wide variety of cosmetic preparations, especially the following preparations:

skin-care preparations, e.g. skin-washing and cleansing preparations in the form of tablet-form or liquid soaps, synthetic detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eye shadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and anti-perspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, parfume), parfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

The final formulations may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellant gas or pump-action spray) or an aerosol, in the form of a foam, or in the form of a paste.

Important cosmetic compositions for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection oils, sun protection milks and sun protection preparations in the form of a spray.

Important cosmetic compositions for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition:
0.01 to 5% by weight of a UV absorber composition according to the invention,
12.0% by weight of sodium laureth-2-sulfate,
4.0% by weight of cocamidopropyl betaine,
3.0% by weight of sodium chloride, and
water ad 100%.

Especially the following hair-cosmetic formulations may be used:

$a_1$) spontaneously emulsifying stock formulation, consisting of the UV absorber according to the invention, PEG-6-$C_{10}$oxoalcohol and sorbitan sesquioleate, to which water and any desired quaternary ammonium compound, for example 4% minkamidopropyl-dimethyl-2-hydroxyethylammonium chloride or Quaternium 80 is added;

$a_2$) spontaneously emulsifying stock formulation consisting of the UV absorber according to the invention, tributyl citrate and PEG-20-sorbitan monooleate, to which water and any desired quaternary ammonium compound, for example 4% minkamidopropyl-dimethyl-2-hydroxyethylammonium chloride or Quaternium 80 is added;

b) Quat-doped solutions of the UV absorber according to the invention in butyltriglycol and tributyl citrate;

c) mixtures or solutions of the UV absorber according to the invention with n-alkylpyrrolidone.

A. Preparation Examples

Preparation of a Micronized UV Absorber Dispersion 100 parts of the compound of formula (1) is milled together with zirconium silicate bells (diameter: 0.1 to 4 mm) as grinding aids, a dispersing agent (15 parts PPG-1-PEG-9 Lauryl Glycol Ether) and water (85 parts) in a ball mill to a mean particle size of $d_{50}$=130 nm. Benzoic acid is then added to the dispersion as preservative. A thickener may be optionally used (Xanthan gum, PVP)

According to this method a micropigment dispersion of a UV absorber of formula (1) is obtained.

B. Formulation Examples

In the following Examples percentages relate to weight. The amounts of the micronized Phenylene Bis-Diphenyltriazine compounds used correspond to the pure substance.

Legend:
\* particulate organic filter 50-200 nm, aqueous dispersion, active ingredient 40-50 w/w %
\*\* particulate organic filter 50-200 nm, encapsulated active ingredient 20 w/w %
\*\*\* particulate inorganic filter 10-200 nm, active ingredient 80-100 w/w %

O/W Formulation

Anionic System Emulsifier

| | | Example B1: Emulsion high Protection | | | | | | | | |
|---|---|---|---|---|---|---|---|---|---|---|
| | INCI-Name | 1A % w/w | 1B % w/w | 1C % w/w | 1D % w/w | 1E % w/w | 1F % w/w | 1G % w/w | 1H % w/w | 1I % w/w |
| Part A | Cyclomethicone | 2.00 | 2.00 | 2.00 | 2.00 | 2.00 | 2.00 | 2.00 | 2.00 | 2.00 |
| | Dibutyl Adipate | 4.00 | 4.00 | 4.00 | 4.00 | 4.00 | 4.00 | 4.00 | 4.00 | 4.00 |
| | Tridecyl Trimellitate | 3.00 | 3.00 | 3.00 | 3.00 | 3.00 | 3.00 | 3.00 | 3.00 | 3.00 |
| | C12-15 Alkyl Benzoate | 1.00 | 1.00 | 1.00 | 1.00 | 1.00 | 1.00 | 1.00 | 1.00 | 1.00 |
| | Ethylhexyl Palmitate | 3.00 | 3.00 | 3.00 | 3.00 | 3.00 | 3.00 | 3.00 | 3.00 | 3.00 |

Example B1: Emulsion high Protection

|  | INCI-Name | 1A % w/w | 1B % w/w | 1C % w/w | 1D % w/w | 1E % w/w | 1F % w/w | 1G % w/w | 1H % w/w | 1I % w/w |
|---|---|---|---|---|---|---|---|---|---|---|
|  | Glyceryl Stearate | 1.50 | 1.50 | 1.50 | 1.50 | 1.50 | 1.50 | 1.50 | 1.50 | 1.50 |
|  | Potassium Cetyl Phosphate | 1.80 | 1.80 | 1.80 | 1.80 | 1.80 | 1.80 | 1.80 | 1.80 | 1.80 |
|  | VP/Eicosene Copolymer | 0.60 | 0.60 | 0.60 | 0.60 | 0.60 | 0.60 | 0.60 | 0.60 | 0.60 |
| Part B | Aqua | Qs to 100 | Qs to 100 | Qs to 100 | Qs to 100 | Qs to 100 | Qs to 100 | Qs to 100 | Qs to 100 | Qs to 100 |
|  | Acrylates/Palmeth-25 Acrylate Copolymer | 0.25 | 0.25 | 0.25 | 0.25 | 0.25 | 0.25 | 0.25 | 0.25 | 0.25 |
|  | Glycerin | 6.00 | 6.00 | 6.00 | 6.00 | 6.00 | 6.00 | 6.00 | 6.00 | 6.00 |
|  | Disodium EDTA | 0.20 | 0.20 | 0.20 | 0.20 | 0.20 | 0.20 | 0.20 | 0.20 | 0.20 |
| Part C | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
|  | Tocopheryl Acetate | 0.30 | 0.30 | 0.30 | 0.30 | 0.30 | 0.30 | 0.30 | 0.30 | 0.30 |
|  | Diethylamino Hydroxy Benzoyl Hexyl Benzoate |  |  |  |  |  |  |  |  | 2.00 |
|  | Ethylhexyl Triazone | 2.00 |  | 2.00 |  | 2.00 |  | 2.00 |  |  |
|  | BBDAPT (CAS Nb: 207562-42-3) |  |  |  |  |  |  |  |  | 2.00 |
|  | Ethylhexyl Methoxycinnamate |  | 4.00 |  |  |  | 2.00 |  | 7.00 | 7.00 |
|  | MBM-09 |  | 6.00 |  | 14.00 |  | 10.00 |  |  |  |
|  | Bis-Ethylhexyloxyphenol Methoxyphenyl Triazine |  |  | 2.00 | 2.00 |  |  | 2.00 | 2.00 | 2.00 |
|  | Methylene Bis-Benzotriazolyl Tetramethylbutylphenol * |  |  |  |  | 3.00 | 3.00 | 3.00 | 3.00 |  |
|  | Phenylene Bis-Diphenyltriazine * | 4.00 | 4.00 | 4.00 | 4.00 | 4.00 | 4.00 | 4.00 | 4.00 | 2.00 |

Example B2: Sun Milk

|  | INCI-Name | 2A % w/w | 2B % w/w | 2C % w/w | 2D % w/w | 2E % w/w | 2F % w/w | 2G % w/w | 2H % w/w | 2I % w/w |
|---|---|---|---|---|---|---|---|---|---|---|
| Part A | C12-15 Alkyl Benzoate | 2.00 | 2.00 | 2.00 | 2.00 | 2.00 | 2.00 | 2.00 | 2.00 | 2.00 |
|  | Dicaprylyl Carbonate | 4.00 | 4.00 | 4.00 | 4.00 | 4.00 | 4.00 | 4.00 | 4.00 | 4.00 |
|  | Tridecyl Trimellitate | 3.00 | 3.00 | 3.00 | 3.00 | 3.00 | 3.00 | 3.00 | 3.00 | 3.00 |
|  | Coco-Caprylate | 1.00 | 1.00 | 1.00 | 1.00 | 1.00 | 1.00 | 1.00 | 1.00 | 1.00 |
|  | Isohexadecane | 3.00 | 3.00 | 3.00 | 3.00 | 3.00 | 3.00 | 3.00 | 3.00 | 3.00 |
|  | Cyclopentasiloxane | 4.00 | 4.00 | 4.00 | 4.00 | 4.00 | 4.00 | 4.00 | 4.00 | 4.00 |
|  | Stearic Acid | 0.50 | 0.50 | 0.50 | 0.50 | 0.50 | 0.50 | 0.50 | 0.50 | 0.50 |
|  | PEG-100 Stearate (and) Glyceryl Stearate | 0.80 | 0.80 | 0.80 | 0.80 | 0.80 | 0.80 | 0.80 | 0.80 | 0.80 |
|  | Potassium Cetyl Phosphate | 1.30 | 1.30 | 1.30 | 1.30 | 1.30 | 1.30 | 1.30 | 1.30 | 1.30 |
|  | PVP/Eicosene Copolymer | 1.00 | 1.00 | 1.00 | 1.00 | 1.00 | 1.00 | 1.00 | 1.00 | 1.00 |
| Part B | Aqua | Qs to 100 | Qs to 100 | Qs to 100 | Qs to 100 | Qs to 100 | Qs to 100 | Qs to 100 | Qs to 100 | Qs to 100 |
|  | Propylene Glycol | 5.00 | 5.00 | 5.00 | 5.00 | 5.00 | 5.00 | 5.00 | 5.00 | 5.00 |
|  | Xanthan Gum | 0.20 | 0.20 | 0.20 | 0.20 | 0.20 | 0.20 | 0.20 | 0.20 | 0.20 |
|  | Acrylates/C10-30 Alkyl Methacrylate Copolymer | 0.15 | 0.15 | 0.15 | 0.15 | 0.15 | 0.15 | 0.15 | 0.15 | 0.15 |
|  | Disodium EDTA | 0.15 | 0.15 | 0.15 | 0.15 | 0.15 | 0.15 | 0.15 | 0.15 | 0.15 |
| Part C | Triethanolamine | Qs | Qs | Qs | Qs | Qs | Qs | Qs | Qs | Qs |
|  | Dimethicone | 0.40 | 0.40 | 0.40 | 0.40 | 0.40 | 0.40 | 0.40 | 0.40 | 0.40 |
|  | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
|  | Tocopheryl Acetate | 0.90 | 0.90 | 0.90 | 0.90 | 0.90 | 0.90 | 0.90 | 0.90 | 0.90 |
|  | Diethylamino Hydroxy Benzoyl Hexyl Benzoate |  |  |  |  |  |  |  |  | 2.00 |
|  | Ethylhexyl Triazone | 2.00 | 1.00 |  |  |  |  | 2.00 | 2.00 | 2.00 |
|  | BBDAPT (CAS Nb: 207562-42-3) |  | 1.00 |  |  |  |  |  |  | 2.00 |
|  | Ethylhexyl Methoxycinnamate | 7.00 | 7.00 |  |  |  |  |  |  |  |
|  | Bis-Ethylhexyloxyphenol Methoxyphenyl Triazine |  | 2.00 |  | 2.00 |  | 2.00 | 2.00 |  | 2.00 |
|  | Methylene Bis-Benzotriazolyl Tetramethylbutylphenol * | 3.00 | 3.00 |  |  | 3.00 | 3.00 |  | 3.00 | 3.00 |

-continued

Example B2: Sun Milk

| INCI-Name | 2A % w/w | 2B % w/w | 2C % w/w | 2D % w/w | 2E % w/w | 2F % w/w | 2G % w/w | 2H % w/w | 2I % w/w |
|---|---|---|---|---|---|---|---|---|---|
| MBM-09 | | | 10.00 | 10.00 | 10.00 | 10.00 | 10.00 | 10.00 | 10.00 |
| Micronized Phenylene Bis-Diphenyltriazine | 4.00 | 4.00 | 4.00 | 4.00 | 4.00 | 4.00 | 4.00 | 4.00 | 2.00 |

O/W Formulation
Nonionic System Emulsifier

Example B3: Sun cream

| | INCI-Name | 3A % w/w | 3B % w/w | 3C % w/w | 3D % w/w | 3E % w/w | 3F % w/w | 3G % w/w | 3H % w/w | 3I % w/w |
|---|---|---|---|---|---|---|---|---|---|---|
| Part A | Cetearyl glucoside | 4.00 | 4.00 | 4.00 | 4.00 | 4.00 | 4.00 | 4.00 | 4.00 | 4.00 |
| | C12-15 Alkyl Benzoate | 4.00 | 4.00 | 4.00 | 4.00 | 4.00 | 4.00 | 4.00 | 4.00 | 4.00 |
| | Triisodecyl Trimellitate | 3.00 | 3.00 | 3.00 | 3.00 | 3.00 | 3.00 | 3.00 | 3.00 | 3.00 |
| | Dibutyl Adipate | 0.50 | 0.50 | 0.50 | 0.50 | 0.50 | 0.50 | 0.50 | 0.50 | 0.50 |
| | Dicaprylyl Carbonate | 3.00 | 3.00 | 3.00 | 3.00 | 3.00 | 3.00 | 3.00 | 3.00 | 3.00 |
| Part B | Water | Qs to 100 | Qs to 100 | Qs to 100 | Qs to 100 | Qs to 100 | Qs to 100 | Qs to 100 | Qs to 100 | Qs to 100 |
| | Disodium EDTA | 0.20 | 0.20 | 0.20 | 0.20 | 0.20 | 0.20 | 0.20 | 0.20 | 0.20 |
| | Glycerin | 6.00 | 6.00 | 6.00 | 6.00 | 6.00 | 6.00 | 6.00 | 6.00 | 6.00 |
| | PVP/dimethylconylacrylate/polycarbamyl/polyglycol ester | 3.00 | 3.00 | 3.00 | 3.00 | 3.00 | 3.00 | 3.00 | 3.00 | 3.00 |
| | Sodium polyacrylate | 0.70 | 0.70 | 0.70 | 0.70 | 0.70 | 0.70 | 0.70 | 0.70 | 0.70 |
| Part C | Dimethicone | 3.00 | 3.00 | 3.00 | 3.00 | 3.00 | 3.00 | 3.00 | 3.00 | 3.00 |
| | Corn Starch modified | 3.00 | 3.00 | 3.00 | 3.00 | 3.00 | 3.00 | 3.00 | 3.00 | 3.00 |
| Part D | Phenoxyethanol (and) Methylparaben (and) Ethylparaben (and) Butylparaben (and) Propylparaben (and) Isobutylparaben | 1.00 | 1.00 | 1.00 | 1.00 | 1.00 | 1.00 | 1.00 | 1.00 | 1.00 |
| | Diethylamino Hydroxy Benzoyl Hexyl Benzoate | | | | | | | | | 2.00 |
| | Ethylhexyl Triazone | 2.00 | | 2.00 | | 2.00 | | 2.00 | | 2.00 |
| | BBDAPT (CAS Nb: 207562-42-3) | | 7.00 | | | | | | 2.00 | 2.00 |
| | Ethylhexyl Methoxycinnamate | | 7.00 | | | | | | 2.00 | 2.00 |
| | MBM-09 | | | | 14.00 | | 14.00 | | 10.00 | 10.00 |
| | Bis-Ethylhexyloxyphenol Methoxyphenyl Triazine | | | 2.00 | 2.00 | | | 2.00 | 2.00 | 2.00 |
| | Methylene Bis-Benzotriazolyl Tetramethylbutylphenol * | | | | | 3.00 | 3.00 | 3.00 | 3.00 | |
| | Bis-Ethylhexyloxyphenol Methoxyphenyl Triazine ** | 2.00 | 2.00 | 2.00 | 2.00 | 2.00 | 2.00 | 2.00 | 2.00 | 2.00 |
| | Phenylene Bis-Diphenyltriazine * | 10.00 | 10.00 | 10.00 | 10.00 | 6.00 | 3.00 | 2.00 | 8.00 | 6.00 |

Example B4: Sun Cream

| | INCI-Name | 4A % w/w | 4B % w/w | 4C % w/w | 4D % w/w | 4E % w/w | 4F % w/w | 4G % w/w | 4H % w/w | 4I % w/w |
|---|---|---|---|---|---|---|---|---|---|---|
| Part A | Tribehenin PEG-20 esters | 5.00 | 5.00 | 5.00 | 5.00 | 5.00 | 5.00 | 5.00 | 5.00 | 5.00 |
| | C12-15 Alkyl Benzoate | 4.00 | 4.00 | 4.00 | 4.00 | 4.00 | 4.00 | 4.00 | 4.00 | 4.00 |
| | Tridecyl Trimellitate | 3.00 | 3.00 | 3.00 | 3.00 | 3.00 | 3.00 | 3.00 | 3.00 | 3.00 |
| | Coco-Caprylate | 1.00 | 1.00 | 1.00 | 1.00 | 1.00 | 1.00 | 1.00 | 1.00 | 1.00 |
| | Dibutyl adipate | 2.00 | 2.00 | 2.00 | 2.00 | 2.00 | 2.00 | 2.00 | 2.00 | 2.00 |
| | PPG-2 Myristyl Ether Propionate | 2.00 | 2.00 | 2.00 | 2.00 | 2.00 | 2.00 | 2.00 | 2.00 | 2.00 |
| Part B | Water | Qs to 100 | Qs to 100 | Qs to 100 | Qs to 100 | Qs to 100 | Qs to 100 | Qs to 100 | Qs to 100 | Qs to 100 |
| | PVP/dimethylconylacrylate/polycarbamyl/polyglycol ester | 3.00 | 3.00 | 3.00 | 3.00 | 3.00 | 3.00 | 3.00 | 3.00 | 3.00 |
| | Disodium EDTA | 0.20 | 0.20 | 0.20 | 0.20 | 0.20 | 0.20 | 0.20 | 0.20 | 0.20 |
| | Sclerotium Gum | 2.00 | 2.00 | 2.00 | 2.00 | 2.00 | 2.00 | 2.00 | 2.00 | 2.00 |
| | Ammonium Acryldimethyltaurate/Beneth-25 Methacrylate Crosspolymer. | 0.50 | 0.50 | 0.50 | 0.50 | 0.50 | 0.50 | 0.50 | 0.50 | 0.50 |

| Example B4: Sun Cream | | | | | | | | | | |
|---|---|---|---|---|---|---|---|---|---|---|
| | INCI-Name | 4A % w/w | 4B % w/w | 4C % w/w | 4D % w/w | 4E % w/w | 4F % w/w | 4G % w/w | 4H % w/w | 4I % w/w |
| Part C | Cyclopentasiloxane (and) cyclohexasiloxane | 4.00 | 4.00 | 4.00 | 4.00 | 4.00 | 4.00 | 4.00 | 4.00 | 4.00 |
| | Phenoxyethanol (and) Methylparaben (and) Ethylparaben (and) Butylparaben (and) Propylparaben (and) Isobutylparaben | 1.00 | 1.00 | 1.00 | 1.00 | 1.00 | 1.00 | 1.00 | 1.00 | 1.00 |
| | Sodium Hydroxide (and) Water | Qsp | Qsp | Qsp | Qsp | Qsp | Qsp | Qsp | Qsp | Qsp |
| | Diethylamino Hydroxy Benzoyl Hexyl Benzoate | | | | | | | | | 2.00 |
| | Ethylhexyl Triazone | 2.00 | | | | | | 2.00 | 2.00 | 2.00 |
| | BBDAPT (CAS Nb: 207562-42-3) | | 2.00 | | | | | | | |
| | Ethylhexyl Methoxycinnamate | 7.00 | 7.00 | | | | | | | |
| | Bis-Ethylhexyloxyphenol Methoxyphenyl Triazine | | 2.00 | | 2.00 | | 2.00 | 2.00 | | 2.00 |
| | Methylene Bis-Benzotriazolyl Tetramethylbutylphenol * | 3.00 | 3.00 | | | 3.00 | 3.00 | | 3.00 | 3.00 |
| | MBM-09 | | 10.00 | 10.00 | 10.00 | 10.00 | 10.00 | 10.00 | 10.00 | 10.00 |
| | Bis-Ethylhexyloxyphenol Methoxyphenyl Triazine ** | 2.00 | 2.00 | 2.00 | 2.00 | 2.00 | 2.00 | 2.00 | 2.00 | 2.00 |
| | Phenylene Bis-Diphenyltriazine * | 6.00 | 3.00 | 4.00 | 5.00 | 2.00 | 3.00 | 5.00 | 6.00 | 2.00 |

| Example B5: Daily Care with UV Protection | | | | | | | | | | |
|---|---|---|---|---|---|---|---|---|---|---|
| | INCI-Name | 5A % w/w | 5B % w/w | 5C % w/w | 5D % w/w | 5E % w/w | 5F % w/w | 5G % w/w | 5H % w/w | 5I % w/w |
| Part A | Glyceryl Stearate | 3.00 | 3.00 | 3.00 | 3.00 | 3.00 | 3.00 | 3.00 | 3.00 | 3.00 |
| | Glyceryl Stearate (and) PEG-100 Stearate | 3.50 | 3.50 | 3.50 | 3.50 | 3.50 | 3.50 | 3.50 | 3.50 | 3.50 |
| | C12-15 Alkyl Benzoate | 4.00 | 4.00 | 4.00 | 4.00 | 4.00 | 4.00 | 4.00 | 4.00 | 4.00 |
| | Triisodecyl Trimellitate | 3.00 | 3.00 | 3.00 | 3.00 | 3.00 | 3.00 | 3.00 | 3.00 | 3.00 |
| | Dicaprylyl Carbonate | 1.00 | 1.00 | 1.00 | 1.00 | 1.00 | 1.00 | 1.00 | 1.00 | 1.00 |
| | Cetyl Alcohol | 1.50 | 1.50 | 1.50 | 1.50 | 1.50 | 1.50 | 1.50 | 1.50 | 1.50 |
| | Myristyl Myristate | 2.00 | 2.00 | 2.00 | 2.00 | 2.00 | 2.00 | 2.00 | 2.00 | 2.00 |
| | Isopropyl Palmitate | 2.00 | 2.00 | 2.00 | 2.00 | 2.00 | 2.00 | 2.00 | 2.00 | 2.00 |
| Part B | Aqua | qs to 100 | qs to 100 | qs to 100 | qs to 100 | qs to 100 | qs to 100 | qs to 100 | qs to 100 | qs to 100 |
| | Propylene Glycol | 7.50 | 7.50 | 7.50 | 7.50 | 7.50 | 7.50 | 7.50 | 7.50 | 7.50 |
| Part C | Phenoxyethanol (and) Methylparaben (and) Butylparaben (and) Ethylparaben (and) Propylparaben | 1.00 | 1.00 | 1.00 | 1.00 | 1.00 | 1.00 | 1.00 | 1.00 | 1.00 |
| | Sodium Acrylates Copolymer (and) Paraffinium Liquidum (and) PPG-1 Trideceth-6 | 2.00 | 2.00 | 2.00 | 2.00 | 2.00 | 2.00 | 2.00 | 2.00 | 2.00 |
| Part D | Citric Acid | Qsp | Qsp | Qsp | Qsp | Qsp | Qsp | Qsp | Qsp | Qsp |
| | Bis-Ethylhexyloxyphenol Methoxyphenyl Triazine | 2.00 | 2.00 | | | | 2.00 | | | |
| | Methylene Bis-Benzotriazolyl Tetramethylbutylphenol * | 3.00 | | 3.00 | | | | 3.00 | | |
| | Tris-Biphenyl Triazine * | 2.00 | | | 2.00 | | | | 2.00 | |
| | Methanone, 1,1'-(1,4-piperazinediyl)-bis[1-[2-[4-(diethylamino)-2-hydroxy-benzoyl]phenyl]- CAS number (919803-06-8) * | 2.00 | | | | 2.00 | | | | 2.00 |
| | Benzophenone-3 | 3.00 | | | | | 3.00 | 3.00 | 3.00 | 3.00 |
| | Homosalate | 10.00 | 10.00 | 10.00 | 10.00 | 10.00 | 10.00 | 10.00 | 10.00 | 10.00 |
| | Octocrylene | | 4.00 | 8.00 | 2.00 | 8.00 | 8.00 | 8.00 | | |
| | MBM-09 | 6.00 | | | 4.00 | | | | 6.00 | 6.00 |
| | Ethylhexyl Salicylate | 5.00 | 5.00 | 5.00 | 5.00 | 5.00 | 5.00 | 5.00 | 5.00 | 5.00 |
| | Butyl Methoxydibenzoylmethane | | | | | | | | | 1.00 |
| | BBDAPT (CAS Nb: 207562-42-3) | | 2.00 | | | | | | | |
| | Phenylene Bis-Diphenyltriazine * | 2.00 | 2.00 | 6.00 | 2.00 | 5.00 | 4.00 | 2.00 | 3.00 | 5.00 |

O/W Formulation
Gel

| | Example B6: Sunscreen Gel | | | | | | | | |
|---|---|---|---|---|---|---|---|---|---|
| INCI-Name | 6A % w/w | 6B % w/w | 6C % w/w | 6D % w/w | 6E % w/w | 6F % w/w | 6G % w/w | 6H % w/w | 6I % w/w |
| Alcohol Denatured | Qs to 100 | Qs to 100 | Qs to 100 | Qs to 100 | Qs to 100 | Qs to 100 | Qs to 100 | Qs to 100 | Qs to 100 |
| Dibutyl Adipate | 2.00 | 2.00 | 2.00 | 2.00 | 2.00 | 2.00 | 2.00 | 2.00 | 2.00 |
| Triisodecyl Trimellitate | 1.00 | 1.00 | 1.00 | 1.00 | 1.00 | 1.00 | 1.00 | 1.00 | 1.00 |
| Dicaprylyl Carbonate | 0.50 | 0.50 | 0.50 | 0.50 | 0.50 | 0.50 | 0.50 | 0.50 | 0.50 |
| Hydroxpropyl Cellulose | 1.00 | 1.00 | 1.00 | 1.00 | 1.00 | 1.00 | 1.00 | 1.00 | 1.00 |
| Acrylates/Octylacrylamide Copolymer | 1.00 | 1.00 | 1.00 | 1.00 | 1.00 | 1.00 | 1.00 | 1.00 | 1.00 |
| C12-15 Alkyl Benzoate | 10.00 | 10.00 | 10.00 | 10.00 | 10.00 | 10.00 | 10.00 | 10.00 | 10.00 |
| Cyclotetrasiloxane (and) Cyclopentasiloxane | 3.00 | 3.00 | 3.00 | 3.00 | 3.00 | 3.00 | 3.00 | 3.00 | 3.00 |
| PEG/PPG-4/12 Dimethicone | 1.00 | 1.00 | 1.00 | 1.00 | 1.00 | 1.00 | 1.00 | 1.00 | 1.00 |
| Diethylamino Hydroxy Benzoyl Hexyl Benzoate | 1.00 | 1.00 | 1.00 | 1.00 | 1.00 | 1.00 | 1.00 | 1.00 | 1.00 |
| Ethylhexyl Triazone | 2.00 | | 2.00 | | | | 2.00 | | 2.00 |
| BBDAPT (CAS Nb: 207562-42-3) | | | | | 2.00 | | | | |
| Ethylhexyl Methoxycinnamate | | 7.00 | | 7.00 | | | | 4.00 | 2.00 |
| MBM-09 | | | | | | 14.00 | | 6.00 | 10.00 |
| Bis-Ethylhexyloxyphenol Methoxyphenyl Triazine | | | 2.00 | 2.00 | | | 2.00 | 2.00 | 2.00 |
| Methylene Bis-Benzotriazolyl Tetramethylbutylphenol * | | | | | 3.00 | 3.00 | 3.00 | 3.00 | |
| Tris-Biphenyl Triazine * | 2.00 | 2.00 | 2.00 | 2.00 | 2.00 | 2.00 | 2.00 | 2.00 | 2.00 |
| Phenylene Bis-Diphenyltriazine * | 2.00 | 2.00 | 8.00 | 3.00 | 5.00 | 2.00 | 1.00 | 8.00 | 6.00 |

| | Example B7: Clear Sunscreen Gel | | | | | | | | |
|---|---|---|---|---|---|---|---|---|---|
| INCI-Name | 7A % w/w | 7B % w/w | 7C % w/w | 7D % w/w | 7E % w/w | 7F % w/w | 7G % w/w | 7H % w/w | 7I % w/w |
| SD Alcohol 40 | Qs to 100 | Qs to 100 | Qs to 100 | Qs to 100 | Qs to 100 | Qs to 100 | Qs to 100 | Qs to 100 | Qs to 100 |
| Dibutyl Adipate | 4.00 | 4.00 | 4.00 | 4.00 | 4.00 | 4.00 | 4.00 | 4.00 | 4.00 |
| Tridecyl Trimellitate | 1.00 | 1.00 | 1.00 | 1.00 | 1.00 | 1.00 | 1.00 | 1.00 | 1.00 |
| Dicaprylyl Carbonate | 1.00 | 1.00 | 1.00 | 1.00 | 1.00 | 1.00 | 1.00 | 1.00 | 1.00 |
| Hydroxypropyl Cellulose | 1.70 | 1.70 | 1.70 | 1.70 | 1.70 | 1.70 | 1.70 | 1.70 | 1.70 |
| Isopropyl PPG-2 Isodeceth-7 Carboxylate | 9.70 | 9.70 | 9.70 | 9.70 | 9.70 | 9.70 | 9.70 | 9.70 | 9.70 |
| SD Alcohol 40 | 24.00 | 24.00 | 24.00 | 24.00 | 24.00 | 24.00 | 24.00 | 24.00 | 24.00 |
| Fragrance | 0.60 | 0.60 | 0.60 | 0.60 | 0.60 | 0.60 | 0.60 | 0.60 | 0.60 |
| Aqua | 8.00 | 8.00 | 8.00 | 8.00 | 8.00 | 8.00 | 8.00 | 8.00 | 8.00 |
| Diethylamino Hydroxy Benzoyl Hexyl Benzoate | 1.00 | 1.00 | 1.00 | 1.00 | 1.00 | 1.00 | 1.00 | 2.00 | 3.00 |
| Ethylhexyl Triazone | 2.00 | 2.00 | | | | | | 2.00 | 2.00 |
| BBDAPT (CAS Nb: 207562-42-3) | | | | | | | 2.00 | | |
| Ethylhexyl Methoxycinnamate | 7.00 | 7.00 | | | | | | | |
| Bis-Ethylhexyloxyphenol Methoxyphenyl Triazine | | 2.00 | | 2.00 | | 2.00 | 2.00 | | 2.00 |
| Methylene Bis-Benzotriazolyl Tetramethylbutylphenol * | 3.00 | 3.00 | | | 3.00 | 3.00 | | 3.00 | 3.00 |
| MBM-09 | | | 10.00 | 10.00 | 10.00 | 10.00 | 10.00 | 10.00 | 10.00 |
| Tris-Biphenyl Triazine * | 2.00 | 2.00 | 2.00 | 2.00 | 2.00 | 2.00 | 2.00 | 2.00 | 2.00 |
| Phenylene Bis-Diphenyltriazine * | 5.00 | 1.00 | 2.00 | 3.00 | 1.00 | 8.00 | 6.00 | 3.00 | 3.00 |

O/W formulation
Emulsifier Free

Example B8: Emulsifier free

| INCI-Name | 8A % w/w | 8B % w/w | 8C % w/w | 8D % w/w | 8E % w/w | 8F % w/w | 8G % w/w | 8H % w/w | 8I % w/w |
|---|---|---|---|---|---|---|---|---|---|
| Ceteareth-20 | 1.00 | 1.00 | 1.00 | 1.00 | 1.00 | 1.00 | 1.00 | 1.00 | 1.00 |
| Xanthan Gum | 0.50 | 0.50 | 0.50 | 0.50 | 0.50 | 0.50 | 0.50 | 0.50 | 0.50 |
| Dicaprylyl Carbonate | 4.00 | 4.00 | 4.00 | 4.00 | 4.00 | 4.00 | 4.00 | 4.00 | 4.00 |
| Triisodecyl Trimellitate | 2.00 | 2.00 | 2.00 | 2.00 | 2.00 | 2.00 | 2.00 | 2.00 | 2.00 |
| Tridecyl Trimellitate | 1.00 | 1.00 | 1.00 | 1.00 | 1.00 | 1.00 | 1.00 | 1.00 | 1.00 |
| Dibutyl Adipate | 1.00 | 1.00 | 1.00 | 1.00 | 1.00 | 1.00 | 1.00 | 1.00 | 1.00 |
| C12-15 Alkyl Benzoate | 1.00 | 1.00 | 1.00 | 1.00 | 1.00 | 1.00 | 1.00 | 1.00 | 1.00 |
| Butylene Glycol Dicaprylate/Dicaprate | 2.00 | 2.00 | 2.00 | 2.00 | 2.00 | 2.00 | 2.00 | 2.00 | 2.00 |
| Cyclomethicone | 3.00 | 3.00 | 3.00 | 3.00 | 3.00 | 3.00 | 3.00 | 3.00 | 3.00 |
| VP/Hexadecene Copolymer | 0.50 | 0.50 | 0.50 | 0.50 | 0.50 | 0.50 | 0.50 | 0.50 | 0.50 |
| Glycerin | 3.00 | 3.00 | 3.00 | 3.00 | 3.00 | 3.00 | 3.00 | 3.00 | 3.00 |
| Vitamin E Acetate | 0.50 | 0.50 | 0.50 | 0.50 | 0.50 | 0.50 | 0.50 | 0.50 | 0.50 |
| PETP | 0.40 | 0.40 | 0.40 | 0.40 | 0.40 | 0.40 | 0.40 | 0.40 | 0.40 |
| Butylene Glycol (and) Iodopropynyl Butylcarbamate | 0.20 | 0.20 | 0.20 | 0.20 | 0.20 | 0.20 | 0.20 | 0.20 | 0.20 |
| Methylparaben | 0.50 | 0.50 | 0.50 | 0.50 | 0.50 | 0.50 | 0.50 | 0.50 | 0.50 |
| Phenoxyethanol | 0.50 | 0.50 | 0.50 | 0.50 | 0.50 | 0.50 | 0.50 | 0.50 | 0.50 |
| Ethanol | 3.00 | 3.00 | 3.00 | 3.00 | 3.00 | 3.00 | 3.00 | 3.00 | 3.00 |
| Parfume | 0.20 | 0.20 | 0.20 | 0.20 | 0.20 | 0.20 | 0.20 | 0.20 | 0.20 |
| Aqua | ad 100 | ad 100 | ad 100 | ad 100 | ad 100 | ad 100 | ad 100 | ad 100 | ad 100 |
| Diethylamino Hydroxy Benzoyl Hexyl Benzoate | 1.00 | | | | | | | | |
| Ethylhexyl Triazone | 2.00 | | 2.00 | | 2.00 | | 2.00 | | |
| BBDAPT (CAS Nb: 207562-42-3) | | | | | | | | | 2.00 |
| Ethylhexyl Methoxycinnamate | | | | 7.00 | | | | 7.00 | 7.00 |
| MBM-09 | | 14.00 | | | | 14.00 | | | |
| Bis-Ethylhexyloxyphenol Methoxyphenyl Triazine | | | 2.00 | 2.00 | | | 2.00 | 2.00 | 2.00 |
| Methylene Bis-Benzotriazolyl Tetramethylbutylphenol * | | | | | 3.00 | 3.00 | 3.00 | 3.00 | |
| Methanone, 1,1'-(1,4-piperazine-diyl)bis[1-[2-[4-(diethylamino)-2-hydroxybenzoyl]phenyl]- CAS number (919803-06-8) * | 2.00 | 2.00 | 2.00 | 2.00 | 2.00 | 2.00 | 2.00 | 2.00 | 2.00 |
| Phenylene Bis-Diphenyltriazine * | | 3.00 | 3.00 | 2.00 | 4.00 | 6.00 | 8.00 | 1.00 | 3.00 |

Example B9: Emulsifier free

| INCI-Name | 9A % w/w | 9B % w/w | 9C % w/w | 9D % w/w | 9E % w/w | 9F % w/w | 9G % w/w | 9H % w/w | 9I % w/w |
|---|---|---|---|---|---|---|---|---|---|
| Sodium Carbomer | 0.20 | 0.20 | 0.20 | 0.20 | 0.20 | 0.20 | 0.20 | 0.20 | 0.20 |
| Xanthan Gum | 0.30 | 0.30 | 0.30 | 0.30 | 0.30 | 0.30 | 0.30 | 0.30 | 0.30 |
| Dibutyl Adipate | 4.00 | 4.00 | 4.00 | 4.00 | 4.00 | 4.00 | 4.00 | 4.00 | 4.00 |
| Tridecyl Trimellitate | 2.00 | 2.00 | 2.00 | 2.00 | 2.00 | 2.00 | 2.00 | 2.00 | 2.00 |
| Coco-Caprylate | 1.00 | 1.00 | 1.00 | 1.00 | 1.00 | 1.00 | 1.00 | 1.00 | 1.00 |
| C12-15 Alkyl Benzoate | 1.00 | 1.00 | 1.00 | 1.00 | 1.00 | 1.00 | 1.00 | 1.00 | 1.00 |
| Dicaprylyl Carbonate | 1.00 | 1.00 | 1.00 | 1.00 | 1.00 | 1.00 | 1.00 | 1.00 | 1.00 |
| Dimethicone | 0.50 | 0.50 | 0.50 | 0.50 | 0.50 | 0.50 | 0.50 | 0.50 | 0.50 |
| Shea Butter | 2.00 | 2.00 | 2.00 | 2.00 | 2.00 | 2.00 | 2.00 | 2.00 | 2.00 |
| EthylhexyloxyGlycerin | 0.50 | 0.50 | 0.50 | 0.50 | 0.50 | 0.50 | 0.50 | 0.50 | 0.50 |
| Glycerin | 7.50 | 7.50 | 7.50 | 7.50 | 7.50 | 7.50 | 7.50 | 7.50 | 7.50 |
| *Glycine Soja* | 1.50 | 1.50 | 1.50 | 1.50 | 1.50 | 1.50 | 1.50 | 1.50 | 1.50 |
| Vitamin E Acetate | 0.20 | 0.20 | 0.20 | 0.20 | 0.20 | 0.20 | 0.20 | 0.20 | 0.20 |
| α-Glycosil Rutin | 0.30 | 0.30 | 0.30 | 0.30 | 0.30 | 0.30 | 0.30 | 0.30 | 0.30 |
| PETP | 0.50 | 0.50 | 0.50 | 0.50 | 0.50 | 0.50 | 0.50 | 0.50 | 0.50 |
| Trisodium EDTA | 0.30 | 0.30 | 0.30 | 0.30 | 0.30 | 0.30 | 0.30 | 0.30 | 0.30 |
| Ethanol | 7.00 | 7.00 | 7.00 | 7.00 | 7.00 | 7.00 | 7.00 | 7.00 | 7.00 |
| Aqua | ad 100 | ad 100 | ad 100 | ad 100 | ad 100 | ad 100 | ad 100 | ad 100 | ad 100 |
| Diethylamino Hydroxy Benzoyl Hexyl Benzoate | 2.00 | 2.00 | 2.00 | 2.00 | 2.00 | 1.00 | 2.00 | 2.00 | |
| Ethylhexyl Triazone | | 2.00 | | | | | 2.00 | 2.00 | 2.00 |
| BBDAPT (Cas Nb: 207562-42-3) | 2.00 | | | | | | | | |
| Ethylhexyl Methoxycinnamate | 7.00 | 7.00 | | | | | | | |

Example B9: Emulsifier free

| INCI-Name | 9A % w/w | 9B % w/w | 9C % w/w | 9D % w/w | 9E % w/w | 9F % w/w | 9G % w/w | 9H % w/w | 9I % w/w |
|---|---|---|---|---|---|---|---|---|---|
| Bis-Ethylhexyloxyphenol Methoxyphenyl Triazine | | 2.00 | | 2.00 | | 2.00 | 2.00 | | 2.00 |
| Methylene Bis-Benzotriazolyl Tetramethylbutylphenol * | 3.00 | 3.00 | | | 3.00 | 3.00 | | 3.00 | 3.00 |
| MBM-09 | | | 10.00 | 10.00 | 10.00 | 10.00 | 10.00 | 10.00 | 10.00 |
| Methanone, 1,1'-(1,4-piperazine-diyl)bis[1-[2-[4-(diethylamino)-2-hydroxybenzoyl]phenyl]- CAS number (919803-06-8) * | 2.00 | 2.00 | 2.00 | 2.00 | 2.00 | 2.00 | 2.00 | 2.00 | 2.00 |
| Phenylene Bis-Diphenyltriazine * | 1.00 | 3.00 | 5.00 | 7.00 | 4.00 | 2.00 | 2.00 | 1.00 | 5.00 |

Spray Formulation
Classic

Example B10: Sun spray

| | INCI-Name | 10A % w/w | 10B % w/w | 10C % w/w | 10D % w/w | 10E % w/w | 10F % w/w | 10G % w/w | 10H % w/w | 10I % w/w |
|---|---|---|---|---|---|---|---|---|---|---|
| Part A | Butylene Glycol Dicaprylate/Dicaprate | 10.00 | 10.00 | 10.00 | 10.00 | 10.00 | 10.00 | 10.00 | 10.00 | 10.00 |
| | C18-36 Acid Triglyceride | 0.70 | 0.70 | 0.70 | 0.70 | 0.70 | 0.70 | 0.70 | 0.70 | 0.70 |
| | Ceteareth-20 | 0.60 | 0.60 | 0.60 | 0.60 | 0.60 | 0.60 | 0.60 | 0.60 | 0.60 |
| | Dibutyl Adipate | 4.00 | 4.00 | 4.00 | 4.00 | 4.00 | 4.00 | 4.00 | 4.00 | 4.00 |
| | Triisodecyl Trimellitate | 2.00 | 2.00 | 2.00 | 2.00 | 2.00 | 2.00 | 2.00 | 2.00 | 2.00 |
| | Dicaprylyl Carbonate | 1.00 | 1.00 | 1.00 | 1.00 | 1.00 | 1.00 | 1.00 | 1.00 | 1.00 |
| | C12-15 Alkyl Benzoate | 6.00 | 6.00 | 6.00 | 6.00 | 6.00 | 6.00 | 6.00 | 6.00 | 6.00 |
| | Taurine | 0.40 | 0.40 | 0.40 | 0.40 | 0.40 | 0.40 | 0.40 | 0.40 | 0.40 |
| | VP/Hexadecene Copolymer | 0.50 | 0.50 | 0.50 | 0.50 | 0.50 | 0.50 | 0.50 | 0.50 | 0.50 |
| Part B | Aqua | Qs to 100 | Qs to 100 | Qs to 100 | Qs to 100 | Qs to 100 | Qs to 100 | Qs to 100 | Qs to 100 | Qs to 100 |
| | Glycerin | 6.00 | 6.00 | 6.00 | 6.00 | 6.00 | 6.00 | 6.00 | 6.00 | 6.00 |
| | Methylpropanediol | 1.00 | 1.00 | 1.00 | 1.00 | 1.00 | 1.00 | 1.00 | 1.00 | 1.00 |
| | Acrylates/C10-30 Alkyl Acrylate Crosspolymer | | | | | 0.18 | 0.18 | 0.18 | 0.18 | 0.18 |
| | Acrylates/10-30 Alkyl Methacrylate Copolymer | 0.18 | 0.18 | 0.18 | 0.18 | | | | | |
| | Trisodium EDTA | 0.10 | 0.10 | 0.10 | 0.10 | 0.10 | 0.10 | 0.10 | 0.10 | 0.10 |
| Part C | Alcohol Denatured | 4.00 | 4.00 | 4.00 | 4.00 | 4.00 | 4.00 | 4.00 | 4.00 | 4.00 |
| | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.50 | 0.50 | 0.50 | 0.50 | 0.50 | 0.50 | 0.50 | 0.50 | 0.50 |
| | Diethylamino Hydroxy Benzoyl Hexyl Benzoate | 1.00 | 1.00 | 1.00 | 2.00 | 2.00 | 1.00 | 1.00 | 2.00 | |
| | Ethylhexyl Triazone | 1.00 | 2.00 | | | | | | 2.00 | 2.00 |
| | BBDAPT (CAS Nb: 207562-42-3) | | | | | | | 2.00 | | |
| | Ethylhexyl Methoxycinnamate | 2.00 | 2.00 | | | | | | | |
| | Bis-Ethylhexyloxyphenol Methoxyphenyl Triazine | | 2.00 | | 2.00 | | 2.00 | 2.00 | | 1.00 |
| | Methylene Bis-Benzotriazolyl Tetramethylbutylphenol * | 2.00 | 2.00 | | | 3.00 | 3.00 | | 3.00 | 2.00 |
| | MBM-09 | | | 10.00 | 10.00 | 10.00 | 10.00 | 10.00 | 5.00 | 5.00 |
| | Bis-Ethylhexyloxyphenol Methoxyphenyl Triazine ** | 2.00 | 2.00 | 2.00 | 2.00 | 2.00 | 2.00 | 2.00 | 2.00 | 2.00 |
| | Tris-Biphenyl Triazine * | 2.00 | 2.00 | 2.00 | 2.00 | 2.00 | 2.00 | 2.00 | 2.00 | 2.00 |
| | Methanone, 1,1'-(1,4-piperazinediyl)bis[1-[2-[4-(diethylamino)-2-hydroxybenzoyl]phenyl]- CAS number (919803-06-8) * | 2.00 | 2.00 | 2.00 | 2.00 | 2.00 | 2.00 | 2.00 | 2.00 | 2.00 |
| | Phenylene Bis-Diphenyltriazine * | 1.00 | 1.00 | 1.00 | 3.00 | 4.00 | 1.00 | 1.00 | 2.00 | 4.00 |

Spray Formulation
Foaming

| | | Example 11: Sun spray foaming | | | | | | | | |
|---|---|---|---|---|---|---|---|---|---|---|
| | INCI-Name | 11A % w/w | 11B % w/w | 11C % w/w | 11D % w/w | 11E % w/w | 11F % w/w | 11G % w/w | 11H % w/w | 11I % w/w |
| Part A | Behenyl Alcohol (and) Glyceryl Stearate (and) Glyceryl Stearate Citrate (and) Disodium Ethylene Dicocamide PEG-15 Disulfate | 0.50 | 0.50 | 0.50 | 0.50 | 0.50 | 0.50 | 0.50 | 0.50 | 0.50 |
| | Isotrideceth-12 | 0.50 | 0.50 | 0.50 | 0.50 | 0.50 | 0.50 | 0.50 | 0.50 | 0.50 |
| | Ethylhexyl Salicylate | 4.00 | 4.00 | 4.00 | 4.00 | 4.00 | 4.00 | 4.00 | 4.00 | 4.00 |
| | Hydrogenated Coco-glycerides | 1.50 | 1.50 | 1.50 | 1.50 | 1.50 | 1.50 | 1.50 | 1.50 | 1.50 |
| | C12-15 Alkyl Benzoate | 8.00 | 8.00 | 8.00 | 8.00 | 8.00 | 8.00 | 8.00 | 8.00 | 8.00 |
| Part B | Aqua | 5.00 | 5.00 | 5.00 | 5.00 | 5.00 | 5.00 | 5.00 | 5.00 | 5.00 |
| | Glycerin | 4.00 | 4.00 | 4.00 | 4.00 | 4.00 | 4.00 | 4.00 | 4.00 | 4.00 |
| | Galactoarabinan | 0.25 | 0.25 | 0.25 | 0.25 | 0.25 | 0.25 | 0.25 | 0.25 | 0.25 |
| Part C | Disodium Ethylene Dicocamide PEG-15 Disulfate (and) Sodium Lauroyl Lactylate | 1.00 | 1.00 | 1.00 | 1.00 | 1.00 | 1.00 | 1.00 | 1.00 | 1.00 |
| | Water | Qs to 100 | Qs to 100 | Qs to 100 | Qs to 100 | Qs to 100 | Qs to 100 | Qs to 100 | Qs to 100 | Qs to 100 |
| Part D | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.60 | 0.60 | 0.60 | 0.60 | 0.60 | 0.60 | 0.60 | 0.60 | 0.60 |
| | Diethylamino Hydroxy Benzoyl Hexyl Benzoate | 2.00 | 2.00 | 0.00 | 0.00 | 0.00 | 0.00 | 0.00 | 2.00 | 0.00 |
| | Ethylhexyl Triazone | 2.00 | | 2.00 | | | | 2.00 | | 2.00 |
| | BBDAPT (CAS Nb: 207562-42-3) | | | | | 2.00 | | | | |
| | Ethylhexyl Methoxycinnamate | | 7.00 | | 7.00 | | 7.00 | | | |
| | MBM-09 | | | | | | | | 14.00 | 14.00 |
| | Bis-Ethylhexyloxyphenol Methoxyphenyl Triazine | | | 2.00 | 2.00 | | | 2.00 | 2.00 | 2.00 |
| | Methylene Bis-Benzotriazolyl Tetramethylbutylphenol * | | | | | 3.00 | 3.00 | 3.00 | 4.00 | |
| | Titanium Dioxide *** | 2.00 | 2.00 | 2.00 | 2.00 | 2.00 | 2.00 | 2.00 | 2.00 | 2.00 |
| | Phenylene Bis-Diphenyltriazine * | 2.00 | 1.00 | 2.00 | 6.00 | 1.00 | 3.00 | 2.00 | 8.00 | 2.00 |

Spray Formulation
Continuous

| | Example B12: Continuous Spray Fresh Cooling | | | | | | | | |
|---|---|---|---|---|---|---|---|---|---|
| INCI-Name | 12A % w/w | 12B % w/w | 12C % w/w | 12D % w/w | 12E % w/w | 12F % w/w | 12G % w/w | 12H % w/w | 12I % w/w |
| SD-Alcohol 40 | 58.00 | 58.00 | 58.00 | 58.00 | 58.00 | 58.00 | 58.00 | 58.00 | 58.00 |
| Diethylhexyl 2,6-Naphthalate | 6.00 | 6.00 | 6.00 | 6.00 | 6.00 | 6.00 | 6.00 | 6.00 | 6.00 |
| Trisiloxane (and) Dimethicone | 4.00 | 4.00 | 4.00 | 4.00 | 4.00 | 4.00 | 4.00 | 4.00 | 4.00 |
| Acrylates/Octylacrylamide Copolymer | 3.00 | 3.00 | 3.00 | 3.00 | 3.00 | 3.00 | 3.00 | 3.00 | 3.00 |
| PPG-5-Ceteth-20 | 2.00 | 2.00 | 2.00 | 2.00 | 2.00 | 2.00 | 2.00 | 2.00 | 2.00 |
| Tocopherol Acetate | 1.00 | 1.00 | 1.00 | 1.00 | 1.00 | 1.00 | 1.00 | 1.00 | 1.00 |
| Ascorbyl Palmitate | 0.3 | 0.3 | 0.3 | 0.3 | 0.3 | 0.3 | 0.3 | 0.3 | 0.3 |
| Retinyl Palmitate | 0.3 | 0.3 | 0.3 | 0.3 | 0.3 | 0.3 | 0.3 | 0.3 | 0.3 |
| Cyclopentasiloxane (and) Acrylates/Dimethicone Copolymer | 1.00 | 1.00 | 1.00 | 1.00 | 1.00 | 1.00 | 1.00 | 1.00 | 1.00 |
| Propylene Glycol (and) Ethoxydiglycol (and) Menthyl PCA (and) Lauryl PCA | 1.50 | 1.50 | 1.50 | 1.50 | 1.50 | 1.50 | 1.50 | 1.50 | 1.50 |
| Parfume | q.s. | q.s. | q.s. | q.s. | q.s. | q.s. | q.s. | q.s. | q.s. |
| Aqua | ad 100 | ad 100 | ad 100 | ad 100 | ad 100 | ad 100 | ad 100 | ad 100 | ad 100 |
| Propellent | Qs | Qs | Qs | Qs | Qs | Qs | Qs | Qs | Qs |
| Diethylamino Hydroxy Benzoyl Hexyl Benzoate | | | | | 2.00 | | | | |
| Ethylhexyl Triazone | | 2.00 | | | | | | 2.00 | 2.00 | 2.00 |
| BBDAPT (CAS Nb: 207562-42-3) | 2.00 | | | | | | | | |
| Ethylhexyl Methoxycinnamate | 4.00 | 7.00 | | | | | | | |

-continued

| | Example B12: Continuous Spray Fresh Cooling | | | | | | | | |
|---|---|---|---|---|---|---|---|---|---|
| INCI-Name | 12A % w/w | 12B % w/w | 12C % w/w | 12D % w/w | 12E % w/w | 12F % w/w | 12G % w/w | 12H % w/w | 12I % w/w |
| Bis-Ethylhexyloxyphenol Methoxyphenyl Triazine | | 2.00 | | 2.00 | | 2.00 | 2.00 | | 2.00 |
| Methylene Bis-Benzotriazolyl Tetramethylbutylphenol * | 3.00 | 3.00 | | | 3.00 | 3.00 | | 3.00 | 3.00 |
| MBM-09 | | | 10.00 | 10.00 | 8.00 | 10.00 | 10.00 | 10.00 | 10.00 |
| Titanium Dioxide *** | 2.00 | 2.00 | 2.00 | 2.00 | 2.00 | 2.00 | 2.00 | 2.00 | 2.00 |
| Phenylene Bis-Diphenyltriazine * | 1.00 | 4.00 | 3.00 | 6.00 | 2.00 | 6.00 | 1.00 | 6.00 | 2.00 |

W/O Formulation

| | | Example B13: Sunmilk for highly sensitive skins | | | | | | | | |
|---|---|---|---|---|---|---|---|---|---|---|
| | INCI-Name | 13A % w/w | 13B % w/w | 13C % w/w | 13D % w/w | 13E % w/w | 13F % w/w | 13G % w/w | 13H % w/w | 13I % w/w |
| Part A | C12-15 Alky Benzoate | 3.50 | 3.50 | 3.50 | 3.50 | 3.50 | 3.50 | 3.50 | 3.50 | 3.50 |
| | Cyclopentasiloxane (and) Cyclohexasiloxane | 9.00 | 9.00 | 9.00 | 9.00 | 9.00 | 9.00 | 9.00 | 9.00 | 9.00 |
| | Isododecane | 4.50 | 4.50 | 4.50 | 4.50 | 4.50 | 4.50 | 4.50 | 4.50 | 4.50 |
| | PEG-30 Dipolyhydroxystearate | 3.00 | 3.00 | 3.00 | 3.00 | 3.00 | 3.00 | 3.00 | 3.00 | 3.00 |
| | PEG-45/Dodecyl Glycol Copolymer | 1.00 | 1.00 | 1.00 | 1.00 | 1.00 | 1.00 | 1.00 | 1.00 | 1.00 |
| | Hydrogenated Castor Oil | 1.50 | 1.50 | 1.50 | 1.50 | 1.50 | 1.50 | 1.50 | 1.50 | 1.50 |
| | Tribehenin | 0.40 | 0.40 | 0.40 | 0.40 | 0.40 | 0.40 | 0.40 | 0.40 | 0.40 |
| | Disteardimonium Hectorite | 0.60 | 0.60 | 0.60 | 0.60 | 0.60 | 0.60 | 0.60 | 0.60 | 0.60 |
| Part B | Aqua | Qs to 100 | Qs to 100 | Qs to 100 | Qs to 100 | Qs to 100 | Qs to 100 | Qs to 100 | Qs to 100 | Qs to 100 |
| | Glycerin | 10.00 | 10.00 | 10.00 | 10.00 | 10.00 | 10.00 | 10.00 | 10.00 | 10.00 |
| Part C | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.50 | 0.50 | 0.50 | 0.50 | 0.50 | 0.50 | 0.50 | 0.50 | 0.50 |
| | Silica Dimethyl Silylate | 0.60 | 0.60 | 0.60 | 0.60 | 0.60 | 0.60 | 0.60 | 0.60 | 0.60 |
| | Ethylhexyl Triazone | 1.00 | | 2.00 | | 2.00 | | 2.00 | | |
| | BBDAPT (CAS Nb: 207562-42-3) | 1.00 | | | | | | | | |
| | Bis-Ethylhexyloxyphenol Methoxyphenyl Triazine | 1.00 | 1.00 | 1.00 | 1.00 | 2.00 | 2.00 | 1.00 | 1.00 | 2.00 |
| | Methylene Bis-Benzotriazolyl Tetramethylbutylphenol * | 3.00 | 3.00 | 4.00 | 3.00 | 3.00 | 3.00 | 3.00 | 3.00 | 3.00 |
| | Bis-Ethylhexyloxyphenol Methoxyphenyl Triazine ** | 1.00 | 1.00 | 1.00 | 1.00 | | | 1.00 | 1.00 | |
| | Tris-Biphenyl Triazine * | 1.00 | 1.00 | 2.00 | | | | | | |
| | Methanone, 1,1'-(1,4-piperazinediyl)bis[1-[2-[4-(diethylamino)-2-hydroxybenzoyl]phenyl]- CAS number (919803-06-8) * | 1.00 | 1.00 | 2.00 | 1.00 | 1.00 | 1.00 | 1.00 | 1.00 | |
| | Butyl Methoxydibenzoylmethane | 1.00 | 1.00 | 1.00 | 1.00 | | | | 2.00 | 3.00 |
| | Octocrylene | | 8.00 | | 8.00 | | 8.00 | | 3.00 | |
| | MBM-09 | | | | | | | | | 6.00 |
| | Ethylhexyl Salicylate | | | 5.00 | 5.00 | | | | | 5.00 |
| | Diethylhexyl Butamido Triazone | | | | | 1.00 | 1.00 | | | 1.00 |
| | Phenylbenzimidazole Sulfonic Acid | | | | | | | 2.00 | 2.00 | 2.00 |
| | Phenylene Bis-Diphenyltriazine * | 2.00 | 2.00 | 5.00 | 1.00 | 2.00 | 2.00 | 1.00 | 1.00 | 6.00 |

| | INCI-Name | Example B14: Sun Milk W/O 14A % w/w | 14B % w/w | 14C % w/w | 14D % w/w | 14E % w/w | 14F % w/w | 14G % w/w | 14H % w/w | 14I % w/w |
|---|---|---|---|---|---|---|---|---|---|---|
| Part A | Butylen Glycol Dicaprylate/Dicaprate | 5.50 | 5.50 | 5.50 | 5.50 | 5.50 | 5.50 | 5.50 | 5.50 | 5.50 |
| | C18-36 Acid Triglyceride | 0.50 | 0.50 | 0.50 | 0.50 | 0.50 | 0.50 | 0.50 | 0.50 | 0.50 |
| | Isopropyl Stearate | 3.50 | 3.50 | 3.50 | 3.50 | 3.50 | 3.50 | 3.50 | 3.50 | 3.50 |
| | C12-15 Alkyl Benzoate | 8.00 | 8.00 | 8.00 | 8.00 | 8.00 | 8.00 | 8.00 | 8.00 | 8.00 |
| | Polyglyceryl-2 Dipolyhydroxystearate | 5.00 | 5.00 | 5.00 | 5.00 | 5.00 | 5.00 | 5.00 | 5.00 | 5.00 |
| | Diethylhexyl Butamido Triazone | 0.50 | 0.50 | 0.50 | 0.50 | 0.50 | 0.50 | 0.50 | 0.50 | 0.50 |
| | Cetyl Dimethicone | 0.50 | 0.50 | 0.50 | 0.50 | 0.50 | 0.50 | 0.50 | 0.50 | 0.50 |
| Part B | Aqua | Qs to 100 | Qs to 100 | Qs to 100 | Qs to 100 | Qs to 100 | Qs to 100 | Qs to 100 | Qs to 100 | Qs to 100 |
| | Butylene Glycol | 3.50 | 3.50 | 3.50 | 3.50 | 3.50 | 3.50 | 3.50 | 3.50 | 3.50 |
| | Glycerin | 3.50 | 3.50 | 3.50 | 3.50 | 3.50 | 3.50 | 3.50 | 3.50 | 3.50 |
| | Aluminum Starch Octenylsuccinate | 0.40 | 0.40 | 0.40 | 0.40 | 0.40 | 0.40 | 0.40 | 0.40 | 0.40 |
| | Magnesium Sulfate Heptahydrate | 0.30 | 0.30 | 0.30 | 0.30 | 0.30 | 0.30 | 0.30 | 0.30 | 0.30 |
| Part C | Alcohol Denatured | 3.00 | 3.00 | 3.00 | 3.00 | 3.00 | 3.00 | 3.00 | 3.00 | 3.00 |
| | BHT | 0.05 | 0.05 | 0.05 | 0.05 | 0.05 | 0.05 | 0.05 | 0.05 | 0.05 |
| | Phenoxyethanol (and) Methylparaben (and) Ethylparaben (and) Butylparaben (and) Propylparaben (and) Isobutylparaben | 0.50 | 0.50 | 0.50 | 0.50 | 0.50 | 0.50 | 0.50 | 0.50 | 0.50 |
| | Tocopheryl Acetate | 1.00 | 1.00 | 1.00 | 1.00 | 1.00 | 1.00 | 1.00 | 1.00 | 1.00 |
| | Diethylamino Hydroxy Benzoyl Hexyl Benzoate | | | | | 1.00 | 1.00 | 1.00 | | |
| | Ethylhexyl Triazone | 1.50 | 1.00 | | | | | 2.00 | 2.00 | 2.00 |
| | BBDAPT (CAS Nb: 207562-42-3) | | | | 2.00 | | | | | |
| | Ethylhexyl Methoxycinnamate | 4.00 | 1.00 | 1.00 | 3.00 | 6.00 | | | | |
| | Bis-Ethylhexyloxyphenol Methoxyphenyl Triazine | | 2.00 | | 1.00 | | 2.00 | 2.00 | | 2.00 |
| | Methylene Bis-Benzotriazolyl Tetramethylbutylphenol * | | | | | | | | | 2.00 |
| | MBM-09 | | | | | | 8.00 | 5.00 | 5.00 | |
| | Tris-Biphenyl Triazine * | 1.00 | 1.00 | 1.00 | 1.00 | 1.00 | 1.00 | 1.00 | 1.00 | |
| | Ethylhexyl Salicylate | 5.00 | | | | | | | | 5.00 |
| | Diethylhexyl Butamido Triazone | | 1.00 | | | | | | | 1.00 |
| | Phenylbenzimidazole Sulfonic Acid | | | 2.00 | | | | | | 2.00 |
| | Titanium Dioxide *** | | | | 2.00 | | | | | |
| | Homosalate | | | | | 10.00 | | | | 5.00 |
| | Phenylene Bis-Diphenyltriazine * | 4.00 | 3.00 | 2.00 | 3.00 | 3.00 | 1.00 | 3.00 | 4.00 | 4.00 |

W/Si Formulation

| | INCI-Name | Example B15: W/Si sun cream 15A % w/w | 15B % w/w | 15C % w/w | 15D % w/w | 15E % w/w | 15F % w/w | 15G % w/w | 15H % w/w | 15I % w/w |
|---|---|---|---|---|---|---|---|---|---|---|
| Part A | Cyclopentasiloxane (and) Dimethicone/Vinyl Dimethicone Crosspolymer | 3.00 | 3.00 | 3.00 | 3.00 | 3.00 | 3.00 | 3.00 | 3.00 | 3.00 |
| | PEG-10 Dimethicone | 0.30 | 0.30 | 0.30 | 0.30 | 0.30 | 0.30 | 0.30 | 0.30 | 0.30 |
| | Dimethicone (and) Dimethicone/PEG-10/15 Crosspolymer | 4.00 | 4.00 | 4.00 | 4.00 | 4.00 | 4.00 | 4.00 | 4.00 | 4.00 |
| | Dimethicone | 10.70 | 10.70 | 10.70 | 10.70 | 10.70 | 10.70 | 10.70 | 10.70 | 10.70 |
| Part B | 1,3-Butylen Glycol | 8.00 | 8.00 | 8.00 | 8.00 | 8.00 | 8.00 | 8.00 | 8.00 | 8.00 |
| | Sodium Citrate | 0.20 | 0.20 | 0.20 | 0.20 | 0.20 | 0.20 | 0.20 | 0.20 | 0.20 |
| | Ethyl Alcohol | 5.00 | 5.00 | 5.00 | 5.00 | 5.00 | 5.00 | 5.00 | 5.00 | 5.00 |
| | Sodium Chloride | 0.50 | 0.50 | 0.50 | 0.50 | 0.50 | 0.50 | 0.50 | 0.50 | 0.50 |
| | Aqua | Qs to 100 | Qs to 100 | Qs to 100 | Qs to 100 | Qs to 100 | Qs to 100 | Qs to 100 | Qs to 100 | Qs to 100 |
| | Diethylamino Hydroxy Benzoyl Hexyl Benzoate | | | | | | | 2.00 | | |
| | Ethylhexyl Triazone | 1.00 | | 1.00 | | 2.00 | | 2.00 | | 1.00 |
| | BBDAPT (CAS Nb: 207562-42-3) | | | | | | | | 2.00 | |

| | Example B15: W/Si sun cream | | | | | | | | |
|---|---|---|---|---|---|---|---|---|---|
| INCI-Name | 15A % w/w | 15B % w/w | 15C % w/w | 15D % w/w | 15E % w/w | 15F % w/w | 15G % w/w | 15H % w/w | 15I % w/w |
| Ethylhexyl Methoxycinnamate | | | | 3.00 | | | | 2.00 | 1.00 |
| MBM-09 | | 2.00 | | | | 8.00 | | 2.00 | |
| Bis-Ethylhexyloxyphenol Methoxyphenyl Triazine | | | 2.00 | 2.00 | | | 2.00 | 2.00 | 2.00 |
| Methylene Bis-Benzotriazolyl Tetramethylbutylphenol * | | | | | 3.00 | 3.50 | 3.00 | 3.00 | |
| Isoamyl p-Methoxycinnamate | 3.00 | 1.00 | 1.00 | 1.00 | 1.00 | 1.00 | 3.50 | 1.00 | 1.00 |
| 4-Methylbenzylidene Camphor | 1.00 | 1.00 | 1.00 | 1.00 | 1.00 | 1.00 | 1.00 | 1.00 | 1.00 |
| Polysilicone-15 | 2.00 | 1.00 | 1.00 | 1.00 | 1.00 | 1.00 | 2.00 | 1.00 | 1.00 |
| Disodium Phenyl Dibenzylmidazole Tetrasulfonate | 1.00 | 3.00 | 3.00 | 1.00 | 2.00 | 2.00 | 3.50 | 1.00 | 1.00 |
| Phenylene Bis-Diphenyltriazine * | 5.00 | 2.00 | 2.00 | 3.00 | 2.00 | 2.00 | 2.00 | 2.00 | 3.00 |

| | | Example B16: W/Si sun cream | | | | | | | | |
|---|---|---|---|---|---|---|---|---|---|---|
| | INCI-Name | 16A % w/w | 16B % w/w | 16C % w/w | 16D % w/w | 16E % w/w | 16F % w/w | 16G % w/w | 16H % w/w | 16I % w/w |
| Part A | Cyclopentasiloxane (and) PEG/PPG-18/18 Dimethicone | 10.00 | 10.00 | 10.00 | 10.00 | 10.00 | 10.00 | 10.00 | 10.00 | 10.00 |
| | Cyclomethicone | 9.00 | 9.00 | 9.00 | 9.00 | 9.00 | 9.00 | 9.00 | 9.00 | 9.00 |
| | Cyclomethicone (and) Trimethylsiloxysilicate | 3.50 | 3.50 | 3.50 | 3.50 | 3.50 | 3.50 | 3.50 | 3.50 | 3.50 |
| | Cyclopentasiloxane (and) Dimethicone Crosspolymer | 7.00 | 7.00 | 7.00 | 7.00 | 7.00 | 7.00 | 7.00 | 7.00 | 7.00 |
| Part B | Divinyldimethicone/Dimethicone Copolymer (and) C12-13 Pareth-23 (and) C12-13 Pareth-3 | 2.30 | 2.30 | 2.30 | 2.30 | 2.30 | 2.30 | 2.30 | 2.30 | 2.30 |
| | Sodium Chloride | 2.00 | 2.00 | 2.00 | 2.00 | 2.00 | 2.00 | 2.00 | 2.00 | 2.00 |
| | Aqua | Qs to 100 | Qs to 100 | Qs to 100 | Qs to 100 | Qs to 100 | Qs to 100 | Qs to 100 | Qs to 100 | Qs to 100 |
| | Merocyanine | 1.00 | 1.00 | 1.00 | 1.00 | 1.00 | 1.00 | 1.00 | 1.00 | 1.00 |
| | Diethylamino Hydroxy Benzoyl Hexyl Benzoate | 1.00 | | | | | | | | |
| | Ethylhexyl Triazone | 2.50 | | 2.50 | | 2.00 | | 2.00 | | 1.00 |
| | BBDAPT (CAS Nb: 207562-42-3) | | | | | | | | | 1.00 |
| | Ethylhexyl Methoxycinnamate | | | | 7.00 | | 7.00 | | 4.00 | |
| | Bis-Ethylhexyloxyphenol Methoxyphenyl Triazine | | | 2.00 | 2.00 | | | 2.00 | 2.00 | 2.00 |
| | MBM-09 | | 14.00 | | | | | | 8.00 | 10.00 |
| | Methylene Bis-Benzotriazolyl Tetramethylbutylphenol * | | | | | 3.00 | 3.00 | 3.00 | 3.00 | |
| | Phenylene Bis-Diphenyltriazine * | 1.00 | 1.00 | 2.00 | 4.00 | 2.00 | 1.00 | 1.00 | 3.00 | 3.00 |

Lipstick Formulation

| | Example B16: Lipstick | | | | | | | | |
|---|---|---|---|---|---|---|---|---|---|
| INCI-Name | 16A % w/w | 16B % w/w | 16C % w/w | 16D % w/w | 16E % w/w | 16F % w/w | 16G % w/w | 16H % w/w | 16I % w/w |
| Microcristallina Wax | 7.00 | 7.00 | 7.00 | 7.00 | 7.00 | 7.00 | 7.00 | 7.00 | 7.00 |
| Cera Carnauba | 2.50 | 2.50 | 2.50 | 2.50 | 2.50 | 2.50 | 2.50 | 2.50 | 2.50 |
| Candelilla Cera | 6.50 | 6.50 | 6.50 | 6.50 | 6.50 | 6.50 | 6.50 | 6.50 | 6.50 |
| Cetyl Alcohol | 1.50 | 1.50 | 1.50 | 1.50 | 1.50 | 1.50 | 1.50 | 1.50 | 1.50 |
| Lanolin Oil | 9.00 | 9.00 | 9.00 | 9.00 | 9.00 | 9.00 | 9.00 | 9.00 | 9.00 |
| Bis-Diglyceryl Polyacyladipate-2 | 4.00 | 4.00 | 4.00 | 4.00 | 4.00 | 4.00 | 4.00 | 4.00 | 4.00 |
| Avocado Oil | 5.00 | 5.00 | 5.00 | 5.00 | 5.00 | 5.00 | 5.00 | 5.00 | 5.00 |
| Pentaerythrityl Tetraisostearate | 2.00 | 2.00 | 2.00 | 2.00 | 2.00 | 2.00 | 2.00 | 2.00 | 2.00 |
| Myristyl Lactate | 6.00 | 6.00 | 6.00 | 6.00 | 6.00 | 6.00 | 6.00 | 6.00 | 6.00 |
| Jojoba Oil | 2.00 | 2.00 | 2.00 | 2.00 | 2.00 | 2.00 | 2.00 | 2.00 | 2.00 |
| Hydrogenated Polydecene | 13.00 | 13.00 | 13.00 | 13.00 | 13.00 | 13.00 | 13.00 | 13.00 | 13.00 |
| VP/Hexadecene Copolymer | 1.00 | 1.00 | 1.00 | 1.00 | 1.00 | 1.00 | 1.00 | 1.00 | 1.00 |
| PEG-45/Dodecyl Glycol Copolymer | 1.00 | 1.00 | 1.00 | 1.00 | 1.00 | 1.00 | 1.00 | 1.00 | 1.00 |
| Interference Pigments | 6.80 | 6.80 | 6.80 | 6.80 | 6.80 | 6.80 | 6.80 | 6.80 | 6.80 |

Example B16: Lipstick

| INCI-Name | 16A % w/w | 16B % w/w | 16C % w/w | 16D % w/w | 16E % w/w | 16F % w/w | 16G % w/w | 16H % w/w | 16I % w/w |
|---|---|---|---|---|---|---|---|---|---|
| Tocopheryl Acetate | 1.00 | 1.00 | 1.00 | 1.00 | 1.00 | 1.00 | 1.00 | 1.00 | 1.00 |
| BHT | 0.03 | 0.03 | 0.03 | 0.03 | 0.03 | 0.03 | 0.03 | 0.03 | 0.03 |
| Preservatives | q.s. | q.s. | q.s. | q.s. | q.s. | q.s. | q.s. | q.s. | q.s. |
| Parfume. Aroma | q.s. | q.s. | q.s. | q.s. | q.s. | q.s. | q.s. | q.s. | q.s. |
| Water | QS to 100 | QS to 100 | QS to 100 | QS to 100 | QS to 100 | QS to 100 | QS to 100 | QS to 100 | QS to 100 |
| Merocyanine | 1.00 | 1.00 | 1.00 | 1.00 | 1.00 | 1.00 | 1.00 | 1.00 | 1.00 |
| Diethylamino Hydroxy Benzoyl Hexyl Benzoate | | | | | | 3.00 | | | |
| Ethylhexyl Triazone | 2.00 | 1.00 | | | | | 2.00 | 2.00 | 2.00 |
| Ethylhexyl Methoxycinnamate | 5.00 | 5.00 | | | | | | | |
| Bis-Ethylhexyloxyphenol Methoxyphenyl Triazine | | 2.00 | | 2.00 | | 2.00 | 2.00 | | 2.00 |
| Methylene Bis-Benzotriazolyl Tetramethylbutylphenol * | 3.00 | 3.00 | | | 3.00 | 3.00 | | 3.00 | 3.00 |
| MBM-09 | | | 10.00 | 10.00 | 10.00 | 10.00 | 8.00 | 10.00 | 8.00 |
| Phenylene Bis-Diphenyltriazine * | 4.00 | 3.00 | 2.00 | 4.00 | 1.00 | 1.00 | 3.00 | 3.00 | 2.00 |

Aqueous Gel Formulation

Example B17: Clear Gel

| INCI-Name | 17A % w/w | 17B % w/w | 17C % w/w | 17D % w/w | 17E % w/w | 17F % w/w | 17G % w/w | 17H % w/w | 17I % w/w |
|---|---|---|---|---|---|---|---|---|---|
| SD Alcohol 40 | 44.07 | 44.07 | 44.07 | 44.07 | 44.07 | 44.07 | 44.07 | 44.07 | 44.07 |
| Hydroxypropyl Cellulose | 1.67 | 1.67 | 1.67 | 1.67 | 1.67 | 1.67 | 1.67 | 1.67 | 1.67 |
| Isopropyl PPG-2-Isodeceth-7 Carboxylate | 9.64 | 9.64 | 9.64 | 9.64 | 9.64 | 9.64 | 9.64 | 9.64 | 9.64 |
| SD Alcohol 40 | 24.30 | 24.30 | 24.30 | 24.30 | 24.30 | 24.30 | 24.30 | 24.30 | 24.30 |
| Fragrance | 0.60 | 0.60 | 0.60 | 0.60 | 0.60 | 0.60 | 0.60 | 0.60 | 0.60 |
| Deionized Water | Qsp 100 | Qsp 100 | Qsp 100 | Qsp 100 | Qsp 100 | Qsp 100 | Qsp 100 | Qsp 100 | Qsp 100 |
| Citric Acid (and) Silver Citrate | 0.10 | 0.10 | 0.10 | 0.10 | 0.10 | 0.10 | 0.10 | 0.10 | 0.10 |
| Sclerotium Gum | 0.10 | 0.10 | 0.10 | 0.10 | 0.10 | 0.10 | 0.10 | 0.10 | 0.10 |
| Merocyanine | 1.00 | 1.00 | 1.00 | 1.00 | 1.00 | 1.00 | 1.00 | 1.00 | 1.00 |
| Diethylamino Hydroxy Benzoyl Hexyl Benzoate | | | 1.00 | | | | | | |
| Ethylhexyl Triazone | 2.00 | | 2.00 | | 2.00 | | 2.00 | | 2.00 |
| Ethylhexyl Methoxycinnamate | | 7.00 | | | | 7.00 | | 4.00 | 7.00 |
| Bis-Ethylhexyloxyphenol Methoxyphenyl Triazine | | | 2.00 | 2.00 | | | 2.00 | 2.00 | 2.00 |
| MBM-09 | | | | 14.00 | | | | 6.00 | |
| Methylene Bis-Benzotriazolyl Tetramethylbutylphenol * | | | | | 3.00 | 3.00 | 3.00 | 3.00 | |
| Bis-Ethylhexyloxyphenol Methoxyphenyl Triazine ** | 2.00 | 2.00 | 2.00 | 2.00 | 2.00 | 2.00 | 2.00 | 2.00 | 2.00 |
| Phenylene Bis-Diphenyltriazine * | 4.00 | 4.00 | 1.00 | 2.00 | 4.00 | 5.00 | 2.00 | 2.00 | 2.00 |

Make-Up Formulation

Example 18: Foundations; O/W forms

| INCI-Name | 18A % w/w | 18B % w/w | 18C % w/w | 18D % w/w | 18E % w/w | 18F % w/w | 18G % w/w | 18H % w/w | 18I % w/w |
|---|---|---|---|---|---|---|---|---|---|
| Butylene Glycol | 6.50 | 6.50 | 6.50 | 6.50 | 6.50 | 6.50 | 6.50 | 6.50 | 6.50 |
| Magnesium Aluminum Silicate | 0.50 | 0.50 | 0.50 | 0.50 | 0.50 | 0.50 | 0.50 | 0.50 | 0.50 |
| Sodium Carboxymethylcellulose | 0.30 | 0.30 | 0.30 | 0.30 | 0.30 | 0.30 | 0.30 | 0.30 | 0.30 |
| Xanthan Gum | 0.10 | 0.10 | 0.10 | 0.10 | 0.10 | 0.10 | 0.10 | 0.10 | 0.10 |
| Triethanolamine | 1.00 | 1.00 | 1.00 | 1.00 | 1.00 | 1.00 | 1.00 | 1.00 | 1.00 |
| Polysorbate 20 | 0.25 | 0.25 | 0.25 | 0.25 | 0.25 | 0.25 | 0.25 | 0.25 | 0.25 |
| Sericite | 7.00 | 7.00 | 7.00 | 7.00 | 7.00 | 7.00 | 7.00 | 7.00 | 7.00 |
| Iron oxides | 1.10 | 1.10 | 1.10 | 1.10 | 1.10 | 1.10 | 1.10 | 1.10 | 1.10 |
| Spherical Silica | 1.00 | 1.00 | 1.00 | 1.00 | 1.00 | 1.00 | 1.00 | 1.00 | 1.00 |
| Cetearyl octanoate | 10.00 | 10.00 | 10.00 | 10.00 | 10.00 | 10.00 | 10.00 | 10.00 | 10.00 |

Example 18: Foundations; O/W forms

| INCI-Name | 18A % w/w | 18B % w/w | 18C % w/w | 18D % w/w | 18E % w/w | 18F % w/w | 18G % w/w | 18H % w/w | 18I % w/w |
|---|---|---|---|---|---|---|---|---|---|
| Stearic Acid | 2.50 | 2.50 | 2.50 | 2.50 | 2.50 | 2.50 | 2.50 | 2.50 | 2.50 |
| Glyceryl stearate | 2.00 | 2.00 | 2.00 | 2.00 | 2.00 | 2.00 | 2.00 | 2.00 | 2.00 |
| Tridecyl trimellilate | 2.00 | 2.00 | 2.00 | 2.00 | 2.00 | 2.00 | 2.00 | 2.00 | 2.00 |
| Water | qsp | qsp | qsp | qsp | qsp | qsp | qsp | qsp | qsp |
| Preservative | 0.55 | 0.55 | 0.55 | 0.55 | 0.55 | 0.55 | 0.55 | 0.55 | 0.55 |
| Merocyanine | 1.00 | 1.00 | 1.00 | 1.00 | 1.00 | 1.00 | 1.00 | 1.00 | 1.00 |
| Diethylamino Hydroxy Benzoyl Hexyl Benzoate | | | | | 1.00 | | | | |
| Ethylhexyl Triazone | 2.00 | 2.00 | | | | | 2.00 | 2.00 | 2.00 |
| Ethylhexyl Methoxycinnamate | 7.00 | 7.00 | | | | | | | |
| Bis-Ethylhexyloxyphenol Methoxyphenyl Triazine | | 2.00 | | 2.00 | | 2.00 | 2.00 | | 2.00 |
| Methylene Bis-Benzotriazolyl Tetramethylbutylphenol * | 3.00 | 3.00 | | | 3.00 | 2.00 | | 3.00 | 3.00 |
| MBM-09 | | | 10.00 | 10.00 | 10.00 | 10.00 | 10.00 | 10.00 | 10.00 |
| Bis-Ethylhexyloxyphenol Methoxyphenyl Triazine ** | 2.00 | 2.00 | 3.00 | 2.00 | 2.00 | 2.00 | 2.00 | 2.00 | 2.00 |
| Phenylene Bis-Diphenyltriazine * | 2.00 | 4.00 | 2.00 | 2.00 | 4.00 | 1.00 | 3.00 | 2.00 | 4.00 |

Pickering Formulation

Example B19: Pickering Emulsions

| INCI-Name | 19A % w/w | 19B % w/w | 19C % w/w | 19D % w/w | 19E % w/w | 19F % w/w | 19G % w/w | 19H % w/w | 19I % w/w |
|---|---|---|---|---|---|---|---|---|---|
| Octyidodecanol | 5.00 | 5.00 | 5.00 | 5.00 | 5.00 | 5.00 | 5.00 | 5.00 | 5.00 |
| Butylen Glycol Caprylate/Caprate | 4.50 | 4.50 | 4.50 | 4.50 | 4.50 | 4.50 | 4.50 | 4.50 | 4.50 |
| Dicaprylyl Ether | 2.50 | 2.50 | 2.50 | 2.50 | 2.50 | 2.50 | 2.50 | 2.50 | 2.50 |
| Dicaprylyl Carbonate | 6.00 | 6.00 | 6.00 | 6.00 | 6.00 | 6.00 | 6.00 | 6.00 | 6.00 |
| Hydroxyoctacosanyl Hydroxystearate | 2.00 | 2.00 | 2.00 | 2.00 | 2.00 | 2.00 | 2.00 | 2.00 | 2.00 |
| Disteardimonium Hectorit | 1.00 | 1.00 | 1.00 | 1.00 | 1.00 | 1.00 | 1.00 | 1.00 | 1.00 |
| Dimethicone | 2.50 | 2.50 | 2.50 | 2.50 | 2.50 | 2.50 | 2.50 | 2.50 | 2.50 |
| Distarch Phosphate | 1.50 | 1.50 | 1.50 | 1.50 | 1.50 | 1.50 | 1.50 | 1.50 | 1.50 |
| NaCl | 1.00 | 1.00 | 1.00 | 1.00 | 1.00 | 1.00 | 1.00 | 1.00 | 1.00 |
| Glycerin | 10.00 | 10.00 | 10.00 | 10.00 | 10.00 | 10.00 | 10.00 | 10.00 | 10.00 |
| Trisodium EDTA | 1.00 | 1.00 | 1.00 | 1.00 | 1.00 | 1.00 | 1.00 | 1.00 | 1.00 |
| Porpylene Carbonate | 0.33 | 0.33 | 0.33 | 0.33 | 0.33 | 0.33 | 0.33 | 0.33 | 0.33 |
| Phenoxyethanol | 0.40 | 0.40 | 0.40 | 0.40 | 0.40 | 0.40 | 0.40 | 0.40 | 0.40 |
| Diazolidinyl Urea | 0.28 | 0.28 | 0.28 | 0.28 | 0.28 | 0.28 | 0.28 | 0.28 | 0.28 |
| Parfume | 0.20 | 0.20 | 0.20 | 0.20 | 0.20 | 0.20 | 0.20 | 0.20 | 0.20 |
| Water | ad 100 | ad 100 | ad 100 | ad 100 | ad 100 | ad 100 | ad 100 | ad 100 | ad 100 |
| Merocyanine | 1.00 | 1.00 | 1.00 | 1.00 | 1.00 | 1.00 | 1.00 | 1.00 | 1.00 |
| Diethylamino Hydroxy Benzoyl Hexyl Benzoate | | | | | | | | 2.00 | |
| Ethylhexyl Triazone | 2.00 | | 2.00 | | 2.00 | | 2.00 | | 2.00 |
| Ethylhexyl Methoxycinnamate | | 7.00 | | 7.00 | | 5.00 | | 5.00 | |
| MBM-09 | | | | | | 4.00 | | 10.00 | 14.00 |
| Bis-Ethylhexyloxyphenol Methoxyphenyl Triazine | | | 2.00 | 2.00 | | | 2.00 | 2.00 | 2.00 |
| Methylene Bis-Benzotriazolyl Tetramethylbutylphenol * | | | | | 3.00 | 3.00 | 2.00 | 4.00 | |
| Tris-Biphenyl Triazine * | 2.00 | 2.00 | 2.00 | 2.00 | 2.00 | 2.00 | 2.00 | 2.00 | 2.00 |
| Phenylene Bis-Diphenyltriazine * | 2.00 | 3.00 | 4.00 | 2.00 | 2.00 | 3.00 | 2.00 | 4.00 | 5.00 |

Microemulsion Formulation

Example B20: MICROEMULSION LOTION

| INCI-Name | 20A % w/w | 20B % w/w | 20C % w/w | 20D % w/w | 20E % w/w | 20F % w/w | 20G % w/w | 20H % w/w | 20I % w/w |
|---|---|---|---|---|---|---|---|---|---|
| PPG-26-Buteth-26 | 3.00 | 3.00 | 3.00 | 3.00 | 3.00 | 3.00 | 3.00 | 3.00 | 3.00 |
| Ceteareth 20 | 10.00 | 10.00 | 10.00 | 10.00 | 10.00 | 10.00 | 10.00 | 10.00 | 10.00 |

-continued

Example B20: MICROEMULSION LOTION

| INCI-Name | 20A % w/w | 20B % w/w | 20C % w/w | 20D % w/w | 20E % w/w | 20F % w/w | 20G % w/w | 20H % w/w | 20I % w/w |
|---|---|---|---|---|---|---|---|---|---|
| C12-15 Alkyl Benzoate | 5.00 | 5.00 | 5.00 | 5.00 | 5.00 | 5.00 | 5.00 | 5.00 | 5.00 |
| Oleth-5 | 4.00 | 4.00 | 4.00 | 4.00 | 4.00 | 4.00 | 4.00 | 4.00 | 4.00 |
| PPG-11 Stearyl Ether | 10.00 | 10.00 | 10.00 | 10.00 | 10.00 | 10.00 | 10.00 | 10.00 | 10.00 |
| Aluminum Chlorohydrex PG | 15.00 | 15.00 | 15.00 | 15.00 | 15.00 | 15.00 | 15.00 | 15.00 | 15.00 |
| Water | Qs to 100 | Qs to 100 | Qs to 100 | Qs to 100 | Qs to 100 | Qs to 100 | Qs to 100 | Qs to 100 | Qs to 100 |
| Merocyanine | 1.00 | 1.00 | 1.00 | 1.00 | 1.00 | 1.00 | 1.00 | 1.00 | 1.00 |
| Diethylamino Hydroxy Benzoyl Hexyl Benzoate | | | 2.00 | | | | | | |
| Ethylhexyl Triazone | 2.00 | 2.00 | | | | | 2.00 | 2.00 | 2.00 |
| Ethylhexyl Methoxycinnamate | 7.00 | 7.00 | | | | | | | |
| Bis-Ethylhexyloxyphenol Methoxyphenyl Triazine | | 2.00 | | 2.00 | | 2.00 | 2.00 | | 2.00 |
| Methylene Bis-Benzotriazolyl Tetramethylbutylphenol * | 3.00 | 3.00 | | | 3.00 | 3.00 | | 3.00 | 3.00 |
| MBM-09 | | | 10.00 | 10.00 | 10.00 | 10.00 | 5.00 | 5.00 | 10.00 |
| Tris-Biphenyl Triazine * | 2.00 | 2.00 | 2.00 | 2.00 | 1.00 | 2.00 | 2.00 | 2.00 | 2.00 |
| Phenylene Bis-Diphenyltriazine * | 4.00 | 3.00 | 1.00 | 2.00 | 2.00 | 1.00 | 1.00 | 2.00 | 4.00 |

Cationic Formulation

Example B21: Cationic O/W sun cream

| | INCI-Name | 21A % w/w | 21B % w/w | 21C % w/w | 21D % w/w | 21E % w/w | 21F % w/w | 21G % w/w | 21H % w/w | 21I % w/w |
|---|---|---|---|---|---|---|---|---|---|---|
| Part A | Distearyldimonium Chloride | 3.50 | 3.50 | 3.50 | 3.50 | 3.50 | 3.50 | 3.50 | 3.50 | 3.50 |
| | Glyceryl Stearate | 1.50 | 1.50 | 1.50 | 1.50 | 1.50 | 1.50 | 1.50 | 1.50 | 1.50 |
| | Stearyl Alcohol | 1.00 | 1.00 | 1.00 | 1.00 | 1.00 | 1.00 | 1.00 | 1.00 | 1.00 |
| | C12-15 Alkyl Benzoate | 5.00 | 5.00 | 5.00 | 5.00 | 5.00 | 5.00 | 5.00 | 5.00 | 5.00 |
| | Diethylhexyl Carbonate | 3.00 | 3.00 | 3.00 | 3.00 | 3.00 | 3.00 | 3.00 | 3.00 | 3.00 |
| | Cetyl Ricinoleate | 1.00 | 1.00 | 1.00 | 1.00 | 1.00 | 1.00 | 1.00 | 1.00 | 1.00 |
| | Triisostearin | 1.00 | 1.00 | 1.00 | 1.00 | 1.00 | 1.00 | 1.00 | 1.00 | 1.00 |
| Part B | Aqua | Qs to 100 | Qs to 100 | Qs to 100 | Qs to 100 | Qs to 100 | Qs to 100 | Qs to 100 | Qs to 100 | Qs to 100 |
| | Glycerin | 3.00 | 3.00 | 3.00 | 3.00 | 3.00 | 3.00 | 3.00 | 3.00 | 3.00 |
| | Trisodium EDTA | 0.20 | 0.20 | 0.20 | 0.20 | 0.20 | 0.20 | 0.20 | 0.20 | 0.20 |
| Part C | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.80 | 0.80 | 0.80 | 0.80 | 0.80 | 0.80 | 0.80 | 0.80 | 0.80 |
| | Merocyanine | 1.00 | 1.00 | 1.00 | 1.00 | 1.00 | | 1.00 | 1.00 | 1.00 |
| | Diethylamino Hydroxy Benzoyl Hexyl Benzoate | | | | | | 1.00 | | | |
| | Ethylhexyl Triazone | 2.00 | | 2.00 | | 2.00 | | 2.00 | | 2.00 |
| | Ethylhexyl Methoxycinnamate | | 1.00 | | | | 6.00 | | 7.00 | 7.00 |
| | MBM-09 | | 6.00 | | 14.00 | | 8.00 | | | |
| | Bis-Ethylhexyloxyphenol Methoxyphenyl Triazine | | | 2.00 | 2.00 | | | 2.00 | 2.00 | |
| | Methylene Bis-Benzotriazolyl Tetramethylbutylphenol * | | | | | 3.00 | 2.00 | 3.00 | 3.00 | |
| | Methanone, 1,1'-(1,4-piperazinediyl)bis[1-[2-[4-(diethylamino)-2-hydroxybenzoyl]phenyl]- CAS number (919803-06-8) * | 2.00 | 2.00 | 2.00 | 2.00 | 2.00 | 3.00 | 2.00 | 2.00 | 2.00 |
| | Phenylene Bis-Diphenyltriazine * | 3.00 | 4.00 | 3.00 | 3.00 | 1.00 | 2.00 | 2.00 | 4.00 | 3.00 |

Si/W Formulation

Example B22: Si/W sun cream

| | INCI-Name | 22A % w/w | 22B % w/w | 22C % w/w | 22D % w/w | 22E % w/w | 22F % w/w | 22G % w/w | 22H % w/w | 22I % w/w |
|---|---|---|---|---|---|---|---|---|---|---|
| Part A | Cyclopentasiloxane (and) Dimethicone/Vinyl Dimethicone Crosspolymer | 8.00 | 8.00 | 8.00 | 8.00 | 8.00 | 8.00 | 8.00 | 8.00 | 8.00 |
| | Dimethicone (and) Dimethicone/Vinyl Dimethicone Crosspolymer | 30.00 | 30.00 | 30.00 | 30.00 | 30.00 | 30.00 | 30.00 | 30.00 | 30.00 |
| | Cyclopentasiloxane | 10.00 | 10.00 | 10.00 | 10.00 | 10.00 | 10.00 | 10.00 | 10.00 | 10.00 |
| Part B | 1.3-Butylen Glycol | 3.00 | 3.00 | 3.00 | 3.00 | 3.00 | 3.00 | 3.00 | 3.00 | 3.00 |
| | Polyglyceryl-3 Disiloxane Dimethicone | 0.60 | 0.60 | 0.60 | 0.60 | 0.60 | 0.60 | 0.60 | 0.60 | 0.60 |
| | Polyglyceryl-3 Polydimethylsiloxyethyl Dimethicone | 0.30 | 0.30 | 0.30 | 0.30 | 0.30 | 0.30 | 0.30 | 0.30 | 0.30 |
| | Acrylamide/Sodium Acryloyldimethyltaurate Copolymer (and) Isohexadecane (and) Polysorbate 80 | 0.60 | 0.60 | 0.60 | 0.60 | 0.60 | 0.60 | 0.60 | 0.60 | 0.60 |
| | Ammonium Acryloyldimethyltaurate/VP Copolymer | 0.65 | 0.65 | 0.65 | 0.65 | 0.65 | 0.65 | 0.65 | 0.65 | 0.65 |
| | Sodium Chloride | 0.10 | 0.10 | 0.10 | 0.10 | 0.10 | 0.10 | 0.10 | 0.10 | 0.10 |
| | Aqua | Qs to 100 | Qs to 100 | Qs to 100 | Qs to 100 | Qs to 100 | Qs to 100 | Qs to 100 | Qs to 100 | Qs to 100 |
| | Merocyanine | 1.00 | 1.00 | 1.00 | 1.00 | 1.00 | 1.00 | 1.00 | 1.00 | 1.00 |
| | Diethylamino Hydroxy Benzoyl Hexyl Benzoate | | | 2.00 | | | | | | |
| | Ethylhexyl Triazone | 2.00 | 2.00 | | | | | 2.00 | 2.00 | 1.00 |
| | Ethylhexyl Methoxycinnamate | 7.00 | 7.00 | | | | | | | |
| | Bis-Ethylhexyloxyphenol Methoxyphenyl Triazine | | 1.00 | | 1.00 | | 1.00 | 2.00 | | 1.00 |
| | Methylene Bis-Benzotriazolyl Tetramethylbutylphenol * | 3.00 | 2.00 | | | 2.00 | 3.00 | | 3.00 | 1.00 |
| | MBM-09 | | | 20.00 | 10.00 | 10.00 | 10.00 | 10.00 | 10.00 | 13.00 |
| | Methanone, 1,1'-(1,4-piperazine-diyl)bis[1-[2-[4-(diethylamino)-2-hydroxybenzoyl]phenyl]- CAS number (919803-06-8) * | 2.00 | 2.00 | 2.00 | 2.00 | 2.00 | 2.00 | 4.00 | 4.00 | 2.00 |
| | Phenylene Bis-Diphenyltriazine * | 2.00 | 2.00 | 2.00 | 1.00 | 3.00 | 2.00 | 2.00 | 1.00 | 2.00 |

O/W Formulation                                   Anionic System Emulsifier

Example B23: Emulsion high Protection

| | INCI-Name | 23A % w/w | 23B % w/w | 23C % w/w | 23D % w/w | 23E % w/w | 23F % w/w | 23G % w/w | 23H % w/w | 23I % w/w |
|---|---|---|---|---|---|---|---|---|---|---|
| Part A | Cyclomethicone | 2.00 | 2.00 | 2.00 | 2.00 | 2.00 | 2.00 | 2.00 | 2.00 | 2.00 |
| | Dibutyl Adipate | 4.00 | 4.00 | 4.00 | 4.00 | 4.00 | 4.00 | 4.00 | 4.00 | 4.00 |
| | Tridecyl Trimellitate | 3.00 | 3.00 | 3.00 | 3.00 | 3.00 | 3.00 | 3.00 | 3.00 | 3.00 |
| | C12-15 Alkyl Benzoate | 1.00 | 1.00 | 1.00 | 1.00 | 1.00 | 1.00 | 1.00 | 1.00 | 1.00 |
| | Ethylhexyl Palmitate | 3.00 | 3.00 | 3.00 | 3.00 | 3.00 | 3.00 | 3.00 | 3.00 | 3.00 |
| | Glyceryl Stearate | 1.50 | 1.50 | 1.50 | 1.50 | 1.50 | 1.50 | 1.50 | 1.50 | 1.50 |
| | Potassium Cetyl Phosphate | 1.80 | 1.80 | 1.80 | 1.80 | 1.80 | 1.80 | 1.80 | 1.80 | 1.80 |
| | VP/Eicosene Copolymer | 0.60 | 0.60 | 0.60 | 0.60 | 0.60 | 0.60 | 0.60 | 0.60 | 0.60 |
| Part B | Aqua | Qs to 100 | Qs to 100 | Qs to 100 | Qs to 100 | Qs to 100 | Qs to 100 | Qs to 100 | Qs to 100 | Qs to 100 |
| | Acrylates/Palmeth-25 Acrylate Copolymer | 0.25 | 0.25 | 0.25 | 0.25 | 0.25 | 0.25 | 0.25 | 0.25 | 0.25 |
| | Glycerin | 6.00 | 6.00 | 6.00 | 6.00 | 6.00 | 6.00 | 6.00 | 6.00 | 6.00 |
| | Disodium EDTA | 0.20 | 0.20 | 0.20 | 0.20 | 0.20 | 0.20 | 0.20 | 0.20 | 0.20 |
| Part C | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.30 | 0.30 | 0.30 | 0.30 | 0.30 | 0.30 | 0.30 | 0.30 | 0.30 |
| | Diethylamino Hydroxy Benzoyl Hexyl Benzoate | | | | | | | | | 2.00 |

-continued

| | Example B23: Emulsion high Protection | | | | | | | | |
|---|---|---|---|---|---|---|---|---|---|
| INCI-Name | 23A % w/w | 23B % w/w | 23C % w/w | 23D % w/w | 23E % w/w | 23F % w/w | 23G % w/w | 23H % w/w | 23I % w/w |
| Ethylhexyl Triazone | 2.00 | | 2.00 | | 2.00 | | 2.00 | | |
| BBDAPT (CAS Nb: 207562-42-3) | | | | | | | | | 2.00 |
| Ethylhexyl Methoxycinnamate | | 7.00 | | 7.00 | | 7.00 | | 7.00 | 7.00 |
| Bis-Ethylhexyloxyphenol Methoxyphenyl Triazine | | | 2.00 | 2.00 | | | 2.00 | 2.00 | 2.00 |
| Methylene Bis-Benzotriazolyl Tetramethylbutylphenol * | | | | | 3.00 | 3.00 | 3.00 | 3.00 | |
| Phenylene Bis-Diphenyltriazine * | 4.00 | 4.00 | 4.00 | 4.00 | 4.00 | 4.00 | 4.00 | 4.00 | 2.00 |
| MBM-09 | 4.00 | 4.00 | 4.00 | 4.00 | 4.00 | 4.00 | 4.00 | 10.00 | 2.00 |

| | | Example B24: Sun Milk | | | | | | | | |
|---|---|---|---|---|---|---|---|---|---|---|
| | INCI-Name | 24A % w/w | 24B % w/w | 24C % w/w | 24D % w/w | 24E % w/w | 24F % w/w | 24G % w/w | 24H % w/w | 24I % w/w |
| Part A | C12-15 Alkyl Benzoate | 2.00 | 2.00 | 2.00 | 2.00 | 2.00 | 2.00 | 2.00 | 2.00 | 2.00 |
| | Coco-Caprylate | 4.00 | 4.00 | 4.00 | 4.00 | 4.00 | 4.00 | 4.00 | 4.00 | 4.00 |
| | Tridecyl Trimellitate | 3.00 | 3.00 | 3.00 | 3.00 | 3.00 | 3.00 | 3.00 | 3.00 | 3.00 |
| | Dibutyl Adipate | 1.00 | 1.00 | 1.00 | 1.00 | 1.00 | 1.00 | 1.00 | 1.00 | 1.00 |
| | Isohexadecane | 3.00 | 3.00 | 3.00 | 3.00 | 3.00 | 3.00 | 3.00 | 3.00 | 3.00 |
| | Cyclopentasiloxane | 4.00 | 4.00 | 4.00 | 4.00 | 4.00 | 4.00 | 4.00 | 4.00 | 4.00 |
| | Stearic Acid | 5.00 | 5.00 | 5.00 | 5.00 | 5.00 | 5.00 | 5.00 | 5.00 | 5.00 |
| | PEG-100 Stearate (and) Glyceryl Stearate | 0.80 | 0.80 | 0.80 | 0.80 | 0.80 | 0.80 | 0.80 | 0.80 | 0.80 |
| | Potassium Cetyl Phosphate | 1.30 | 1.30 | 1.30 | 1.30 | 1.30 | 1.30 | 1.30 | 1.30 | 1.30 |
| | PVP/Eicosene Copolymer | 1.00 | 1.00 | 1.00 | 1.00 | 1.00 | 1.00 | 1.00 | 1.00 | 1.00 |
| Part B | Aqua | Qs to 100 | Qs to 100 | Qs to 100 | Qs to 100 | Qs to 100 | Qs to 100 | Qs to 100 | Qs to 100 | Qs to 100 |
| | Propylene Glycol | 5.00 | 5.00 | 5.00 | 5.00 | 5.00 | 5.00 | 5.00 | 5.00 | 5.00 |
| | Xanthan Gum | 0.20 | 0.20 | 0.20 | 0.20 | 0.20 | 0.20 | 0.20 | 0.20 | 0.20 |
| | Acrylates/C10-30 Alkyl Acrylate Crosspolymer | 0.15 | 0.15 | 0.15 | 0.15 | 0.15 | 0.15 | 0.15 | 0.15 | 0.15 |
| | Disodium EDTA | 0.15 | 0.15 | 0.15 | 0.15 | 0.15 | 0.15 | 0.15 | 0.15 | 0.15 |
| Part C | Triethanolamine | Qs | Qs | Qs | Qs | Qs | Qs | Qs | Qs | Qs |
| | Dimethicone | 0.40 | 0.40 | 0.40 | 0.40 | 0.40 | 0.40 | 0.40 | 0.40 | 0.40 |
| | Phenoxyethanol (and) Methylparaben (and) Ethylparaben (and) Butylparaben (and) Propylparaben (and) Isobutylparaben | 0.70 | 0.70 | 0.70 | 0.70 | 0.70 | 0.70 | 0.70 | 0.70 | 0.70 |
| | Tocopheryl Acetate | 0.90 | 0.90 | 0.90 | 0.90 | 0.90 | 0.90 | 0.90 | 0.90 | 0.90 |
| | Diethylamino Hydroxy Benzoyl Hexyl Benzoate | | | | | | | | | 2.00 |
| | Ethylhexyl Triazone | 2.00 | 1.00 | | | | | 2.00 | 2.00 | 2.00 |
| | BBDAPT (CAS Nb: 207562-42-3) | | 1.00 | | | | | | | 2.00 |
| | Ethylhexyl Methoxycinnamate | 7.00 | 7.00 | | | | | | | |
| | Bis-Ethylhexyloxyphenol Methoxyphenyl Triazine | | 2.00 | | 2.00 | | 2.00 | 2.00 | | 2.00 |
| | Methylene Bis-Benzotriazolyl Tetrametylbutylphenol * | 3.00 | 3.00 | | | 3.00 | 3.00 | | 3.00 | 3.00 |
| | Phenylene Bis-Diphenyltriazine * | 4.00 | 4.00 | 4.00 | 4.00 | 4.00 | 4.00 | 4.00 | 4.00 | 4.00 |
| | MBM-09 | 4.00 | 4.00 | 10.00 | 4.00 | 4.00 | 4.00 | 4.00 | 4.00 | 2.00 |

| | | Example B25: Sun lotion | | | | | | |
|---|---|---|---|---|---|---|---|---|
| | INCI-Name | 25A % w/w | 25B % w/w | 25C % w/w | 25D % w/w | 25E % w/w | 25F % w/w | 25G % w/w |
| Part A | Potassium Cetyl Phosphate | 1.80 | 1.80 | 1.80 | 1.80 | 1.80 | 1.80 | 1.80 |
| | Glycery Stearate | 2.5 | 2.5 | 2.5 | 2.5 | 2.5 | 2.5 | 2.5 |
| | Stearyl Alcohol | 2.5 | 2.5 | 2.5 | 2.5 | 2.5 | 2.5 | |
| | C12-15 Alkyl Benzoate | | | 5.00 | 12.00 | 2.00 | | |
| | Dibutyl Adipate | 15.00 | 5.00 | | | | 15.00 | 5.00 |

-continued

| | | Example B25: Sun lotion | | | | | | |
|---|---|---|---|---|---|---|---|---|
| | INCI-Name | 25A % w/w | 25B % w/w | 25C % w/w | 25D % w/w | 25E % w/w | 25F % w/w | 25G % w/w |
| | Ethylhexyl Benzoate | 5.00 | 8.00 | | 10.00 | | 8.00 | 7.00 |
| | Di C12-13 Alkyl Tartrate | | 5.00 | 5.00 | | | 5.00 | |
| | Phenoxyethyl Ester | | | 5.00 | | | | 5.00 |
| | Diisopropyl Sebacate | | | | | | | 11.00 |
| | Butyl Methoxydibenzoylmethane | 3.00 | | | | | | |
| | Diethylamino Hydroxybenzoyl Hexyl Benzoate | | | 2.00 | | 5.00 | | 10.00 |
| | Ethylhexyl Triazone | | 3.00 | 2.00 | | | 3.00 | 3.00 |
| | Bis-Ethylhexyloxyphenol Methoxyphenyl Triazine | 2.00 | 2.00 | | 3.00 | | 2.00 | 3.00 |
| Part B | Aqua | Qsp to 100 | Qsp to 100 | Qsp to 100 | Qsp to 100 | Qsp to 100 | Qsp to 100 | Qsp to 100 |
| | Glycerin | 10.00 | 10.00 | 10.00 | 10.00 | 10.00 | 10.00 | 10.00 |
| | Xanthan Gum | 0.30 | 0.30 | 0.30 | 0.30 | 0.30 | 0.30 | 0.30 |
| | Trometamine | | | | | | | 0.92 |
| | Phenylbenzimidazole Sulfonic Acid | | | | | | | 2.00 |
| Part C | Phenylene Bis-Diphenyltriazine * | 3.00 | 2.00 | 2.00 | 2.00 | | | |
| | Phenylene Bis-Diphenyltriazine $^{a)}$ | | | | | 2.00 | 1.70 | 2.30 |
| | Methanone, 1,1'-(1,4-piperazinediyl)-bis[1-[2-[4-(diethylamino)-2-hydroxy-benzoyl]phenyl]- CAS number (919803-06-8) * | | | | | 3.00 | 1.00 | |
| | Phenoxyethanol (and) Methylparaben (and) Ethylparaben (and) Butylparaben (and) Propylparaben (and) Isobutylparaben | 0.80 | 0.80 | 0.80 | 0.80 | 0.80 | 0.80 | 0.80 |
| | In vitro SPF measured according to the method described | 22 | 30 | 18 | 17 | 8 | 26 | 63 |
| | UVA PF measured according to the method described | 18 | 11.3 | 7.9 | 12.9 | 13 | 8.9 | 29.2 |
| | Critical wavelength (nm) | 381 | 376 | 377 | 382 | 386 | 381 | 378 |

Foodnote:
$^{a)}$ particulate organic filter 50-200 nm, aqueous dispersion, active ingredient 20-30 w/w %

Method to Assess In Vitro Sun Protection Factor Measurement (SPF)

End-product application rate 1.3 mg/cm² on PMMA plates (Helioplates®)

UV Transmittance analysis with Labsphere UV-1000S Transmittance Analyser $$SPF = \frac{\int_{290nm}^{400nm} E_\lambda \cdot S_\lambda \cdot d\lambda}{\int_{290nm}^{400nm} E_\lambda \cdot S_\lambda \cdot T_\lambda \cdot d\lambda}$$

wherein $E_\lambda$=erythema action spectrum; $S_\lambda$=solar spectral irradiance and $T_\lambda$=spectral transmittance of the sample.

Method to Assess In Vitro UVA Protection Factor (UVA PF)

End-product application rate 1.3 mg/cm² on PMMA plates (Helioplates®)

UV Transmittance analysis with Labsphere UV-1000S Transmittance Analyser

Pre-irradiation step (to take the sun care product photostability into account) via a solar simulator such as Atlas Suntest CPS+

$$PFUVA = \frac{\sum_{320}^{400} \Delta\lambda}{\sum_{320}^{400} T_\lambda \cdot \Delta\lambda} = \frac{1}{T_m}$$

Wherein $T_\lambda$=sunscreen product transmittance at wave length $\lambda$ and $T_m$=mean arithmetical value of Transmittance data in the UVA range.

Critical Wavelength

The critical wavelength is the wavelength at which the sunscreen allows 10% of the rays to penetrate. A sunscreen with a critical wavelength over 370 nm is considered by the FDA to provide excellent UV protection.

The invention claimed is:

1. A cosmetic or pharmaceutical composition comprising a UV filter combination of (a) an aqueous dispersion of 5,6,5',6'-tetraphenyl-3,3'-(1,4-Phenylene)bis(1,2,4-Triazine) corresponding to the formula (1)

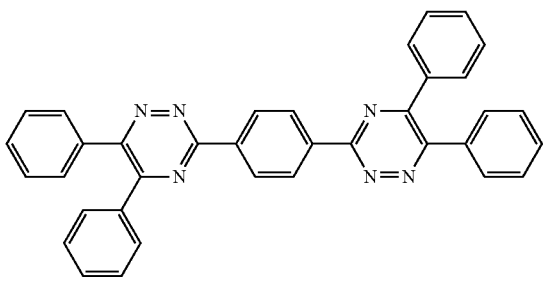

in particulate form; and
(b) UV filters selected from the group consisting of
  ($b_1$) Bis-Ethylhexyloxyphenol Methoxyphenyl Triazine;
  ($b_2$) Butyl Methoxydibenzoylmethane;
  ($b_3$) Diethylhexyl Butamido Triazone;
  ($b_4$) Ethylhexyl Triazone;
  ($b_5$) Diethylamino Hydroxy Benzoyl Hexyl Benzoate;
  ($b_6$) Ethylhexyl Methoxycinnamate;
  ($b_7$) Ethylhexyl Salicylate;
  ($b_8$) Homosalate;
  ($b_9$) Octocrylene;
  ($b_{10}$) Methylene Bis-Benzotriazolyl Tetramethylbutylphenol;
  ($b_{11}$) Phenylbenzimidazole Sulfonic Acid;
  ($b_{12}$) Titanium Dioxide;
  ($b_{13}$) Tris-Biphenyl Triazine;
  ($b_{14}$) (2-{4-[2-(4-Diethylamino-2-hydroxy-benzoyl)-benzoyl]-piperazine-1-carbonyl}-phenyl)-(4-diethylamino-2-hydroxy-phenyl)-methanone;
  ($b_{15}$) BBDAPT; Benzoic acid, 4,4'-[[6-[[3-[1,3,3,3-tetramethyl-1-[(trimethylsilyl)oxy]-1 disiloxanyl]propyl]amino]-1,3,5-triazine-2,4-diyl]diimino]bis-, dibutyl ester;
  ($b_{16}$) benzylidene malonates;
  ($b_{17}$) merocyanine derivatives;
  ($b_{18}$) Bis(butylbenzoate) diaminotriazine aminopropylsiloxane;
  ($b_{19}$) Bis-Ethylhexyloxyphenol Methoxyphenyl Triazine encapsulated in a polymer matrix;
  ($b_{20}$) 2-(2H-Benzotriazol-2-yl)-6-[(2-ethylhexy loxy) methyl]-4-methylphenol; and
  ($b_{21}$) 2-Propenoic acid, 3-(4-methoxyphenyl)-, 2-methylphenyl ester,
wherein the average particle size of component (a) is in the range from 0.02 to 2 micrometres; and
wherein said composition contains from 0.1 to 15% by weight, based on the total weight of the composition, of the UV filter combination of (a) and (b); and
wherein said composition contains at least two of the UV filters ($b_1$)-($b_{21}$); and
wherein said composition also contains a pharmaceutically or cosmetically acceptable excipient and wherein the compound of formula (1) is present in the micronized state.

2. The cosmetic or pharmaceutical composition according to claim 1, wherein component (a) represents an aqueous dispersion comprising the UV filter of formula (1) in a concentration range from 40 to 50 b.w.

3. The cosmetic or pharmaceutical composition according to claim 2, wherein the aqueous dispersion according to component (a) contains a grinding aid that is PPG-1-PEG-9 Lauryl Glycol Ether and the average particle size of formula (1) is in the range from 0.1 to 1.0 micrometres.

4. The cosmetic or pharmaceutical composition according to claim 1, wherein the aqueous dispersion according to component (a) contains a dispersing agent which is PPG-1-PEG-9 Lauryl Glycol Ether.

5. The cosmetic or pharmaceutical composition according to claim 1, wherein component (a) represents an aqueous dispersion comprising the UV filter of formula (1) encapsulated in a polymer carrier in a concentration range from 20 to 50% b.w.

6. The cosmetic or pharmaceutical composition according to claim 1, comprising
  (UV1) 5,6,5',6'-tetraphenyl-3,3'-(1,4-Phenylene)bis(1,2,4-Triazine) (a) of formula (1);
  (UV2) Bis-Ethylhexyloxyphenol Methoxyphenyl Triazine ($b_1$); and
  (UV3) filters selected from the group consisting of
    ($UV3_1$) Diethylamino Hydroxy Benzoyl Hexyl Benzoate ($b_5$);
    ($UV3_2$) Butyl Methoxydibenzoylmethane ($b_2$); and
    ($UV3_3$) Benzoic acid, 4,4'-[[6-[[3-[1,3,3,3-tetramethyl-1-[(trimethylsilyl)oxy]-1 disiloxanyl]propyl]amino]-1,3,5-triazine-2,4-diyl]diimino]bis-, dibutyl ester ($b_{15}$).

7. The cosmetic or pharmaceutical composition according to claim 1, comprising
  (UV1) 5,6,5',6'-tetraphenyl-3,3'-(1,4-Phenylene)bis(1,2,4-Triazine) (a) of formula (1);
  (UV2) Methylene Bis-Benzotriazolyl Tetramethylbutylphenol ($b_{10}$); and
  (UV3) filters selected from the group consisting of
    ($UV3_1$) Bis-Ethylhexyloxyphenol Methoxyphenyl Triazine ($b_1$);
    ($UV3_2$) Diethylamino Hydroxy Benzoyl Hexyl Benzoate ($b_5$);
    ($UV3_3$) Butyl Methoxydibenzoylmethane ($b_2$); and
    ($UV3_4$) Benzoic acid, 4,4'-[[6-[[3-[1,3,3,3-tetramethyl-1-[(trimethylsilyl)oxy]-1 disiloxanyl]propyl]amino]-1,3,5-triazine-2,4-diyl]diimino]bis-, dibutyl ester.

8. The cosmetic or pharmaceutical composition according to claim 1, comprising
  (UV1) Phenylene Bis-Diphenyltriazine (a) of formula (1);
  (UV2) Diethylamino Hydroxy Benzoyl Hexyl Benzoate ($b_5$); and
  (UV3) Butyl Methoxydibenzoylmethane ($b_2$).

9. The cosmetic or pharmaceutical composition according to claim 1, comprising
  (UV1) 5,6,5',6'-tetraphenyl-3,3'-(1,4-Phenylene)bis(1,2,4-Triazine) (a) of formula (1);
  (UV2) Ethylhexyl Triazone ($b_4$);
  and UV filters (UV3) selected from the group consisting of
    ($UV3_1$) Methylene Bis-Benzotriazolyl Tetramethylbutylphenol ($b_{10}$);
    ($UV3_2$) Bis-Ethylhexyloxyphenol Methoxyphenyl Triazine ($b_1$);
    ($UV3_3$) Diethylamino Hydroxy Benzoyl Hexyl Benzoate ($b_5$);
    ($UV3_4$) Butyl Methoxydibenzoylmethane ($b_2$); and
    ($UV3_5$) Benzoic acid, 4,4'-[[6-[[3-[1,3,3,3-tetramethyl-1-[(trimethylsilyl)oxy]-1 disiloxanyl]propyl]amino]-1,3,5-triazine-2,4-diyl]diimino]bis-, dibutyl ester ($b_{15}$).

10. The cosmetic or pharmaceutical composition according to claim 1, comprising (UV1) 5,6,5',6'-tetraphenyl-3,3'-(1,4-Phenylene)bis(1,2,4-Triazine) (a) of formula (1);
(UV2) Benzoic acid, 4,4'-[[6-[[3-[1,3,3,3-tetramethyl-1-[(trimethylsilyl)oxy]-1 disiloxanyl]propyl]amino]-1,3,5-triazine-2,4-diyl]diimino]bis-, dibutyl ester ($b_{15}$);
and UV filters (UV3) selected from the group consisting of
  (UV3$_1$) Methylene Bis-Benzotriazolyl Tetramethylbutylphenol ($b_{10}$);
  (UV3$_2$) Bis-Ethylhexyloxyphenol Methoxyphenyl Triazine ($b_1$);
  (UV3$_3$) Diethylamino Hydroxy Benzoyl Hexyl Benzoate ($b_5$); and
  (UV3$_4$) Butyl Methoxydibenzoylmethane ($b_2$).

11. The cosmetic or pharmaceutical composition according to claim 1, comprising
(UV1) 5,6,5',6'-tetraphenyl-3,3'-(1,4-Phenylene)bis(1,2,4-Triazine) (a) of formula (1);
(UV2) Methylene Bis-Benzotriazolyl Tetramethylbutylphenol ($b_{10}$);
(UV3) Ethylhexyl Triazone ($b_4$);
and UV filters (UV4) selected from the group consisting of
  (UV4$_1$) Bis-Ethylhexyloxyphenol Methoxyphenyl Triazine ($b_1$);
  (UV4$_2$) Diethylamino Hydroxy Benzoyl Hexyl Benzoate ($b_5$);
  (UV4$_3$) Butyl Methoxydibenzoylmethane ($b_2$); and
  (UV4$_4$) Benzoic acid, 4,4'-[[6-[[3-[1,3,3,3-tetramethyl-1-[(trimethylsilyl)oxy]-1 disiloxanyl]propyl]amino]-1,3,5-triazine-2,4-diyl]diimino]bis-, dibutyl ester ($b_{15}$).

12. The cosmetic or pharmaceutical composition according to claim 1, comprising
(UV1) 5,6,5',6'-tetraphenyl-3,3'-(1,4-Phenylene)bis(1,2,4-Triazine) (a) of formula (1);
(UV2) Bis-Ethylhexyloxyphenol Methoxyphenyl Triazine ($b_1$);
(UV3) Ethylhexyl Triazone ($b_4$);
and the UV filters (UV4) selected from the group consisting of
  (UV4$_1$) Diethylamino Hydroxy Benzoyl Hexyl Benzoate ($b_5$);
  (UV4$_2$) Butyl Methoxydibenzoylmethane ($b_2$); and
  (UV4$_3$) Benzoic acid, 4,4'-[[6-[[3-[1,3,3,3-tetramethyl-1-[(trimethylsilyl)oxy]-1 disiloxanyl]propyl]amino]-1,3,5-triazine-2,4-diyl]diimino]bis-, dibutyl ester ($b_{15}$).

13. The cosmetic or pharmaceutical composition according to claim 1, comprising
(UV1) 5,6,5',6'-tetraphenyl-3,3'-(1,4-Phenylene)bis(1,2,4-Triazine) (a) of formula (1);
(UV2) Diethylamino Hydroxy Benzoyl Hexyl Benzoate ($b_5$);
(UV3) Butyl Methoxydibenzoylmethane ($b_2$); and
(UV4) Ethylhexyl Triazone (b4).

14. The cosmetic or pharmaceutical composition according to claim 1, comprising
(UV1) 5,6,5',6'-tetraphenyl-3,3'-(1,4-Phenylene)bis(1,2,4-Triazine) (a) of formula (1);
(UV2) Bis-Ethylhexyloxyphenol Methoxyphenyl Triazine ($b_1$);
(UV3) Ethylhexyl Triazone ($b_4$);
the UV filters (UV4) selected from the group consisting of
  (UV4$_1$)) Methylene Bis-Benzotriazolyl Tatramethylbutylphenyl ($b_{10}$);
  (UV4$_2$) Diethylamino Hydroxy Benzoyl Hexyl Benzoate ($b_5$); and
  (UV4$_3$) Butyl Methoxydibenzoylmethane ($b_2$); and
the UV filters (UV5) selected from the group consisting of
  (UV5$_1$) Ethylhexyl Salicylate ($b_7$);
  (UV5$_2$) Tris-Biphenyl Triazine ($b_{13}$);
  (UV5$_3$) Octocrylene ($b_9$);
  (UV5$_4$) Diethylhexyl Butamido Triazone ($b_3$);
  (UV5$_5$) Phenylbenzimidazole Sulfonic Acid ($b_{11}$);
  (UV5$_6$) Titanium Dioxide ($b_{12}$)
  (UV5$_7$) Homosalate ($b_8$);
  (UV5$_8$) (2-{4-[2-(4-Diethylamino-2-hydroxy-benzoyl)-benzoyl]-piperazine-1-carbonyl}-phenyl)-(4-diethylamino-2-hydroxy-phenyl)-methanone ($b_{14}$); and
  (UV5$_9$) Benzoic acid, 4,4'-[[6-[[3-[1,3,3,3-tetramethyl-1-[(trimethylsilyl)oxy]-1 disiloxanyl]propyl]amino]-1,3,5-triazine-2,4-diyl]diimino]bis-, dibutyl ester ($b_{15}$).

15. The cosmetic or pharmaceutical composition according to claim 1, comprising
(UV1) 5,6,5',6'-tetraphenyl-3,3'-(1,4-Phenylene)bis(1,2,4-Triazine) (a) of formula (1);
(UV2) Methylene Bis-Benzotriazolyl Tetramethylbutylphenol ($b_{10}$);
(UV3) Ethylhexyl Triazone ($b_4$);
the UV filters (UV4) selected from the group consisting of
  (UV4$_1$) Diethylamino Hydroxy Benzoyl Hexyl Benzoate ($b_5$)
  (UV4$_2$) Butyl Methoxydibenzoylmethane ($b_2$); and
the UV filters (UV5) selected from the group consisting of
  (UV5$_1$) Ethylhexyl Salicylate ($b_1$)
  (UV5$_2$) Tris-Biphenyl Triazine ($b_{13}$)
  (UV5$_3$) Octocrylene ($b_9$)
  (UV5$_4$) Diethylhexyl Butamido Triazone ($b_3$)
  (UV5$_5$) Phenylbenzimidazole Sulfonic Acid ($b_{11}$)
  (UV5$_6$) Titanium Dioxide ($b_{12}$)
  (UV5$_7$) Homosalate ($b_8$)
  (UV5$_8$) (2-{4-[2-(4-Diethylamino-2-hydroxy-benzoyl)-benzoyl]-piperazine-1-carbonyl}-phenyl)-(4-diethylamino-2-hydroxy-phenyl)-methanone ($b_{14}$); and
  (UV5$_9$) Benzoic acid, 4,4'-[[6-[[3-[1,3,3,3-tetramethyl-1-[(trimethylsilyl)oxy]-1 disiloxanyl]propyl]amino]-1,3,5-triazine-2,4-diyl]diimino]bis-, dibutyl ester (bis).

16. The cosmetic or pharmaceutical composition according to claim 1, wherein the UV filters ($b_{10}$) Methylene Bis-Benzotriazolyl Tetramethylbutylphenol, ($b_{13}$) Tris-Biphenyl Triazine and ($b_{14}$) (2-{4-[2-(4-Diethylamino-2-hydroxy-benzoyl)-benzoyl]-piperazine-1-carbonyl}-phenyl)-(4-diethylamino-2-hydroxy-phenyl)-methanone are present in the cosmetic or pharmaceutical composition in their micronized state.

17. The cosmetic or pharmaceutical composition according to claim 1, wherein (b) is ($b_1$), ($b_4$) and ($b_5$).

18. The cosmetic or pharmaceutical composition according to claim 1, wherein the micronized UV absorber of formula (I) has an average particle size from 0.1 to 1.0 µm.

19. The cosmetic or pharmaceutical composition according to claim 1, wherein the composition comprises A or B:
A:
  1. potassium cetyl phosphate,
  2. glyceryl stearate,
  3. stearyl alcohol,
  4. dibutyl adipate,
  5. ethylhexyl benzoate, 6. di-C12-13 alkyl tartrate,
7. ethylhexyl triazone,
8. bis-ethylhexyloxyphenol methoxyphenyl triazine,
9. water,
10. glycerin,
11. xanthan gum,
12. aqueous dispersion of 5,6,5',6'-tetraphenyl-3,3'-(1,4-Phenylene)bis(1,2,4-Triazine) and
13. phenoxyethanol, methylparaben, ethyl-paraben, butylparaben, propylparaben, isobutylparaben;

B:
1. potassium cetyl phosphate,
2. glyceryl stearate,
3. stearyl alcohol,
4. ethylhexyl benzoate,
5. phenoxyethyl caprylate,
6. diisopropyl sebacate,
7. diethylamino hydroxybenzoyl hexyl benzoate,
8. ethylhexyl triazone,
9. bis-ethylhexyloxyphenol methoxyphenyl triazine
10. water,
11. glycerin,
12. xanthan gum,
13. tromethamine,
14. phenylbenzimidazol sulfonic acid,
15. 5,6,5',6'-tetraphenyl-3,3'-(1,4-Phenylene)bis(1,2,4-Triazine), and
16. phenoxyethanol, methylparaben, ethyl-paraben, butylparaben, propylparaben, isobutylparaben.

20. The cosmetic or pharmaceutical composition according to claim 1, wherein the composition comprises A or B:

A:

| Compound | Amount (% w/w) |
| --- | --- |
| Potassium Cetyl Phosphate | 1.80 |
| Glyceryl Stearate | 2.50 |
| Stearyl Alcohol | 2.50 |
| Dibutyl Adipate | 5.00 |
| Ethylhexyl Benzoate | 8.00 |
| Di-C12-13 Alkyl Tartrate | 5.00 |
| Ethylhexyl Traizone | 3.00 |
| Bis-ethylhexyloxyphenol methoxyphenyl triazine | 2.00 |
| Aqua | Qsp to 100% |
| Glycerin | 10.00 |
| Xanthan Gum | 0.30 |
| 5,6,5',6'-tetraphenyl-3,3'-(1,4-Phenylene)bis(1,2,4-Triazine) | 2.00 |
| Phenoxyethanol, Methylparaben, Ethylparaben, Butylparaben, Propylparaben, Isobutylparaben | 0.80 |

B:

| Compound | Amount (% w/w) |
| --- | --- |
| Potassium Cetyl Phosphate | 1.80 |
| Glyceryl Stearate | 2.50 |
| Stearyl Alcohol | 2.50 |
| Ethylhexyl Benzoate | 7.00 |
| Phenoxyethyl Caprylate | 5.00 |
| Diisopropyl Sebacate | 11.00 |
| Diethylamino Hydroxybenzoyl Hexyl Benzoate | 10.00 |
| Ethylhexyl Triazone | 3.00 |
| Bis-ethylhexyloxyphenol methoxyphenyl triazine | 3.00 |
| Aqua | Qsp to 100% |
| Glycerin | 10.00 |
| Xanthan Gum | 0.30 |
| Tromethamine | 0.92 |
| Phenylbenzimidazol sulfonic acid | 2.00 |
| 5,6,5',6'-tetraphenyl-3,3'-(1,4-Phenylene)bis(1,2,4-Triazine) | 2.30 |
| Phenoxyethanol, Methylparaben, Ethylparaben, Butylparaben, Propylparaben, Isobutylparaben. | 0.80 |

21. The cosmetic or pharmaceutical composition according to claim 1, wherein said composition contains from 0.5 to 10% by weight, based on the total weight of the composition, of the UV absorber mixture (a) and (b).

22. A cosmetic or pharmaceutical composition comprising a UV filter combination of
(a) an aqueous dispersion of 5,6,5',6'-tetraphenyl-3,3'-(1,4-Phenylene)bis(1,2,4-Triazine) corresponding to the formula

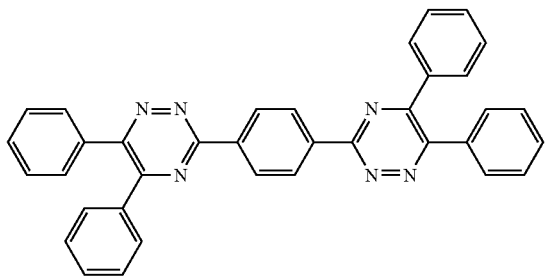

(1)

in particulate form; and
(b) UV filters selected from the group consisting of
($b_1$) Bis-Ethylhexyloxyphenol Methoxyphenyl Triazine;
($b_2$) Butyl Methoxydibenzoylmethane;
($b_4$) Ethylhexyl Triazone;
($b_6$) Ethylhexyl Methoxycinnamate;
($b_7$) Ethylhexyl Salicylate;
($b_8$) Homosalate;
($b_9$) Octocrylene;
($b_{10}$) Methylene Bis-Benzotriazolyl Tetramethylbutylphenol;
($b_{11}$) Phenylbenzimidazole Sulfonic Acid;
($b_{14}$) (2-{4-[2-(4-Diethylamino-2-hydroxy-benzoyl)-benzoyl]-piperazine-1-carbonyl}-phenyl)-(4-diethylamino-2-hydroxy-phenyl)-methanone;
($b_{15}$) BBDAPT; Benzoic acid, 4,4'-[[6-[[3-[1,3,3,3-tetramethyl-1-[(trimethylsilyl)oxy]-1 disiloxanyl]propyl]amino]-1,3,5-triazine-2,4-diyl]diimino]bis-, dibutyl ester;
($b_{16}$) benzylidene malonates;
($b_{17}$) merocyanine derivatives;
($b_{18}$) Bis(butylbenzoate) diaminotriazine aminopropylsiloxane;

(b₁₉) Bis-Ethylhexyloxyphenol Methoxyphenyl Triazine encapsulated in a polymer matrix;

(b₂₀) 2-(2H-Benzotriazol-2-yl)-6-[(2-ethylhexy loxy)methyl]-4-methylphenol; and (b₂₁) 2-Propenoic acid, 3-(4-methoxyphenyl)-, 2-methylphenyl ester, wherein the average particle size of component (a) is in the range from 0.02 to 2 micrometres; and wherein said composition contains from 0.1 to 15% by weight, based on the total weight of the composition, of the UV absorber mixture (a) and (b); and wherein said composition contains at least two of the UV filters selected from (b₁), (b₂), (b₄), (b₆)-(b₁₁), (b₁₄)-(b₁₇); and wherein said composition also contains a pharmaceutically or cosmetically acceptable excipient and wherein the compound of formula (1) is present in the micronized state.

23. A cosmetic or pharmaceutical composition comprising a UV filter combination of (a) an aqueous dispersion of 5,6,5',6'-tetraphenyl-3,3'-(1,4-Phenylene)bis(1,2,4-Triazine) corresponding to the formula

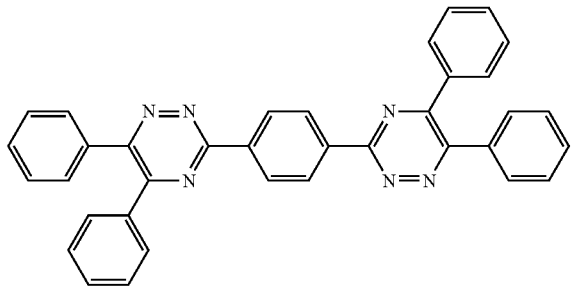

(1)

in particulate form; and (b) UV filters
  (b₁) Bis-Ethylhexyloxyphenol Methoxyphenyl Triazine and
  (b₄) Ethylhexyl Triazone;

wherein the average particle size of component (a) is in the range from 0.02 to 2 micrometres; and wherein said composition contains from 0.1 to 15% by weight, based on the total weight of the composition, of the UV absorber mixture (a) and (b); and and wherein said composition also contains a pharmaceutically or cosmetically acceptable excipient and wherein the compound of formula (1) is present in the micronized state.

* * * * *